United States Patent
Boss et al.

(10) Patent No.: US 9,801,925 B2
(45) Date of Patent: *Oct. 31, 2017

(54) POTENTIATION OF GLUCOSE ELIMINATION

(71) Applicant: MannKind Corporation, Valencia, CA (US)

(72) Inventors: Anders Hasager Boss, Princeton, NJ (US); Solomon S. Steiner, Mount Kisco, NY (US); Rodney J. Woods, New Hampton, NY (US); Joseph W. Sulner, Paramus, NJ (US)

(73) Assignee: MannKind Corporation, Westlake Village, CA (US)

( * ) Notice: Subject to any disclaimer, the term of this patent is extended or adjusted under 35 U.S.C. 154(b) by 210 days.

This patent is subject to a terminal disclaimer.

(21) Appl. No.: 14/639,860

(22) Filed: Mar. 5, 2015

(65) Prior Publication Data

US 2015/0174210 A1 Jun. 25, 2015

Related U.S. Application Data

(60) Continuation of application No. 11/329,686, filed on Jan. 10, 2006, now Pat. No. 9,006,175, which is a continuation-in-part of application No. 10/719,734, filed on Nov. 21, 2003, now Pat. No. 7,648,960, which is a continuation of application No. 10/224,761, filed on Aug. 20, 2002, now Pat. No. 6,652,885, which is a division of application No. 09/606,468, filed on Jun. 29, 2000, now Pat. No. 6,444,226.

(60) Provisional application No. 60/667,393, filed on Mar. 31, 2005, provisional application No. 60/643,070, filed on Jan. 10, 2005, provisional application No. 60/141,433, filed on Jun. 29, 1999.

(51) Int. Cl.
*A61K 38/28* (2006.01)
*A61K 47/48* (2006.01)
*A61K 9/00* (2006.01)

(52) U.S. Cl.
CPC .............. *A61K 38/28* (2013.01); *A61K 9/007* (2013.01); *A61K 9/0073* (2013.01); *A61K 47/48061* (2013.01); *Y10S 514/866* (2013.01)

(58) Field of Classification Search
None
See application file for complete search history.

(56) References Cited

U.S. PATENT DOCUMENTS

| | | |
|---|---|---|
| 2,549,303 A | 4/1951 | Friden |
| 2,754,276 A | 7/1956 | Joseph et al. |
| D189,076 S | 10/1960 | Altman |
| 3,337,740 A | 8/1967 | Gray et al. |
| 3,407,203 A | 10/1968 | Buijle |
| 3,518,340 A | 6/1970 | Raper |
| 3,622,053 A | 11/1971 | Ryden |
| 3,669,113 A | 6/1972 | Altounyan et al. |
| 3,673,698 A | 7/1972 | Guerard |
| 3,823,816 A | 7/1974 | Controullis et al. |
| 3,823,843 A | 7/1974 | Stephens et al. |
| 3,856,142 A | 12/1974 | Vessalo |
| 3,873,651 A | 3/1975 | Mosley, Jr. et al. |
| 3,906,950 A | 9/1975 | Cocozza |
| 3,921,637 A | 11/1975 | Bennie et al. |
| 3,976,773 A | 8/1976 | Curran et al. |
| 3,980,074 A | 9/1976 | Watt et al. |
| 3,998,226 A | 12/1976 | Harris |
| 4,013,075 A | 3/1977 | Cocozza |
| 4,018,619 A | 4/1977 | Webster et al. |
| 4,022,749 A | 5/1977 | Kuechler |
| 4,040,536 A | 8/1977 | Schwarz |
| 4,047,525 A | 9/1977 | Kulessa et al. |
| 4,066,756 A | 1/1978 | Orr et al. |
| 4,078,128 A | 3/1978 | Hoyt et al. |
| 4,091,077 A | 5/1978 | Smith et al. |
| 4,098,273 A | 7/1978 | Glenn |
| 4,102,953 A | 7/1978 | Johnson et al. |
| 4,110,240 A | 8/1978 | Leo et al. |
| 4,148,308 A | 4/1979 | Sayer |
| 4,153,689 A | 5/1979 | Hirai |
| D252,707 S | 8/1979 | Besnard |
| 4,168,002 A | 9/1979 | Crosby |
| 4,171,000 A | 10/1979 | Uhle |
| 4,175,556 A | 11/1979 | Freezer |

(Continued)

FOREIGN PATENT DOCUMENTS

| | | |
|---|---|---|
| CA | 2536047 A1 | 3/2005 |
| CA | 2551182 C | 8/2010 |

(Continued)

OTHER PUBLICATIONS

Amodeo et al., Pain peptides. Solution structure of orphanin FQ2. FEBS Letters, vol. 473, Issue 2, pp. 157-160 (2000).

(Continued)

*Primary Examiner* — Tracy Vivlemore
*Assistant Examiner* — Monica Shin
(74) *Attorney, Agent, or Firm* — K&L Gates LLP; Louis C. Cullman; Hal Gibson

(57) ABSTRACT

Methods related to the treatment of diabetes and improving the efficiency of insulin utilization are provided. The method enables effective control of prandial glucose levels while reducing the risk of postprandial hypoglycemia. In particular, methods of potentiating the activity of endogenous insulin in type 2 diabetics and exogenous long-acting insulin in diabetics requiring basal insulin replacement are provided.

14 Claims, 19 Drawing Sheets

(56) References Cited

U.S. PATENT DOCUMENTS

| | | |
|---|---|---|
| 4,187,129 A | 2/1980 | Bost et al. |
| 4,196,196 A | 4/1980 | Tiholiz |
| 4,206,758 A | 6/1980 | Hallworth et al. |
| 4,210,140 A | 7/1980 | James et al. |
| 4,211,769 A | 7/1980 | Okada |
| 4,268,460 A | 5/1981 | Boiarski et al. |
| 4,272,398 A | 6/1981 | Jaffe |
| 4,275,820 A | 6/1981 | LeBlond |
| 4,289,759 A | 9/1981 | Heavener |
| 4,294,829 A | 10/1981 | Suzuki |
| 4,300,546 A | 11/1981 | Kruber |
| 4,356,167 A | 10/1982 | Kelly |
| D269,463 S | 6/1983 | Young et al. |
| 4,407,525 A | 10/1983 | Hoppe |
| 4,456,007 A | 6/1984 | Nakao et al. |
| 4,483,922 A | 11/1984 | Carpenter |
| D276,654 S | 12/1984 | Snellman-Wasenius et al. |
| 4,487,327 A | 12/1984 | Grayson |
| 4,524,769 A | 6/1985 | Wetterlin |
| 4,526,804 A | 7/1985 | Escallon |
| 4,534,345 A | 8/1985 | Wetterlin |
| D282,209 S | 1/1986 | Newell et al. |
| 4,581,020 A | 4/1986 | Mittleman |
| 4,592,348 A | 6/1986 | Waters, IV et al. |
| 4,613,500 A | 9/1986 | Suzuki |
| 4,615,817 A | 10/1986 | McCoy |
| 4,624,861 A | 11/1986 | Yale et al. |
| 4,637,996 A | 1/1987 | Konishi |
| D288,852 S | 3/1987 | Miyoshi |
| 4,659,696 A | 4/1987 | Hirai et al. |
| 4,668,218 A | 5/1987 | Virtanen |
| 4,681,752 A | 7/1987 | Melillo |
| D295,321 S | 4/1988 | Hallworth |
| 4,757,066 A | 7/1988 | Shiokari et al. |
| 4,792,451 A | 12/1988 | Kim |
| 4,811,731 A | 3/1989 | Newell et al. |
| D301,273 S | 5/1989 | Leonard |
| 4,835,312 A | 5/1989 | Itoh et al. |
| 4,841,964 A | 6/1989 | Hurka et al. |
| 4,847,091 A | 7/1989 | Illum |
| 4,849,227 A | 7/1989 | Cho |
| 4,861,627 A | 8/1989 | Mathiowitz |
| 4,866,051 A | 9/1989 | Hunt et al. |
| 4,873,087 A | 10/1989 | Morishita et al. |
| 4,887,722 A | 12/1989 | Greenward, Sr. |
| 4,900,730 A | 2/1990 | Miyauchi |
| 4,907,583 A | 3/1990 | Wetterlin et al. |
| 4,925,673 A | 5/1990 | Steiner |
| 4,926,852 A | 5/1990 | Zoltan et al. |
| 4,927,555 A | 5/1990 | Colarusso, Jr. |
| 4,927,928 A | 5/1990 | Shroot et al. |
| 4,946,828 A | 8/1990 | Markussen |
| 4,981,295 A | 1/1991 | Belman et al. |
| 4,981,625 A | 1/1991 | Rhim et al. |
| 4,983,402 A | 1/1991 | Steiner et al. |
| 4,984,158 A | 1/1991 | Hillsman |
| 4,991,605 A | 2/1991 | Keritsis |
| 4,998,624 A | 3/1991 | Capes et al. |
| 5,006,343 A | 4/1991 | Benson |
| D316,902 S | 5/1991 | Hoefling |
| 5,017,383 A | 5/1991 | Ozawa et al. |
| 5,019,400 A | 5/1991 | Gombotz et al. |
| 5,021,376 A | 6/1991 | Nienburg et al. |
| 5,027,806 A | 7/1991 | Zoltan et al. |
| 5,042,975 A | 8/1991 | Chien |
| D321,570 S | 11/1991 | Blasdell et al. |
| 5,067,500 A | 11/1991 | Keritsis |
| 5,069,204 A | 12/1991 | Smith et al. |
| 5,074,418 A | 12/1991 | Buan et al. |
| 5,075,027 A | 12/1991 | Dixit et al. |
| 5,098,590 A | 3/1992 | Dixit et al. |
| 5,105,291 A | 4/1992 | Matsumoto et al. |
| D326,517 S | 5/1992 | Funai et al. |
| 5,110,007 A | 5/1992 | Law et al. |
| 5,110,823 A | 5/1992 | Hamaguchi et al. |
| 5,118,666 A | 6/1992 | Habener |
| 5,120,712 A | 6/1992 | Habener |
| 5,124,291 A | 6/1992 | Bremer et al. |
| 5,131,539 A | 7/1992 | Karita et al. |
| 5,139,878 A | 8/1992 | Kim |
| 5,145,684 A | 9/1992 | Liversidge et al. |
| 5,152,284 A | 10/1992 | Valentini et al. |
| D331,106 S | 11/1992 | Fuchs |
| 5,167,506 A | 12/1992 | Kilis et al. |
| 5,170,801 A | 12/1992 | Casper et al. |
| 5,188,837 A | 2/1993 | Domb |
| 5,196,049 A | 3/1993 | Coombs et al. |
| 5,201,308 A | 4/1993 | Newhouse |
| 5,203,768 A | 4/1993 | Haak et al. |
| 5,204,108 A | 4/1993 | Illum |
| 5,208,998 A | 5/1993 | Dyler, Jr. |
| 5,215,739 A | 6/1993 | Kamishita et al. |
| D337,636 S | 7/1993 | Kocinski |
| D338,062 S | 8/1993 | Yair |
| D338,268 S | 8/1993 | Kobayashi et al. |
| 5,239,992 A | 8/1993 | Bougamont et al. |
| 5,244,653 A | 9/1993 | Berke et al. |
| 5,250,287 A | 10/1993 | Cocozza |
| D340,975 S | 11/1993 | Sladek |
| 5,260,306 A | 11/1993 | Boardman et al. |
| 5,270,305 A | 12/1993 | Palmer |
| 5,287,850 A | 2/1994 | Haber et al. |
| D344,796 S | 3/1994 | Sochon et al. |
| D344,797 S | 3/1994 | Sochon et al. |
| D345,013 S | 3/1994 | Huck et al. |
| 5,301,666 A | 4/1994 | Lerk et al. |
| 5,306,453 A | 4/1994 | Shulman |
| D347,057 S | 5/1994 | Yair |
| D348,100 S | 6/1994 | Clarke |
| 5,320,094 A | 6/1994 | Laube et al. |
| D348,928 S | 7/1994 | Ashley et al. |
| D348,929 S | 7/1994 | Paton |
| 5,327,883 A | 7/1994 | Williams et al. |
| 5,328,464 A | 7/1994 | Kriesel et al. |
| 5,331,953 A | 7/1994 | Andersson et al. |
| 5,333,106 A | 7/1994 | Lanpher et al. |
| D349,572 S | 8/1994 | Jagnandan et al. |
| D350,193 S | 8/1994 | Huck et al. |
| 5,337,740 A | 8/1994 | Armstrong et al. |
| D350,602 S | 9/1994 | Hobbs et al. |
| D350,821 S | 9/1994 | Wright et al. |
| 5,351,683 A | 10/1994 | Chiesi et al. |
| 5,352,461 A | 10/1994 | Feldstein et al. |
| 5,354,562 A | 10/1994 | Platz |
| 5,358,734 A | 10/1994 | Lenox et al. |
| D352,107 S | 11/1994 | Meier et al. |
| 5,360,614 A | 11/1994 | Fox et al. |
| 5,363,842 A | 11/1994 | Mishelevich et al. |
| 5,364,838 A | 11/1994 | Rubsamen |
| 5,372,128 A | 12/1994 | Haber et al. |
| D355,029 S | 1/1995 | Kinneir et al. |
| 5,385,904 A | 1/1995 | Andersson et al. |
| 5,394,868 A | 3/1995 | Ambrosio et al. |
| 5,401,516 A | 3/1995 | Milstein et al. |
| D357,603 S | 4/1995 | Wolff |
| 5,404,871 A | 4/1995 | Goodman et al. |
| D358,880 S | 5/1995 | Mulhauser et al. |
| 5,413,804 A | 5/1995 | Rhodes |
| 5,415,162 A | 5/1995 | Casper et al. |
| D359,153 S | 6/1995 | Viggiano |
| D359,555 S | 6/1995 | Funai et al. |
| 5,424,286 A | 6/1995 | Eng |
| 5,437,271 A | 8/1995 | Hodson et al. |
| 5,443,841 A | 8/1995 | Milstein et al. |
| D362,500 S | 9/1995 | Cook et al. |
| 5,447,150 A | 9/1995 | Bacon |
| 5,447,151 A | 9/1995 | Bruna et al. |
| 5,447,728 A | 9/1995 | Milstein et al. |
| 5,451,410 A | 9/1995 | Milstein et al. |
| D363,775 S | 10/1995 | Hobbs |
| 5,454,871 A | 10/1995 | Liaw et al. |
| 5,455,335 A | 10/1995 | Kahne et al. |
| 5,458,135 A | 10/1995 | Patton et al. |
| 5,469,750 A | 11/1995 | Lloyd et al. |

(56) References Cited

U.S. PATENT DOCUMENTS

| | | |
|---|---|---|
| 5,469,971 A | 11/1995 | Chilton et al. |
| 5,476,093 A | 12/1995 | Laniken |
| 5,477,285 A | 12/1995 | Riddle et al. |
| D365,876 S | 1/1996 | Chawla |
| 5,482,032 A | 1/1996 | Smith et al. |
| 5,482,927 A | 1/1996 | Maniar et al. |
| 5,483,954 A | 1/1996 | Mecikalski |
| 5,484,606 A | 1/1996 | Dhaber et al. |
| 5,487,378 A | 1/1996 | Robertson et al. |
| 5,492,112 A | 2/1996 | Mecikalski et al. |
| D368,364 S | 4/1996 | Reitano et al. |
| 5,503,144 A | 4/1996 | Bacon |
| 5,503,852 A | 4/1996 | Steiner et al. |
| 5,505,194 A | 4/1996 | Adjei et al. |
| 5,506,203 A | 4/1996 | Backstorm et al. |
| D370,255 S | 5/1996 | Yamamoto et al. |
| 5,514,646 A | 5/1996 | Chance et al. |
| 5,518,998 A | 5/1996 | Backstrom et al. |
| 5,524,613 A | 6/1996 | Haber et al. |
| 5,532,461 A | 7/1996 | Crummenauer et al. |
| 5,533,502 A | 7/1996 | Piper |
| 5,533,505 A | 7/1996 | Kallstrand et al. |
| 5,541,155 A | 7/1996 | Leone-Bay |
| 5,542,411 A | 8/1996 | Rex |
| 5,542,539 A | 8/1996 | Early |
| 5,545,618 A | 8/1996 | Buckley et al. |
| 5,547,929 A | 8/1996 | Anderson, Jr. et al. |
| 5,562,909 A | 10/1996 | Allcock et al. |
| 5,562,918 A | 10/1996 | Stimpson |
| 5,568,884 A | 10/1996 | Bruna |
| 5,570,810 A | 11/1996 | Lambelet, Jr. et al. |
| 5,571,795 A | 11/1996 | Kahne et al. |
| 5,574,008 A | 11/1996 | Johnson et al. |
| 5,577,497 A | 11/1996 | Mecikalski et al. |
| 5,578,323 A | 11/1996 | Milstein et al. |
| 5,584,417 A | 12/1996 | Graf et al. |
| D377,215 S | 1/1997 | Rand |
| D377,686 S | 1/1997 | Waldeck et al. |
| 5,595,175 A | 1/1997 | Malcher et al. |
| 5,596,701 A | 1/1997 | Augusteijn et al. |
| D377,861 S | 2/1997 | Jacober |
| 5,598,835 A | 2/1997 | von Schrader |
| 5,601,846 A | 2/1997 | Milstein et al. |
| 5,610,271 A | 3/1997 | Dooley et al. |
| 5,614,492 A | 3/1997 | Habener |
| 5,615,670 A | 4/1997 | Rhodes et al. |
| 5,617,844 A | 4/1997 | King |
| 5,619,984 A | 4/1997 | Hodson et al. |
| 5,622,164 A | 4/1997 | Kilis et al. |
| 5,622,166 A | 4/1997 | Eisele et al. |
| 5,623,724 A | 4/1997 | Gurkovich et al. |
| 5,623,920 A | 4/1997 | Bryant |
| D379,506 S | 5/1997 | Maher |
| 5,629,020 A | 5/1997 | Leone-Bay |
| 5,631,224 A | 5/1997 | Efendic et al. |
| 5,632,971 A | 5/1997 | Yang |
| 5,634,900 A | 6/1997 | Makino et al. |
| 5,639,441 A | 6/1997 | Sievers et al. |
| 5,641,861 A | 6/1997 | Dooley et al. |
| D381,416 S | 7/1997 | Hansson et al. |
| 5,642,727 A | 7/1997 | Datta et al. |
| 5,642,728 A | 7/1997 | Andersson et al. |
| 5,643,957 A | 7/1997 | Leone-Bay et al. |
| 5,645,051 A | 7/1997 | Schultz |
| 5,651,359 A | 7/1997 | Bougamont et al. |
| 5,653,961 A | 8/1997 | McNally et al. |
| 5,655,516 A | 8/1997 | Goodman et al. |
| 5,655,523 A | 8/1997 | Hodson et al. |
| 5,657,748 A | 8/1997 | Braithwaite |
| 5,658,878 A | 8/1997 | Backstrom et al. |
| 5,660,169 A | 8/1997 | Kallstrand et al. |
| 5,672,581 A | 9/1997 | Rubsamen et al. |
| 5,673,686 A | 10/1997 | Villax et al. |
| 5,679,377 A | 10/1997 | Bernstein et al. |
| 5,687,710 A | 11/1997 | Ambrosio et al. |
| 5,690,910 A | 11/1997 | Ahmed et al. |
| 5,693,338 A | 12/1997 | Milstein |
| 5,699,789 A | 12/1997 | Hendricks |
| D389,238 S | 1/1998 | Kirk, III et al. |
| D389,570 S | 1/1998 | Savolainen |
| 5,705,483 A | 1/1998 | Galloway et al. |
| D390,651 S | 2/1998 | Smith et al. |
| D390,653 S | 2/1998 | Blasdell et al. |
| 5,714,007 A | 2/1998 | Pletcher et al. |
| 5,714,167 A | 2/1998 | Milstein et al. |
| 5,727,333 A | 3/1998 | Folan |
| 5,727,546 A | 3/1998 | Clarke et al. |
| 5,740,793 A | 4/1998 | Hodson et al. |
| 5,740,794 A | 4/1998 | Smith et al. |
| 5,746,197 A | 5/1998 | Williams |
| 5,746,227 A | 5/1998 | Rose et al. |
| 5,747,445 A | 5/1998 | Backstrom et al. |
| 5,752,505 A | 5/1998 | Ohki et al. |
| 5,755,218 A | 5/1998 | Johansson et al. |
| D395,147 S | 6/1998 | Vidgren et al. |
| D395,499 S | 6/1998 | Eisele et al. |
| 5,758,638 A | 6/1998 | Kreamer |
| 5,763,396 A | 6/1998 | Weiner et al. |
| 5,766,620 A | 6/1998 | Heiber et al. |
| 5,766,633 A | 6/1998 | Milstein et al. |
| 5,769,073 A | 6/1998 | Eason et al. |
| 5,772,085 A | 6/1998 | Bryant et al. |
| RE35,862 E | 7/1998 | Steiner et al. |
| 5,775,320 A | 7/1998 | Patton et al. |
| 5,785,049 A | 7/1998 | Smith et al. |
| 5,785,989 A | 7/1998 | Stanley et al. |
| D397,435 S | 8/1998 | Naumann |
| 5,792,451 A | 8/1998 | Sarubbi et al. |
| 5,794,613 A | 8/1998 | Piskorski |
| 5,797,391 A | 8/1998 | Cook et al. |
| D398,992 S | 9/1998 | Feret |
| 5,799,821 A | 9/1998 | Lambelet, Jr. et al. |
| 5,807,315 A | 9/1998 | Va Antwerp et al. |
| 5,809,997 A | 9/1998 | Wolf |
| 5,811,127 A | 9/1998 | Milstein et al. |
| 5,813,397 A | 9/1998 | Goodman et al. |
| 5,817,343 A | 10/1998 | Burke |
| 5,824,345 A | 10/1998 | Milstein et al. |
| 5,839,429 A | 11/1998 | Marnfeldt et al. |
| 5,840,279 A | 11/1998 | Narodylo et al. |
| 5,840,340 A | 11/1998 | Milstein et al. |
| 5,846,447 A | 12/1998 | Beatty |
| 5,848,589 A | 12/1998 | Welnetz |
| 5,849,322 A | 12/1998 | Ebert et al. |
| 5,857,457 A | 1/1999 | Hyppola |
| 5,858,099 A | 1/1999 | Sun et al. |
| 5,865,012 A | 2/1999 | Hansson et al. |
| 5,868,774 A | 2/1999 | Reil |
| 5,874,064 A | 2/1999 | Edwards et al. |
| 5,875,776 A | 3/1999 | Vaghefi |
| 5,877,174 A | 3/1999 | Ono et al. |
| 5,881,719 A | 3/1999 | Gottenauer et al. |
| 5,881,721 A | 3/1999 | Bunce et al. |
| 5,884,620 A | 3/1999 | Gonda et al. |
| 5,888,477 A | 3/1999 | Gonda et al. |
| 5,896,855 A | 4/1999 | Hobbs et al. |
| 5,901,703 A | 5/1999 | Ohki et al. |
| 5,904,139 A | 5/1999 | Hauser |
| D410,541 S | 6/1999 | Moulin |
| D411,005 S | 6/1999 | Coe |
| 5,908,639 A | 6/1999 | Simpkin et al. |
| 5,912,011 A | 6/1999 | Makino et al. |
| 5,918,594 A | 7/1999 | Asking et al. |
| 5,919,897 A | 7/1999 | Dooley et al. |
| 5,921,237 A | 7/1999 | Eisele et al. |
| 5,922,253 A | 7/1999 | Herbert et al. |
| 5,924,419 A | 7/1999 | Kotliar |
| 5,929,027 A | 7/1999 | Takama et al. |
| D412,572 S | 8/1999 | Gray |
| D412,744 S | 8/1999 | Braithwaite |
| D412,978 S | 8/1999 | Cameron |
| D412,979 S | 8/1999 | Weinstein et al. |
| 5,934,273 A | 8/1999 | Andersson et al. |
| 5,942,242 A | 8/1999 | Mizushima et al. |

(56) References Cited

U.S. PATENT DOCUMENTS

| | | | |
|---|---|---|---|
| 5,948,749 | A | 9/1999 | Igarashi et al. |
| 5,952,008 | A | 9/1999 | Backstrom et al. |
| 5,954,047 | A | 9/1999 | Armer et al. |
| 5,965,701 | A | 10/1999 | Junien |
| 5,971,951 | A | 10/1999 | Ruskewicz |
| D416,085 | S | 11/1999 | Forssell et al. |
| D416,621 | S | 11/1999 | Forssell et al. |
| D416,998 | S | 11/1999 | Hodson et al. |
| D417,271 | S | 11/1999 | Denyer et al. |
| 5,975,347 | A | 11/1999 | Lambelet, Jr. et al. |
| 5,976,569 | A | 11/1999 | Milstein |
| 5,976,574 | A | 11/1999 | Gordon |
| 5,977,071 | A | 11/1999 | Galloway et al. |
| 5,980,865 | A | 11/1999 | Ahmed et al. |
| 5,981,488 | A | 11/1999 | Hoffmann |
| 5,983,893 | A | 11/1999 | Wetterlin |
| 5,985,248 | A | 11/1999 | Gordon et al. |
| 5,985,309 | A | 11/1999 | Edwards et al. |
| 5,990,077 | A | 11/1999 | Drucker |
| D417,732 | S | 12/1999 | Dagsland et al. |
| D417,912 | S | 12/1999 | Dagsland et al. |
| 5,996,577 | A | 12/1999 | Ohki et al. |
| 5,997,848 | A | 12/1999 | Patton et al. |
| 6,001,336 | A | 12/1999 | Gordon |
| 6,006,747 | A | 12/1999 | Eisele et al. |
| 6,006,753 | A | 12/1999 | Efendic |
| D418,600 | S | 1/2000 | Haerle |
| D420,736 | S | 2/2000 | Moulin |
| 6,026,809 | A | 2/2000 | Abrams et al. |
| 6,029,663 | A | 2/2000 | Eisele et al. |
| D421,800 | S | 3/2000 | Doat |
| 6,039,208 | A | 3/2000 | Lambelet et al. |
| 6,043,214 | A | 3/2000 | Jensen et al. |
| 6,045,828 | A | 4/2000 | Bystorm et al. |
| 6,051,256 | A | 4/2000 | Platz et al. |
| 6,051,551 | A | 4/2000 | Hughes et al. |
| 6,055,980 | A | 5/2000 | Mecikalski et al. |
| 6,056,169 | A | 5/2000 | Bruna et al. |
| 6,060,069 | A | 5/2000 | Hill et al. |
| 6,063,910 | A | 5/2000 | Debenedetti et al. |
| 6,071,497 | A | 6/2000 | Steiner et al. |
| 6,073,629 | A | 6/2000 | Hardy et al. |
| 6,076,521 | A | 6/2000 | Lindahl et al. |
| 6,077,543 | A | 6/2000 | Gordon et al. |
| 6,080,762 | A | 6/2000 | Allen et al. |
| D428,486 | S | 7/2000 | Schuckmann |
| 6,085,745 | A | 7/2000 | Levander et al. |
| 6,087,334 | A | 7/2000 | Beeley et al. |
| 6,087,351 | A | 7/2000 | Nyce |
| 6,089,228 | A | 7/2000 | Smith et al. |
| 6,095,136 | A | 8/2000 | Virtanen |
| 6,098,618 | A | 8/2000 | Jennings et al. |
| 6,098,619 | A | 8/2000 | Britto et al. |
| 6,099,517 | A | 8/2000 | Daugherty |
| 6,102,035 | A | 8/2000 | Asking et al. |
| 6,105,571 | A | 8/2000 | Coffee |
| 6,105,574 | A | 8/2000 | Jahnsson |
| 6,109,261 | A | 8/2000 | Clarke et al. |
| 6,109,481 | A | 8/2000 | Alexander et al. |
| 6,116,237 | A | 9/2000 | Schultz |
| 6,116,238 | A | 9/2000 | Jackson et al. |
| 6,116,239 | A | 9/2000 | Volgyesi |
| 6,119,684 | A | 9/2000 | Nohl et al. |
| 6,119,688 | A | 9/2000 | Whaley et al. |
| 6,131,567 | A | 10/2000 | Gonda et al. |
| 6,132,766 | A | 10/2000 | Sankaram et al. |
| 6,133,235 | A | 10/2000 | Galloway et al. |
| 6,142,145 | A | 11/2000 | Dagsland |
| 6,152,130 | A | 11/2000 | Abrams |
| 6,153,613 | A | 11/2000 | Ono et al. |
| 6,155,423 | A | 12/2000 | Katzne et al. |
| 6,156,114 | A | 12/2000 | Bell et al. |
| 6,158,431 | A | 12/2000 | Poole |
| 6,159,360 | A | 12/2000 | Gerteis et al. |
| RE37,053 | E | 2/2001 | Hanes et al. |
| 6,182,655 | B1 | 2/2001 | Keller et al. |
| 6,187,291 | B1 | 2/2001 | Weinstein et al. |
| 6,191,102 | B1 | 2/2001 | DiMarchi et al. |
| 6,192,876 | B1 | 2/2001 | Denyer et al. |
| 6,193,844 | B1 | 2/2001 | McLaughlin et al. |
| 6,193,957 | B1 | 2/2001 | Ahmed |
| D438,612 | S | 3/2001 | Suh |
| D439,325 | S | 3/2001 | Frost |
| D439,656 | S | 3/2001 | Andersson et al. |
| 6,198,847 | B1 | 3/2001 | Washizawa |
| D441,446 | S | 5/2001 | Dagsland et al. |
| D441,859 | S | 5/2001 | Pera |
| D442,685 | S | 5/2001 | Sladek |
| 6,235,725 | B1 | 5/2001 | Ahmed |
| D444,226 | S | 6/2001 | Geert-Jensen et al. |
| 6,250,300 | B1 | 6/2001 | Andersson et al. |
| 6,254,854 | B1 | 7/2001 | Edwards et al. |
| 6,257,232 | B1 | 7/2001 | Andersson et al. |
| 6,258,816 | B1 | 7/2001 | Singh et al. |
| 6,263,871 | B1 | 7/2001 | Brown et al. |
| 6,269,952 | B1 | 8/2001 | Watt et al. |
| 6,273,084 | B1 | 8/2001 | Frid |
| 6,273,085 | B1 | 8/2001 | Eisele et al. |
| 6,273,086 | B1 | 8/2001 | Ohki et al. |
| 6,277,819 | B1 | 8/2001 | Efendic |
| 6,279,511 | B1 | 8/2001 | Loughnane |
| D448,076 | S | 9/2001 | von Schuckmann |
| 6,286,506 | B1 | 9/2001 | MacAndrew et al. |
| 6,286,507 | B1 | 9/2001 | Jahnsson |
| 6,294,204 | B1 | 9/2001 | Rossling et al. |
| D449,684 | S | 10/2001 | Christrup et al. |
| 6,298,846 | B1 | 10/2001 | Ohki et al. |
| 6,298,847 | B1 | 10/2001 | Datta et al. |
| D450,117 | S | 11/2001 | Braithwaite et al. |
| D451,597 | S | 12/2001 | Suh |
| 6,328,034 | B1 | 12/2001 | Eisele et al. |
| 6,331,318 | B1 | 12/2001 | Milstein |
| D452,910 | S | 1/2002 | Braithwaite et al. |
| 6,335,316 | B1 | 1/2002 | Hughes et al. |
| D453,264 | S | 2/2002 | Acevedo, Jr. |
| 6,347,629 | B1 | 2/2002 | Braithwaite |
| 6,348,447 | B1 | 2/2002 | Hellstorm et al. |
| 6,357,442 | B1 | 3/2002 | Casper et al. |
| 6,358,058 | B1 | 3/2002 | Strupat et al. |
| 6,358,924 | B1 | 3/2002 | Hoffmann |
| 6,360,743 | B1 | 3/2002 | Andersson et al. |
| 6,360,929 | B1 | 3/2002 | McCarthy |
| D455,208 | S | 4/2002 | Bacon et al. |
| 6,363,932 | B1 | 4/2002 | Forchione et al. |
| 6,365,190 | B1 | 4/2002 | Gordon et al. |
| 6,372,258 | B1 | 4/2002 | Platz et al. |
| 6,375,975 | B1 | 4/2002 | Modi |
| 6,380,357 | B2 | 4/2002 | Hermeling et al. |
| 6,386,195 | B1 | 5/2002 | Coffee |
| 6,388,053 | B1 | 5/2002 | Galloway et al. |
| 6,394,085 | B1 | 5/2002 | Hardy et al. |
| 6,395,300 | B1 | 5/2002 | Straub et al. |
| 6,395,744 | B1 | 5/2002 | Adams et al. |
| 6,395,774 | B1 | 5/2002 | Milstein |
| 6,410,513 | B1 | 6/2002 | Galloway et al. |
| D460,173 | S | 7/2002 | Harrison et al. |
| 6,415,784 | B1 | 7/2002 | Christrup et al. |
| 6,418,926 | B1 | 7/2002 | Chawla |
| 6,423,344 | B1 | 7/2002 | Platz et al. |
| D461,239 | S | 8/2002 | Cassidy |
| 6,427,688 | B1 | 8/2002 | Ligotke et al. |
| 6,428,771 | B1 | 8/2002 | Steiner et al. |
| 6,428,805 | B1 | 8/2002 | Dohi et al. |
| 6,432,383 | B1 | 8/2002 | Modi |
| 6,436,443 | B2 | 8/2002 | Edwards et al. |
| 6,439,227 | B1 | 8/2002 | Myrman et al. |
| 6,440,463 | B1 | 8/2002 | Feldstein et al. |
| 6,441,172 | B1 | 8/2002 | Nefzi et al. |
| D463,544 | S | 9/2002 | Engelberth et al. |
| 6,443,143 | B1 | 9/2002 | Ishida et al. |
| 6,444,226 | B1 | 9/2002 | Steiner et al. |
| 6,446,626 | B1 | 9/2002 | Virtanen |
| 6,446,627 | B1 | 9/2002 | Bowman et al. |
| 6,447,750 | B1 | 9/2002 | Cutie et al. |

(56) References Cited

U.S. PATENT DOCUMENTS

| | | |
|---|---|---|
| 6,447,751 B1 | 9/2002 | Weinstein et al. |
| 6,447,753 B2 | 9/2002 | Edwards et al. |
| 6,451,337 B1 | 9/2002 | Smith et al. |
| 6,457,470 B1 | 10/2002 | Coffee |
| 6,468,507 B1 | 10/2002 | Cutie et al. |
| 6,470,884 B2 | 10/2002 | Horlin |
| 6,479,049 B1 | 11/2002 | Platz et al. |
| 6,484,715 B1 | 11/2002 | Ritsche et al. |
| 6,484,717 B1 | 11/2002 | Dagsland et al. |
| D469,527 S | 1/2003 | Keller et al. |
| 6,503,480 B1 | 1/2003 | Edwards et al. |
| 6,509,006 B1 | 1/2003 | Platz et al. |
| 6,509,313 B1 | 1/2003 | Smith |
| D469,866 S | 2/2003 | Albulet et al. |
| 6,514,482 B1 | 2/2003 | Bartus et al. |
| 6,518,239 B1 | 2/2003 | Kuo et al. |
| 6,523,536 B2 | 2/2003 | Fugelsang et al. |
| D471,273 S | 3/2003 | Albulet et al. |
| 6,528,096 B1 | 3/2003 | Musa et al. |
| 6,532,437 B1 | 3/2003 | Clardy et al. |
| 6,536,427 B2 | 3/2003 | Davies et al. |
| D473,298 S | 4/2003 | Bowman et al. |
| D473,640 S | 4/2003 | Cuffaro et al. |
| 6,540,672 B1 | 4/2003 | Simonsen et al. |
| 6,540,982 B1 | 4/2003 | Adjei et al. |
| 6,540,983 B1 | 4/2003 | Adjei et al. |
| 6,543,448 B1 | 4/2003 | Smith et al. |
| 6,546,929 B2 | 4/2003 | Burr et al. |
| 6,555,127 B2 | 4/2003 | Steiner |
| 6,555,521 B2 | 4/2003 | Hermeling et al. |
| D474,536 S | 5/2003 | Albulet et al. |
| D475,133 S | 5/2003 | McLuckie |
| 6,557,549 B2 | 5/2003 | Schmidt et al. |
| 6,561,186 B2 | 5/2003 | Casper et al. |
| 6,567,686 B2 | 5/2003 | Sexton |
| 6,568,390 B2 | 5/2003 | Nichols et al. |
| 6,569,406 B2 | 5/2003 | Stevenson et al. |
| 6,571,793 B1 | 6/2003 | Nilsson et al. |
| 6,572,893 B2 | 6/2003 | Gordon et al. |
| 6,575,160 B1 | 6/2003 | Volgyesi |
| 6,575,162 B1 | 6/2003 | Rand |
| 6,578,571 B1 | 6/2003 | Watt |
| 6,582,728 B1 | 6/2003 | Platz et al. |
| 6,583,111 B1 | 6/2003 | DiMarchi |
| D477,665 S | 7/2003 | Myrman et al. |
| 6,589,560 B2 | 7/2003 | Foster et al. |
| 6,591,832 B1 | 7/2003 | DeJonge |
| 6,592,904 B2 | 7/2003 | Platz et al. |
| 6,595,205 B2 | 7/2003 | Andersson et al. |
| 6,595,208 B1 | 7/2003 | Coffee et al. |
| D478,983 S | 8/2003 | Whitehall et al. |
| 6,606,992 B1 | 8/2003 | Schuler et al. |
| D479,745 S | 9/2003 | Albulet et al. |
| 6,613,308 B2 | 9/2003 | Bartus et al. |
| 6,615,987 B1 | 9/2003 | Greenhill et al. |
| 6,620,910 B1 | 9/2003 | Calas et al. |
| 6,626,173 B2 | 9/2003 | Genova et al. |
| D480,806 S | 10/2003 | Engelberth et al. |
| 6,630,169 B1 | 10/2003 | Bot et al. |
| 6,632,258 B1 | 10/2003 | Wheelock et al. |
| 6,632,456 B1 | 10/2003 | Backstrom et al. |
| 6,635,283 B2 | 10/2003 | Edwards et al. |
| 6,637,431 B2 | 10/2003 | Ekelius et al. |
| 6,640,050 B2 | 10/2003 | Nichols et al. |
| 6,644,309 B2 | 11/2003 | Casper et al. |
| 6,645,468 B2 | 11/2003 | Cutie et al. |
| 6,645,504 B1 | 11/2003 | Weiner et al. |
| 6,652,838 B2 | 11/2003 | Weinstein et al. |
| 6,652,885 B2 | 11/2003 | Steiner et al. |
| D483,860 S | 12/2003 | Knoch |
| 6,655,379 B2 | 12/2003 | Clark et al. |
| 6,655,380 B1 | 12/2003 | Andersson et al. |
| 6,655,381 B2 | 12/2003 | Keane et al. |
| 6,660,716 B1 | 12/2003 | Yakubu-Madus et al. |
| 6,663,898 B2 | 12/2003 | Milstein |
| 6,668,826 B1 | 12/2003 | Myrman et al. |
| 6,672,304 B1 | 1/2004 | Casper et al. |
| 6,676,931 B2 | 1/2004 | Dugger, III |
| 6,679,255 B2 | 1/2004 | Pera |
| 6,681,767 B1 | 1/2004 | Patton et al. |
| 6,681,768 B2 | 1/2004 | Haaije de Boer et al. |
| 6,685,967 B2 | 2/2004 | Patton et al. |
| 6,698,421 B2 | 3/2004 | Attolini |
| 6,698,422 B2 | 3/2004 | Fugelsang et al. |
| 6,701,917 B2 | 3/2004 | O'Leary |
| 6,703,361 B2 | 3/2004 | Weiner et al. |
| 6,703,365 B2 | 3/2004 | Galloway et al. |
| 6,703,381 B1 | 3/2004 | Ekwuribe et al. |
| 6,705,313 B2 | 3/2004 | Niccolai |
| 6,715,486 B2 | 4/2004 | Gieschen et al. |
| 6,715,487 B2 | 4/2004 | Nichols et al. |
| 6,718,972 B2 | 4/2004 | O'Leary |
| 6,720,407 B1 | 4/2004 | Hughes et al. |
| 6,722,363 B1 | 4/2004 | von Schuckmann |
| D489,448 S | 5/2004 | Shayan |
| 6,729,324 B2 | 5/2004 | Casper et al. |
| 6,729,328 B2 | 5/2004 | Goldemann |
| 6,737,045 B2 | 5/2004 | Patton |
| 6,745,761 B2 | 6/2004 | Christup et al. |
| 6,747,006 B2 | 6/2004 | Efendic |
| 6,748,946 B1 | 6/2004 | Rand et al. |
| 6,748,947 B2 | 6/2004 | Keane et al. |
| 6,752,145 B1 | 6/2004 | Bonney et al. |
| 6,755,190 B2 | 6/2004 | Rasmussen |
| D492,769 S | 7/2004 | Hatanaka |
| D493,220 S | 7/2004 | Burge et al. |
| D493,519 S | 7/2004 | Jonsson et al. |
| 6,774,112 B2 | 8/2004 | Gougoutas |
| 6,787,152 B2 | 9/2004 | Kirby et al. |
| 6,790,496 B1 | 9/2004 | Levander et al. |
| 6,792,945 B2 | 9/2004 | Davies et al. |
| 6,797,258 B2 | 9/2004 | Platz et al. |
| 6,799,572 B2 | 10/2004 | Nichols et al. |
| 6,800,643 B2 | 10/2004 | Cuenoud et al. |
| 6,803,044 B1 | 10/2004 | Catania et al. |
| 6,821,949 B2 | 11/2004 | Bridon et al. |
| 6,823,863 B2 | 11/2004 | Huxham et al. |
| D499,802 S | 12/2004 | Pinon et al. |
| 6,830,046 B2 | 12/2004 | Blakley et al. |
| 6,838,075 B2 | 1/2005 | Stevenson et al. |
| 6,838,076 B2 | 1/2005 | Patton et al. |
| 6,847,595 B2 | 1/2005 | Tanaka |
| 6,848,443 B2 | 2/2005 | Schmidt et al. |
| 6,849,708 B1 | 2/2005 | Habener |
| 6,852,690 B1 | 2/2005 | Nauck et al. |
| 6,858,199 B1 | 2/2005 | Edwards et al. |
| 6,860,262 B2 | 3/2005 | Christup et al. |
| 6,866,037 B1 | 3/2005 | Aslin et al. |
| 6,871,646 B2 | 3/2005 | Keane et al. |
| 6,871,647 B2 | 3/2005 | Allan et al. |
| 6,880,554 B1 | 4/2005 | Coffee |
| 6,881,423 B2 | 4/2005 | Dohi et al. |
| 6,884,435 B2 | 4/2005 | O'Hagan et al. |
| 6,887,459 B1 | 5/2005 | Haeberlin |
| 6,887,849 B2 | 5/2005 | Bridon et al. |
| 6,889,687 B1 | 5/2005 | Olsson |
| 6,892,728 B2 | 5/2005 | Helgesson et al. |
| 6,896,906 B2 | 5/2005 | Hastedt et al. |
| D506,680 S | 6/2005 | Saelzer |
| 6,904,907 B2 | 6/2005 | Speldrich et al. |
| 6,906,030 B2 | 6/2005 | Milstein |
| 6,916,354 B2 | 7/2005 | Elliott |
| 6,918,991 B2 | 7/2005 | Chickering, III et al. |
| 6,921,458 B2 | 7/2005 | Chickering, III et al. |
| 6,921,528 B2 | 7/2005 | Edwards et al. |
| 6,923,175 B2 | 8/2005 | Poole et al. |
| D509,296 S | 9/2005 | Minshull et al. |
| D509,898 S | 9/2005 | Bunce et al. |
| 6,948,496 B2 | 9/2005 | Eason et al. |
| 6,949,258 B2 | 9/2005 | Zhang |
| 6,951,215 B1 | 10/2005 | Hoffman |
| 6,953,812 B2 | 10/2005 | Jorgenson et al. |
| D511,208 S | 11/2005 | Pardonge et al. |
| D511,977 S | 11/2005 | Saelzer |

(56) References Cited

U.S. PATENT DOCUMENTS

| | | |
|---|---|---|
| 6,962,006 B2 | 11/2005 | Chickering, III et al. |
| D512,777 S | 12/2005 | Beisner et al. |
| 6,979,437 B2 | 12/2005 | Bartus et al. |
| D514,222 S | 1/2006 | Andersson et al. |
| 6,981,499 B2 | 1/2006 | Andersson et al. |
| 6,989,155 B1 | 1/2006 | Ganderton et al. |
| 6,991,779 B2 | 1/2006 | Steiner et al. |
| D515,696 S | 2/2006 | Lucking et al. |
| D515,924 S | 2/2006 | Grant |
| D516,211 S | 2/2006 | Minshull et al. |
| 6,998,387 B1 | 2/2006 | Goke et al. |
| D518,170 S | 3/2006 | Clarke et al. |
| D518,171 S | 3/2006 | Anderson et al. |
| 7,022,674 B2 | 4/2006 | DeFelippis et al. |
| 7,025,056 B2 | 4/2006 | Eason et al. |
| 7,028,686 B2 | 4/2006 | Gonda et al. |
| 7,030,084 B2 | 4/2006 | Ekwuribe et al. |
| 7,032,593 B2 | 4/2006 | Johnston et al. |
| 7,035,294 B2 | 4/2006 | Dove et al. |
| 7,047,967 B2 | 5/2006 | Knudsen |
| 7,048,908 B2 | 5/2006 | Basu et al. |
| 7,060,274 B2 | 6/2006 | Blumberg et al. |
| 7,067,129 B2 | 6/2006 | Blumberg et al. |
| 7,077,130 B2 | 7/2006 | Nichols et al. |
| 7,080,642 B2 | 7/2006 | Hodson et al. |
| 7,084,243 B2 | 8/2006 | Glaesner et al. |
| 7,093,594 B2 | 8/2006 | Harrison et al. |
| 7,093,595 B2 | 8/2006 | Nesbitt |
| D527,817 S | 9/2006 | Ziegler et al. |
| 7,101,843 B2 | 9/2006 | Glaesner et al. |
| 7,101,866 B2 | 9/2006 | Biggadike et al. |
| 7,107,988 B2 | 9/2006 | Pinon et al. |
| D529,604 S | 10/2006 | Young et al. |
| 7,125,566 B2 | 10/2006 | Etter |
| 7,128,067 B2 | 10/2006 | Byron et al. |
| 7,131,441 B1 | 11/2006 | Keller et al. |
| 7,132,115 B2 | 11/2006 | Musa et al. |
| 7,140,365 B2 | 11/2006 | Poole et al. |
| D533,268 S | 12/2006 | Olfati |
| 7,143,764 B1 | 12/2006 | Dagsland et al. |
| 7,143,765 B2 | 12/2006 | Asking et al. |
| 7,144,863 B2 | 12/2006 | DeFelippis et al. |
| 7,146,978 B2 | 12/2006 | Edwards et al. |
| 7,151,456 B2 | 12/2006 | Godfrey |
| 7,163,014 B2 | 1/2007 | Nichols et al. |
| D537,522 S | 2/2007 | Cox et al. |
| 7,171,965 B2 | 2/2007 | Young et al. |
| 7,172,768 B2 | 2/2007 | Hastedt et al. |
| 7,179,788 B2 | 2/2007 | DeFelippis et al. |
| D537,936 S | 3/2007 | Cox et al. |
| D538,423 S | 3/2007 | Berube et al. |
| 7,185,650 B2 | 3/2007 | Huber et al. |
| 7,198,806 B2 | 4/2007 | Berndt |
| 7,211,557 B2 | 5/2007 | DiMarchi et al. |
| 7,219,664 B2 | 5/2007 | Ruckdeschel et al. |
| 7,223,728 B2 | 5/2007 | Yakubu-Madus et al. |
| D544,093 S | 6/2007 | Eriksen |
| 7,231,919 B2 | 6/2007 | Giroux |
| 7,232,897 B2 | 6/2007 | Hotamisligil et al. |
| 7,234,459 B2 | 6/2007 | Del Bon |
| 7,234,460 B2 | 6/2007 | Greenleaf et al. |
| 7,234,464 B2 | 6/2007 | Goede et al. |
| 7,238,663 B2 | 7/2007 | DeFelippis et al. |
| 7,246,617 B1 | 7/2007 | Hammer et al. |
| D548,330 S | 8/2007 | Cox et al. |
| D548,618 S | 8/2007 | Ferguson et al. |
| D548,619 S | 8/2007 | Ferguson et al. |
| D548,833 S | 8/2007 | Young et al. |
| D549,111 S | 8/2007 | Ferguson et al. |
| 7,258,118 B2 | 8/2007 | Goede et al. |
| 7,259,233 B2 | 8/2007 | Dodd et al. |
| D550,835 S | 9/2007 | Tanaka et al. |
| 7,270,124 B2 | 9/2007 | Rasmussen |
| D552,729 S | 10/2007 | Cox et al. |
| 7,276,534 B2 | 10/2007 | Milstein |
| 7,278,419 B2 | 10/2007 | Gonda |
| 7,278,426 B2 | 10/2007 | Myrman et al. |
| 7,278,843 B2 | 10/2007 | Feldstein et al. |
| 7,279,457 B2 | 10/2007 | Pohl et al. |
| 7,284,553 B2 | 10/2007 | Hochrainer |
| D557,799 S | 12/2007 | Greenhalgh et al. |
| 7,305,986 B1 | 12/2007 | Steiner |
| 7,306,787 B2 | 12/2007 | Tarara et al. |
| D560,793 S | 1/2008 | Pearl et al. |
| 7,314,859 B2 | 1/2008 | Green et al. |
| 7,316,748 B2 | 1/2008 | Li et al. |
| 7,331,340 B2 | 2/2008 | Barney |
| 7,334,577 B2 | 2/2008 | Gumaste et al. |
| 7,344,734 B2 | 3/2008 | Heijerman et al. |
| 7,368,102 B2 | 5/2008 | Tarara et al. |
| 7,373,938 B2 | 5/2008 | Nichols et al. |
| 7,377,277 B2 | 5/2008 | Hickey et al. |
| 7,387,122 B2 | 6/2008 | Nishibayashi et al. |
| 7,399,528 B2 | 7/2008 | Caponetti et al. |
| 7,401,713 B2 | 7/2008 | Ede et al. |
| 7,402,564 B1 | 7/2008 | Schteingart et al. |
| 7,414,720 B2 | 8/2008 | Wachtel et al. |
| D577,815 S | 9/2008 | Gokhale et al. |
| 7,422,013 B2 | 9/2008 | Burr et al. |
| D579,549 S | 10/2008 | Birath et al. |
| 7,448,375 B2 | 11/2008 | Gonda et al. |
| 7,448,379 B2 | 11/2008 | Yamashita et al. |
| 7,451,761 B2 | 11/2008 | Hickey et al. |
| 7,453,556 B2 | 11/2008 | Hochrainer et al. |
| D583,463 S | 12/2008 | Wood et al. |
| 7,461,653 B2 | 12/2008 | Oliva |
| 7,462,367 B2 | 12/2008 | Schmidt et al. |
| 7,464,706 B2 | 12/2008 | Steiner et al. |
| 7,469,696 B2 | 12/2008 | Yang et al. |
| 7,500,479 B2 | 3/2009 | Nichols et al. |
| 7,503,324 B2 | 3/2009 | Barney et al. |
| 7,504,538 B2 | 3/2009 | Chang et al. |
| 7,517,874 B2 | 4/2009 | Beckett et al. |
| 7,520,278 B2 | 4/2009 | Crowder et al. |
| 7,521,069 B2 | 4/2009 | Patton et al. |
| 7,533,668 B1 | 5/2009 | Widerstrom |
| D594,753 S | 6/2009 | Eadicicco et al. |
| 7,556,798 B2 | 7/2009 | Edwards et al. |
| 7,559,322 B2 | 7/2009 | Foley et al. |
| D597,418 S | 8/2009 | Stojek |
| D597,657 S | 8/2009 | Kinsey et al. |
| D598,785 S | 8/2009 | Stojek |
| 7,584,846 B2 | 9/2009 | Senter |
| 7,598,222 B2 | 10/2009 | Prouty, Jr. et al. |
| D604,832 S | 11/2009 | Smutney |
| D604,833 S | 11/2009 | Polidoro |
| D605,752 S | 12/2009 | Polidoro |
| D605,753 S | 12/2009 | Smutney |
| 7,625,865 B2 | 12/2009 | Colombo |
| 7,648,960 B2 | 1/2010 | Steiner et al. |
| D613,849 S | 4/2010 | Smutney |
| D614,045 S | 4/2010 | Gaudenzi et al. |
| D614,760 S | 4/2010 | Smutney et al. |
| 7,694,676 B2 | 4/2010 | Wachtel |
| 7,708,014 B2 | 5/2010 | Yamashita et al. |
| 7,709,639 B2 | 5/2010 | Stevenson |
| 7,713,937 B2 | 5/2010 | Schteingart et al. |
| 7,727,963 B2 | 6/2010 | Schteingart et al. |
| 7,735,485 B2 | 6/2010 | Yamashita et al. |
| D620,812 S | 8/2010 | Gaudenzi et al. |
| 7,794,754 B2 | 9/2010 | Feldstein et al. |
| 7,799,344 B2 | 9/2010 | Oberg |
| 7,803,404 B2 | 9/2010 | Hokenson |
| 7,820,676 B2 | 10/2010 | Leone-Bay et al. |
| D628,090 S | 11/2010 | Stuiber et al. |
| 7,833,549 B2 | 11/2010 | Steiner et al. |
| 7,833,550 B2 | 11/2010 | Steiner et al. |
| 7,842,662 B2 | 11/2010 | Schteingart et al. |
| D629,505 S | 12/2010 | Adamo |
| D629,506 S | 12/2010 | Adamo |
| D629,886 S | 12/2010 | Adamo |
| D629,887 S | 12/2010 | Adamo |
| D629,888 S | 12/2010 | Adamo |
| D635,241 S | 3/2011 | McLean |

(56) References Cited

U.S. PATENT DOCUMENTS

| | | |
|---|---|---|
| D635,242 S | 3/2011 | Adamo |
| D635,243 S | 3/2011 | Kinsey |
| 7,913,688 B2 | 3/2011 | Cross |
| D636,867 S | 4/2011 | Polidoro et al. |
| D636,868 S | 4/2011 | Kinsey et al. |
| D636,869 S | 4/2011 | Laurenzi et al. |
| 7,919,119 B2 | 4/2011 | Straub et al. |
| 7,943,178 B2 | 5/2011 | Steiner et al. |
| 7,943,572 B2 | 5/2011 | Cheatham et al. |
| 7,954,491 B2 | 6/2011 | Hrkach |
| 7,959,609 B2 | 6/2011 | Gaydos et al. |
| D641,076 S | 7/2011 | Grunstad et al. |
| D643,308 S | 8/2011 | Bergey |
| D645,954 S | 9/2011 | Hately |
| D647,195 S | 10/2011 | Clarke et al. |
| D647,196 S | 10/2011 | Clarke et al. |
| 8,037,880 B2 | 10/2011 | Zhu et al. |
| 8,037,881 B2 | 10/2011 | Pentafragas |
| 8,039,431 B2 | 10/2011 | Wilson et al. |
| 8,047,203 B2 | 11/2011 | Young et al. |
| D652,322 S | 1/2012 | Stuiber et al. |
| 8,109,267 B2 | 2/2012 | Villax et al. |
| 8,119,593 B2 | 2/2012 | Richardson |
| D655,622 S | 3/2012 | Sadler et al. |
| 8,133,514 B2 | 3/2012 | Milstein |
| 8,146,588 B2 | 4/2012 | Steiner et al. |
| 8,156,936 B2 | 4/2012 | Steiner et al. |
| D659,020 S | 5/2012 | Kemner |
| D659,022 S | 5/2012 | Kemner |
| 8,166,970 B2 | 5/2012 | Poole et al. |
| 8,172,817 B2 | 5/2012 | Michaels et al. |
| 8,196,576 B2 | 6/2012 | Kriksunov et al. |
| 8,201,555 B2 | 6/2012 | Chawla |
| 8,202,992 B2 | 6/2012 | Stevenson |
| D664,640 S | 7/2012 | Smutney et al. |
| 8,215,300 B2 | 7/2012 | Steiner et al. |
| 8,217,007 B1 | 7/2012 | Schteingart et al. |
| 8,227,409 B2 | 7/2012 | Kraft |
| 8,236,766 B2 | 8/2012 | Schteingart et al. |
| 8,252,916 B2 | 8/2012 | Simard et al. |
| 8,258,095 B2 | 9/2012 | Boss et al. |
| 8,278,308 B2 | 10/2012 | Leone-Bay et al. |
| 8,293,869 B2 | 10/2012 | Bossard |
| 8,314,106 B2 | 11/2012 | Kraft |
| D671,842 S | 12/2012 | Bergey |
| D674,893 S | 1/2013 | Kinsey et al. |
| 8,372,804 B2 | 2/2013 | Richardson |
| 8,377,869 B2 | 2/2013 | Richardson |
| 8,389,470 B2 | 3/2013 | Steiner |
| 8,394,414 B2 | 3/2013 | Steiner et al. |
| 8,408,200 B2 | 4/2013 | Clark et al. |
| 8,420,604 B2 | 4/2013 | Hokenson |
| 8,424,518 B2 | 4/2013 | Smutney |
| 8,485,180 B2 | 7/2013 | Smutney et al. |
| 8,486,894 B2 | 7/2013 | Schteingart et al. |
| 8,499,757 B2 | 8/2013 | Smutney |
| 8,512,932 B2 | 8/2013 | Wilson et al. |
| 8,522,775 B2 | 9/2013 | Malhotra et al. |
| 8,536,131 B2 | 9/2013 | Schteingart et al. |
| 8,538,707 B2 | 9/2013 | Adamo et al. |
| 8,539,946 B2 | 9/2013 | Esteve et al. |
| 8,551,528 B2 | 10/2013 | Grant et al. |
| 8,563,101 B2 | 10/2013 | Spallek |
| 8,636,001 B2 | 1/2014 | Smutney |
| 8,642,548 B2 | 2/2014 | Richardson et al. |
| 8,671,937 B2 | 3/2014 | Steiner et al. |
| 8,677,992 B2 | 3/2014 | Villax |
| 8,763,606 B2 | 7/2014 | Mosier et al. |
| 8,778,403 B2 | 7/2014 | Grant et al. |
| 8,783,249 B2 | 7/2014 | Trent et al. |
| 8,808,786 B2 | 8/2014 | Jinks et al. |
| 8,820,324 B2 | 9/2014 | Smith et al. |
| 8,909,487 B2 | 12/2014 | Adamo et al. |
| 8,925,726 B2 | 1/2015 | Bergey |
| 9,041,925 B2 | 5/2015 | Adamo et al. |
| 9,138,407 B2 | 9/2015 | Caponetti et al. |
| 2001/0020147 A1 | 9/2001 | Staniforth et al. |
| 2001/0039442 A1 | 11/2001 | Gorge et al. |
| 2002/0000225 A1 | 1/2002 | Schuler et al. |
| 2002/0033177 A1 | 3/2002 | Ohki et al. |
| 2002/0052381 A1 | 5/2002 | Bar-Or et al. |
| 2002/0053344 A1 | 5/2002 | Davies et al. |
| 2002/0053347 A1 | 5/2002 | Ziaee |
| 2002/0065239 A1 | 5/2002 | Caplan et al. |
| 2002/0088462 A1 | 7/2002 | Genova et al. |
| 2002/0101590 A1 | 8/2002 | Shimaoka |
| 2002/0144680 A1 | 10/2002 | Nilsson et al. |
| 2002/0161001 A1 | 10/2002 | Kanstrup et al. |
| 2003/0000524 A1 | 1/2003 | Andersson et al. |
| 2003/0010794 A1 | 1/2003 | Herdtle et al. |
| 2003/0013641 A1 | 1/2003 | Steiner et al. |
| 2003/0017211 A1 | 1/2003 | Steiner |
| 2003/0053960 A1 | 3/2003 | Heijerman et al. |
| 2003/0064097 A1 | 4/2003 | Patel et al. |
| 2003/0068378 A1 | 4/2003 | Chen et al. |
| 2003/0099636 A1 | 5/2003 | Epshtein et al. |
| 2003/0136405 A1 | 7/2003 | Goede et al. |
| 2003/0194420 A1 | 10/2003 | Holl et al. |
| 2003/0235538 A1 | 12/2003 | Zirenberg |
| 2004/0024180 A1 | 2/2004 | Drauz |
| 2004/0025875 A1 | 2/2004 | Reber et al. |
| 2004/0034014 A1 | 2/2004 | Kanstrup et al. |
| 2004/0038865 A1 | 2/2004 | Gelber et al. |
| 2004/0053819 A1 | 3/2004 | Dodd et al. |
| 2004/0062722 A1 | 4/2004 | Gonda et al. |
| 2004/0076588 A1 | 4/2004 | Batycky et al. |
| 2004/0077528 A1 | 4/2004 | Steiner et al. |
| 2004/0096403 A1 | 5/2004 | Steiner |
| 2004/0107963 A1 | 6/2004 | Finlay et al. |
| 2004/0121964 A1 | 6/2004 | Madar et al. |
| 2004/0138099 A1 | 7/2004 | Draeger |
| 2004/0151059 A1 | 8/2004 | Robert, II et al. |
| 2004/0151774 A1 | 8/2004 | Pauletti et al. |
| 2004/0157928 A1 | 8/2004 | Kim et al. |
| 2004/0163648 A1 | 8/2004 | Burton |
| 2004/0182387 A1 | 9/2004 | Steiner et al. |
| 2004/0187869 A1 | 9/2004 | Bjorndal et al. |
| 2004/0204439 A1 | 10/2004 | Staniforth et al. |
| 2004/0204440 A1 | 10/2004 | Staniforth et al. |
| 2004/0211419 A1 | 10/2004 | Eason et al. |
| 2004/0234615 A1 | 11/2004 | Sabetsky |
| 2004/0234616 A1 | 11/2004 | Sabetsky |
| 2004/0241232 A1 | 12/2004 | Brown et al. |
| 2004/0247628 A1 | 12/2004 | Lintz et al. |
| 2004/0250812 A1 | 12/2004 | Davies et al. |
| 2005/0000518 A1 | 1/2005 | Dunkley et al. |
| 2005/0039743 A1 | 2/2005 | Taylor |
| 2005/0043228 A1 | 2/2005 | DeFelippis et al. |
| 2005/0043247 A1 | 2/2005 | Trunk et al. |
| 2005/0056281 A1 | 3/2005 | Snow |
| 2005/0070469 A1 | 3/2005 | Bloom |
| 2005/0080000 A1 | 4/2005 | Thurow et al. |
| 2005/0119604 A1 | 6/2005 | Bonney et al. |
| 2005/0124644 A1 | 6/2005 | Nilsson et al. |
| 2005/0147581 A1 | 7/2005 | Zamiri et al. |
| 2005/0153874 A1 | 7/2005 | Cheatham et al. |
| 2005/0155601 A1 | 7/2005 | Steiner et al. |
| 2005/0183723 A1 | 8/2005 | Pinon et al. |
| 2005/0187749 A1 | 8/2005 | Singley |
| 2005/0214251 A1 | 9/2005 | Pohl et al. |
| 2005/0252508 A1 | 11/2005 | Koerner |
| 2005/0265927 A1 | 12/2005 | Lee |
| 2005/0274378 A1 | 12/2005 | Bonney et al. |
| 2006/0000469 A1 | 1/2006 | Tseng |
| 2006/0003316 A1 | 1/2006 | Simard et al. |
| 2006/0040953 A1 | 2/2006 | Leone-Bay et al. |
| 2006/0041133 A1 | 2/2006 | Stevenson et al. |
| 2006/0099269 A1 | 5/2006 | Cheatham et al. |
| 2006/0120969 A1 | 6/2006 | Nilsson et al. |
| 2006/0153778 A1 | 7/2006 | Gelber et al. |
| 2006/0160722 A1 | 7/2006 | Green et al. |
| 2006/0165756 A1 | 7/2006 | Catani et al. |
| 2006/0239933 A1 | 10/2006 | Nilsson et al. |
| 2006/0239934 A1 | 10/2006 | Cheatham et al. |

(56) References Cited

U.S. PATENT DOCUMENTS

| | | |
|---|---|---|
| 2006/0243275 A1 | 11/2006 | Ruckdeschel et al. |
| 2006/0249419 A1 | 11/2006 | Taylor et al. |
| 2006/0260777 A1 | 11/2006 | Rashba-Step et al. |
| 2006/0283758 A1 | 12/2006 | Pasbrig |
| 2007/0006876 A1 | 1/2007 | Finlay et al. |
| 2007/0017506 A1 | 1/2007 | Bell et al. |
| 2007/0020191 A1 | 1/2007 | Boss et al. |
| 2007/0027063 A1 | 2/2007 | Boss et al. |
| 2007/0044793 A1 | 3/2007 | Kleinstreuer et al. |
| 2007/0049576 A1 | 3/2007 | Barlow et al. |
| 2007/0059373 A1 | 3/2007 | Oberg |
| 2007/0059374 A1 | 3/2007 | Hokenson et al. |
| 2007/0074989 A1 | 4/2007 | Merboth et al. |
| 2007/0077219 A1 | 4/2007 | Fahl et al. |
| 2007/0086952 A1 | 4/2007 | Steiner |
| 2007/0099454 A1 | 5/2007 | Gordon |
| 2007/0125375 A1 | 6/2007 | Finlay et al. |
| 2007/0128193 A1 | 6/2007 | O'Neil et al. |
| 2007/0151562 A1 | 7/2007 | Jones |
| 2007/0191462 A1 | 8/2007 | Hettiarachchi |
| 2007/0196503 A1 | 8/2007 | Wilson et al. |
| 2007/0207958 A1 | 9/2007 | Bridon et al. |
| 2007/0225587 A1 | 9/2007 | Burnell et al. |
| 2007/0235029 A1 | 10/2007 | Zhu et al. |
| 2007/0240708 A1 | 10/2007 | Schuckmann |
| 2007/0272763 A1 | 11/2007 | Dunne et al. |
| 2007/0277820 A1 | 12/2007 | Crowder et al. |
| 2007/0277821 A1 | 12/2007 | Oliva et al. |
| 2007/0295332 A1 | 12/2007 | Ziegler |
| 2007/0299074 A1 | 12/2007 | Netz et al. |
| 2008/0008764 A1 | 1/2008 | Milstein |
| 2008/0015457 A1 | 1/2008 | Silva |
| 2008/0047550 A2 | 2/2008 | Steiner et al. |
| 2008/0066739 A1 | 3/2008 | LeMahieu et al. |
| 2008/0108554 A1 | 5/2008 | Jackson et al. |
| 2008/0108574 A1 | 5/2008 | Barlow et al. |
| 2008/0115785 A1 | 5/2008 | Eason et al. |
| 2008/0127970 A1 | 6/2008 | Steiner et al. |
| 2008/0127971 A1 | 6/2008 | King et al. |
| 2008/0127974 A1 | 6/2008 | Lastow |
| 2008/0168987 A1 | 7/2008 | Denny et al. |
| 2008/0190424 A1 | 8/2008 | Lucking et al. |
| 2008/0197044 A1 | 8/2008 | Hickey et al. |
| 2008/0216824 A1 | 9/2008 | Ooida |
| 2008/0217199 A1 | 9/2008 | Burress et al. |
| 2008/0255468 A1 | 10/2008 | Derchak et al. |
| 2008/0260838 A1 | 10/2008 | Hokenson et al. |
| 2008/0260840 A1 | 10/2008 | Alessi |
| 2008/0295833 A1 | 12/2008 | Rohrschneider et al. |
| 2008/0314384 A1 | 12/2008 | Harris et al. |
| 2008/0319333 A1 | 12/2008 | Gavish et al. |
| 2009/0025720 A1 | 1/2009 | Chen |
| 2009/0068274 A1 | 3/2009 | Edwards et al. |
| 2009/0084379 A1 | 4/2009 | Goeckner et al. |
| 2009/0084380 A1 | 4/2009 | Gieschen et al. |
| 2009/0134051 A1 | 5/2009 | Rapp et al. |
| 2009/0149727 A1 | 6/2009 | Truitt et al. |
| 2009/0151720 A1 | 6/2009 | Inoue et al. |
| 2009/0178676 A1 | 7/2009 | Villax et al. |
| 2009/0205657 A1 | 8/2009 | Barney et al. |
| 2009/0209502 A1 | 8/2009 | Haeberlin et al. |
| 2009/0232891 A1 | 9/2009 | Gelber et al. |
| 2009/0241949 A1 | 10/2009 | Smutney |
| 2009/0250058 A1 | 10/2009 | Lastow |
| 2009/0258818 A1 | 10/2009 | Surolia et al. |
| 2009/0314292 A1 | 12/2009 | Overfield |
| 2009/0320837 A1 | 12/2009 | Smith et al. |
| 2010/0012120 A1 | 1/2010 | Herder |
| 2010/0086609 A1 | 4/2010 | Steiner et al. |
| 2010/0113363 A1 | 5/2010 | Holst et al. |
| 2010/0163042 A1 | 7/2010 | Bhowmick et al. |
| 2010/0180894 A1 | 7/2010 | Jones et al. |
| 2010/0181225 A1 | 7/2010 | Spallek et al. |
| 2010/0190701 A1 | 7/2010 | Day et al. |
| 2010/0193380 A1 | 8/2010 | Sullivan et al. |
| 2010/0197565 A1 | 8/2010 | Smutney et al. |
| 2010/0212667 A1 | 8/2010 | Smith et al. |
| 2010/0235116 A1 | 9/2010 | Adamo et al. |
| 2010/0238457 A1 | 9/2010 | Adamo et al. |
| 2010/0278924 A1 | 11/2010 | Oberg |
| 2010/0288276 A1 | 11/2010 | Ganderton et al. |
| 2010/0326438 A1 | 12/2010 | Dunne |
| 2011/0000482 A1 | 1/2011 | Gumaste et al. |
| 2011/0003004 A1 | 1/2011 | Hokenson |
| 2011/0011394 A1 | 1/2011 | Edwards et al. |
| 2011/0083667 A1 | 4/2011 | Briant |
| 2011/0158935 A1 | 6/2011 | Kraft |
| 2011/0183901 A1 | 7/2011 | Cheatham |
| 2012/0014999 A1 | 1/2012 | Grant et al. |
| 2012/0040899 A1 | 2/2012 | Costello |
| 2012/0071510 A1 | 3/2012 | Leone-Bay et al. |
| 2012/0094905 A1 | 4/2012 | Costello |
| 2012/0115777 A1 | 5/2012 | Richardson |
| 2012/0122775 A1 | 5/2012 | Boss et al. |
| 2012/0160241 A1 | 6/2012 | Oliva |
| 2012/0164186 A1 | 6/2012 | Grant et al. |
| 2012/0178935 A1 | 7/2012 | Stevenson |
| 2012/0192865 A1 | 8/2012 | Steiner et al. |
| 2012/0207913 A1 | 8/2012 | Smyth |
| 2012/0240929 A1 | 9/2012 | Steiner et al. |
| 2012/0247235 A1 | 10/2012 | Adamo et al. |
| 2012/0247465 A1 | 10/2012 | Wachtel |
| 2012/0328676 A1 | 12/2012 | Leone-Bay et al. |
| 2013/0012710 A1 | 1/2013 | Freeman et al. |
| 2013/0053309 A1 | 2/2013 | Kraft |
| 2013/0104887 A1 | 5/2013 | Smutney et al. |
| 2013/0118491 A1 | 5/2013 | Richardson et al. |
| 2013/0125886 A1 | 5/2013 | Richardson et al. |
| 2013/0143801 A1 | 6/2013 | Steiner et al. |
| 2013/0189365 A1 | 7/2013 | Hokenson |
| 2013/0199527 A1 | 8/2013 | Smutney et al. |
| 2013/0289278 A1 | 10/2013 | Kraft |
| 2013/0291866 A1 | 11/2013 | Smutney |
| 2013/0291867 A1 | 11/2013 | Smutney |
| 2013/0303445 A1 | 11/2013 | Wilson et al. |
| 2013/0338065 A1 | 12/2013 | Smutney |
| 2014/0007873 A1 | 1/2014 | Smutney |
| 2014/0014106 A1 | 1/2014 | Smutney |
| 2014/0083421 A1 | 3/2014 | Smutney |
| 2014/0096771 A1 | 4/2014 | Remmelgas et al. |
| 2014/0100158 A1 | 4/2014 | Richardson et al. |
| 2014/0187490 A1 | 7/2014 | Richardson et al. |
| 2014/0199398 A1 | 7/2014 | Grant et al. |
| 2014/0227359 A1 | 8/2014 | Leone-Bay et al. |
| 2014/0243530 A1 | 8/2014 | Stevenson et al. |
| 2014/0271888 A1 | 9/2014 | Grant et al. |
| 2014/0290654 A1 | 10/2014 | Poole et al. |
| 2014/0302151 A1 | 10/2014 | Leone-Bay et al. |
| 2014/0308358 A1 | 10/2014 | Oberg et al. |
| 2014/0315953 A1 | 10/2014 | Leone-Bay et al. |
| 2015/0031609 A1 | 1/2015 | Steiner et al. |
| 2015/0045295 A1 | 2/2015 | Smutney et al. |
| 2015/0052977 A1 | 2/2015 | Adamo et al. |
| 2015/0065422 A1 | 3/2015 | Kraft |
| 2015/0080298 A1 | 3/2015 | Costello et al. |
| 2015/0108023 A1 | 4/2015 | Bergey |
| 2015/0122258 A1 | 5/2015 | Steiner et al. |
| 2015/0150980 A1 | 6/2015 | Leone-Bay et al. |
| 2015/0174210 A1 | 6/2015 | Boss et al. |
| 2015/0196724 A1 | 7/2015 | Adamo et al. |
| 2015/0226656 A1 | 8/2015 | Adamo et al. |
| 2015/0231067 A1 | 8/2015 | Mann |
| 2015/0246188 A1 | 9/2015 | Steiner et al. |
| 2015/0283069 A1 | 10/2015 | Smutney et al. |
| 2015/0283213 A1 | 10/2015 | Costello et al. |
| 2015/0290132 A1 | 10/2015 | Gelber et al. |

FOREIGN PATENT DOCUMENTS

| | | |
|---|---|---|
| CN | 101851213 | 10/2010 |
| DE | 2840442 C2 | 2/1982 |
| DE | 3639836 A1 | 6/1988 |
| DE | 19519840 A1 | 12/1996 |
| EP | 69715 | 1/1983 |

(56) References Cited

FOREIGN PATENT DOCUMENTS

| | | |
|---|---|---|
| EP | 122036 | 10/1984 |
| EP | 143524 | 6/1985 |
| EP | 180543 | 5/1986 |
| EP | 220958 | 5/1987 |
| EP | 237507 | 8/1987 |
| EP | 257915 | 2/1988 |
| EP | 308637 A1 | 3/1989 |
| EP | 360340 | 3/1990 |
| EP | 364235 | 4/1990 |
| EP | 387222 A | 9/1990 |
| EP | 388621 A | 9/1990 |
| EP | 606486 | 12/1993 |
| EP | 581473 A1 | 2/1994 |
| EP | 655237 | 5/1995 |
| EP | 666085 A1 | 8/1995 |
| EP | 748213 | 12/1996 |
| EP | 558879 B1 | 5/1997 |
| EP | 844007 | 12/1998 |
| EP | 1060741 A1 | 12/2000 |
| EP | 1114644 | 7/2001 |
| EP | 640354 B1 | 12/2001 |
| EP | 1364967 | 11/2003 |
| EP | 825885 B1 | 3/2004 |
| EP | 96911738 | 6/2004 |
| EP | 1598066 | 11/2005 |
| EP | 833652 B1 | 2/2008 |
| EP | 1923087 A2 | 5/2008 |
| EP | 2060268 A1 | 5/2009 |
| EP | 2314298 A1 | 4/2011 |
| GB | 475440 A | 11/1937 |
| GB | 716815 | 10/1954 |
| GB | 2072536 A | 10/1981 |
| GB | 2148841 A | 6/1985 |
| GB | 2240337 | 7/1991 |
| GB | 2253200 A | 9/1992 |
| GB | 2262452 | 6/1993 |
| GB | 2398065 A | 8/2004 |
| JP | 63-020301 | 1/1988 |
| JP | 2115154 A | 4/1990 |
| JP | 2-149545 | 2/1992 |
| JP | H07-041428 | 2/1995 |
| JP | 09-208485 | 8/1997 |
| JP | 10234827 A | 9/1998 |
| JP | 2002322294 | 11/2002 |
| JP | 2003-503420 | 1/2003 |
| JP | 2004-121061 | 4/2004 |
| JP | 2006-280620 A | 10/2006 |
| JP | 2007-061281 | 3/2007 |
| TW | 200505517 A | 2/2005 |
| WO | 90/13285 | 11/1990 |
| WO | 91/04011 | 4/1991 |
| WO | 91/06287 | 5/1991 |
| WO | 91/16038 | 10/1991 |
| WO | 91/16882 | 11/1991 |
| WO | 91/19524 | 12/1991 |
| WO | 92/04069 | 3/1992 |
| WO | 92/08509 | 5/1992 |
| WO | 93/02712 | 2/1993 |
| WO | 93/14110 | 7/1993 |
| WO | 93/17728 | 9/1993 |
| WO | 93/18754 A1 | 9/1993 |
| WO | 94/00291 | 1/1994 |
| WO | 94/08552 | 4/1994 |
| WO | 94/08599 | 4/1994 |
| WO | 94/19041 | 9/1994 |
| WO | 94/23702 | 10/1994 |
| WO | 94/25005 A1 | 11/1994 |
| WO | 95/00127 A1 | 1/1995 |
| WO | 95/05208 | 2/1995 |
| WO | 95/11666 | 5/1995 |
| WO | 95/24183 A1 | 9/1995 |
| WO | 95/31979 | 11/1995 |
| WO | 95/34294 | 12/1995 |
| WO | 96/01105 | 1/1996 |
| WO | 96/05810 | 2/1996 |
| WO | 96/13250 | 5/1996 |
| WO | 96/22802 A | 8/1996 |
| WO | 96/27386 A1 | 9/1996 |
| WO | 96/32149 | 10/1996 |
| WO | 96/36314 | 11/1996 |
| WO | 96/36317 A1 | 11/1996 |
| WO | 96/40206 A1 | 12/1996 |
| WO | 97/01365 | 1/1997 |
| WO | 97/04747 | 2/1997 |
| WO | 97/25086 A2 | 7/1997 |
| WO | 97/30743 | 8/1997 |
| WO | 97/35562 A1 | 10/1997 |
| WO | 97/46206 | 12/1997 |
| WO | 97/49386 | 12/1997 |
| WO | 98/26827 A1 | 6/1998 |
| WO | 98/39043 | 9/1998 |
| WO | 98/41255 A2 | 9/1998 |
| WO | 98/43615 | 10/1998 |
| WO | 99/14239 A1 | 3/1999 |
| WO | 99/18939 A1 | 4/1999 |
| WO | 99/32510 A1 | 7/1999 |
| WO | 99/33862 | 7/1999 |
| WO | 99/52506 | 10/1999 |
| WO | 00/12116 | 3/2000 |
| WO | 00/33811 A2 | 6/2000 |
| WO | 00/59476 A1 | 10/2000 |
| WO | 00/71154 A2 | 11/2000 |
| WO | 01/00654 | 1/2001 |
| WO | 01/81321 A | 1/2001 |
| WO | 01/07107 | 2/2001 |
| WO | 01/49274 A2 | 7/2001 |
| WO | 01/51071 | 7/2001 |
| WO | 01/52813 A1 | 7/2001 |
| WO | 01/66064 | 9/2001 |
| WO | 01/68169 | 9/2001 |
| WO | 01/97886 A1 | 12/2001 |
| WO | 02/11676 | 2/2002 |
| WO | 02/12201 A1 | 2/2002 |
| WO | 02/47659 A2 | 6/2002 |
| WO | 02/058735 | 8/2002 |
| WO | 02/059574 A1 | 8/2002 |
| WO | 02/067995 A1 | 9/2002 |
| WO | 02/085281 | 10/2002 |
| WO | 02/098348 | 12/2002 |
| WO | 02/102444 | 12/2002 |
| WO | 03/000202 | 1/2003 |
| WO | 03/022304 A1 | 3/2003 |
| WO | 03/055547 A1 | 7/2003 |
| WO | 03/057170 | 7/2003 |
| WO | 03/061578 A2 | 7/2003 |
| WO | 03/072195 A2 | 9/2003 |
| WO | 03/080149 A2 | 10/2003 |
| WO | 03/086345 | 10/2003 |
| WO | 03/094951 | 11/2003 |
| WO | 2004/012672 | 2/2004 |
| WO | 2004/012720 | 2/2004 |
| WO | 2004/033010 | 4/2004 |
| WO | 2004/035121 | 4/2004 |
| WO | 2004/041338 | 5/2004 |
| WO | 2004/050152 | 6/2004 |
| WO | 2004/054647 A1 | 7/2004 |
| WO | 2004/056314 | 7/2004 |
| WO | 2004/060458 | 7/2004 |
| WO | 2004/064862 | 8/2004 |
| WO | 2004/075919 | 9/2004 |
| WO | 2004/080401 | 9/2004 |
| WO | 2004/080482 | 9/2004 |
| WO | 2004/103304 A2 | 12/2004 |
| WO | 2005/020964 | 3/2005 |
| WO | 2005/023348 A | 3/2005 |
| WO | 2005/028699 A1 | 3/2005 |
| WO | 2005/067964 | 7/2005 |
| WO | 2005/081977 A2 | 9/2005 |
| WO | 2005/089722 | 9/2005 |
| WO | 2005/089843 | 9/2005 |
| WO | 2005/102428 A1 | 11/2005 |
| WO | 2005/102429 | 11/2005 |
| WO | 2005/113042 A1 | 12/2005 |
| WO | 2005/113043 | 12/2005 |

(56) References Cited

FOREIGN PATENT DOCUMENTS

| | | |
|---|---|---|
| WO | 2005/120616 | 12/2005 |
| WO | 2006/010248 | 2/2006 |
| WO | 2006/017688 A2 | 2/2006 |
| WO | 2006/023849 | 3/2006 |
| WO | 2006/023943 | 3/2006 |
| WO | 2006/023944 | 3/2006 |
| WO | 2006/037636 | 4/2006 |
| WO | 2006/059939 | 6/2006 |
| WO | 2006/061637 A2 | 6/2006 |
| WO | 2006/086107 A2 | 8/2006 |
| WO | 2006/090149 | 8/2006 |
| WO | 2006/105501 | 10/2006 |
| WO | 2007/007110 A1 | 1/2007 |
| WO | 2007/016600 A2 | 2/2007 |
| WO | 2007/019229 | 2/2007 |
| WO | 2007/024953 A1 | 3/2007 |
| WO | 2007/030706 | 3/2007 |
| WO | 2007/033316 | 3/2007 |
| WO | 2007/033372 A2 | 3/2007 |
| WO | 2007/042822 | 4/2007 |
| WO | 2007/068896 | 6/2007 |
| WO | 2007/075534 A2 | 7/2007 |
| WO | 2007/093310 | 8/2007 |
| WO | 2007/098500 | 8/2007 |
| WO | 2007/100535 | 9/2007 |
| WO | 2007/118342 | 10/2007 |
| WO | 2007/118343 A1 | 10/2007 |
| WO | 2007/121411 | 10/2007 |
| WO | 2007/132217 | 11/2007 |
| WO | 2007/144607 | 12/2007 |
| WO | 2007/144614 | 12/2007 |
| WO | 2008/001744 | 1/2008 |
| WO | 2008/008021 | 1/2008 |
| WO | 2008/014613 A1 | 2/2008 |
| WO | 2008/020217 | 2/2008 |
| WO | 2008/060684 A2 | 5/2008 |
| WO | 2008/092864 | 8/2008 |
| WO | 2008/110809 | 9/2008 |
| WO | 2009/005546 A1 | 1/2009 |
| WO | 2009/008001 A2 | 1/2009 |
| WO | 2009/009013 A2 | 1/2009 |
| WO | 2009/047281 A1 | 4/2009 |
| WO | 2009/055030 | 4/2009 |
| WO | 2009/055740 | 4/2009 |
| WO | 2009/055742 | 4/2009 |
| WO | 2009/095684 A1 | 8/2009 |
| WO | 2009/121020 A1 | 10/2009 |
| WO | 2009/140587 A1 | 11/2009 |
| WO | 2009/152477 A2 | 12/2009 |
| WO | 2009/155581 A1 | 12/2009 |
| WO | 2010/021879 A2 | 2/2010 |
| WO | 2010/078373 A1 | 7/2010 |
| WO | 2010/080964 | 7/2010 |
| WO | 2010/102148 | 9/2010 |
| WO | 2010/105094 A1 | 9/2010 |
| WO | 2010/108046 A1 | 9/2010 |
| WO | 2010/125103 A1 | 11/2010 |
| WO | 2010/144785 A2 | 12/2010 |
| WO | 2010/144789 | 12/2010 |
| WO | 2011/017554 A2 | 2/2011 |
| WO | 2011/056889 A1 | 5/2011 |
| WO | 2011/163272 | 12/2011 |
| WO | 2012/064892 A1 | 5/2012 |
| WO | 2012/135765 | 10/2012 |
| WO | 2012/174472 A1 | 12/2012 |
| WO | 2012/174556 A1 | 12/2012 |
| WO | 2013/063160 A1 | 5/2013 |
| WO | 2014/012069 A2 | 1/2014 |
| WO | 2014/036323 A1 | 3/2014 |
| WO | 2014/066856 A1 | 5/2014 |
| WO | 2014/144895 A1 | 9/2014 |
| WO | 2015/010092 A1 | 1/2015 |
| WO | 2015/021064 A1 | 2/2015 |
| WO | 2015/148905 A1 | 10/2015 |

OTHER PUBLICATIONS

Vanderah et al., FE200041 (D-Phe-D-Phe-D-Nle-D-Arg-NH2): A peripheral efficacious k opioid agonist with unprecedented selectivity. The Journal of Pharmacology and Experimental Therapeutics, vol. 310, No. 1, pp. 326-333 (2004).

Standl et al. "Good Glycemic Control With Flexibility in Timing of Basal Insulin Supply." Diabetes Care, vol. 28, No. 2, Feb. 2005.

Stanley et al. "Gastrointestinal satiety signals III. Glucagon-like peptide 1, oxyntomodulin, peptide YY and pacretic peptide. " Am J Physiol Gastrointest Liver Physiol 286:G693, 2004.

Steinberg et al. "A new approach to the safety assessment of pharmaceutical excipients." Reg Toxicol Pharmacol 24:149, 1996.

Steiner et al. "A novel glucagon delivery system for the management of hyperinsulinemia." Diabetes 49 Supplement 1, Abstract 1545-PO, A368, 2000.

Steiner et al. "Bioavailability and pharmacokinetic properties of inhaled dry powder Technosphere®/Insulin." Diabetes 49 Supplement, May 2000, A126.

Steiner et al. "Technosphere®, a novel drug delivery system for oral administration of calcitonin." Pharmaceutical Res 11:S299, 1994.

Steiner et al. Technosphere(TM)/Insulin—proof of concept study with a new insulin formulation for pulmonary delivery. Exp Clin Endocrinol Diabetes, 110:17-21, 2002.

Steiner, K. et al. "The relative importance of first- and second-phase insulin secretion in countering the action of glucagon on glucose turnover in the conscious dog." Diabetes 31:964-972, 1982.

Steiner S, Rave K, Heise T, et al. Pharmacokinetic properties and bioavailablility of inhaled drug powder Technosphere™/insulin. Exp Clin Endocrinol Diabetes 2000; 108:S161.

Steiner S, Rave K, Heise T, et al. Technosphere™/insulin: Bioavailability and pharmacokinetic properties in healthy volunteers. Diabetologia 2000;43:Abstract 511-P.

Steiner SS, Burrell BB, Feldstein R, et Al. Pulmonary delivery of Technosphere™/insulin: Increased bioefficacy and bioavailability in clinical trials using the PDC Medtone™ inhaler. Proceed Int'l Symp Control Rel Bioact Mater 2000; 27:1000-1001.

Stowell et al. "Development of GLP-1 Technosphere(TM) powder: an inhaled GLP-1 product." Diabetes Technology Meeting, San Francisco, Oct. 2007.

Strack "Inhaled Human Insulin." Drugs of Today 2006, 42 (4): 207-221.

Sturis et al., GLP-1 deriative liraglutide in rats with beta-cell deficiences: influence of metabolic state on beta-cell mass dynamics. British Journal of Pharmacology, 140 : 123-132 (2003).

Svartengren et al., Added External Resistance Reduces Oropharyngeal Deposition and Increases Lung Deposition of Aerosol Particles in Asthmatics. Am. J. Respir. Crit. Care Med., vol. 152, pp. 32-37, 1995.

Sympatecs. Dry Dispersion for Laser Diffraction and Image Analysis, 2011. XP-002586530.

Leone-Bay et al., Innovation in drug delivery by inhalation. Ondrugdelivery, No. 7, pp. 4-8 (2010).

Tack CJ, Boss AH, Baughman RA, et al. A randomized, double blind, placebo controlled study of the forced titration of prandial Technosphere®/Insulin in patients with type 2 diabetes mellitus. Diabetes 2006;55:Abstract 428-P.

Tack CJ, Christov V, deGalan BE, et al. Randomized forced titration to different doses of Technosphere® insulin demonstrates reduction in postprandial glucose excursions and hemoglobin A1c in patients with type 2 diabetes. J Diabetes Sci Technol 2008; 2(1) :47-57.

Tang-Christensen et al. "Central administration of GLP-1-(7-36) amide inhibits food and water intake in rats." Am J Physiol 271 (Regulatory Integrative Comp Physiol 40):R848, 1996.

Taylor et al. "Aerosols for macromolecule delivery. Design challenges and solutions." Am J Drug Deliv 2:143-155, 2004.

Teeter et al. "Dissociation of lung function changes with humoral immunity during inhaled human insulin therapy." Am J Resp Crit Care Med 173:1194, 2006.

Telko et al., Dry Powder Inhaler Formulation. Respiratory Care, Sep. 2005, vol. 50, No. 9, 1209-1227.

(56) References Cited

OTHER PUBLICATIONS

The American Diabetes Association "Insulin Administration" Diabetes Care, vol. 27, Supplement 1, S106-S109 (2004).
The Lancet. 1989, vol. 333, p. 1235-1236.
Thorens "Expression cloning of the pancreatic b-cell receptor for the gluco-incretin hormone glucagon-like peptide-1." PNAS 89:8641, 1992.
Thorens B et al. "Cloning and function expression of the human islet GLP-1 receptor: demonstration that exendin-4 is an agonist and exendin-(9-39) an antagonist of the receptor." Diabetes 42:1678, 1993.
Todd et al. "Glucagon-like peptide-1 (GLP-1: a trial of treatment in non-insulin-dependent diabetes mellitus." Eur J Clin Invest 27:533, 1997.
Todd et al. Subcutaneous glucagon-like peptide-1 improves postprandial glucaemic control over a 3-week period in patients with early type 2 diabetes. Clinical Science 95:325, 1998.
Toft-Nielson et al. "Determinants of the effectiveness of glucagon-like peptide-1 in type 2 diabetes." J Clin Endocrinol Metab 86:3853, 2001.
Toft-Nielson et al. "Exaggerated secretion of glucagon-like peptide-1 (GLP-1) could cause reactive hypoglcaemia." Diabetologia 41:1180, 1998.
Toft-Nielson et al. "The effect of glucagon-like peptide-1 (GLP-1) on glucose elimination in healthy subjects depends on the pancreatic glucoregulatory hormones." Diabetes 45:552, 1996.
Tornusciolo D.R. et al., Biotechniques 19(5):800-805, 1995. Simultaneous detection of TDT-mediated dUTP-biotin nick end-labeling (TUNEL)-positive cells and multiple immunohistochemical markers in single tissue sections.
Triantafyllidis et al., Structural, compositional and acidic characteristics of nanosized amorphous or partially crystalline ZSM-5 zeolite based materials. Microporous and Mesoporous Materials, 75:89-100 (2004).
Tu N, Kramer DA, Baughman RA. Inhaled Technosphere® Insulin improves glycemic control without weight gain. Diabetes 2007;56:Abstract 471-P.
Tuley et al., Experimental observations of dry powder inhaler dose fluidisation. International Journal of Pharmaceutics, 358, pp. 238-247 (2007).
Utah Valley University. Saponification. © 2009. Available from: <http://science.uvu.edu/ochem/index.php/alphabetical/s-t/saponification/printpage/>.
Vaczek, Accelerating drug delivery firms exploring new drug-delivery routes and devices intently awaiting the commercial launch of Exubera. Pharmaceutical & Medical Packaging News, vol. 14, No. 6 (2006).
Vahl et al. "Effects of GLP-1-(7-36)NH2, GLP-1-(7-37), and GLP-1-(9-36)NH2 on intravenous glucose tolerance and glucose-induced insulin secretion in healthy humans." J Clin Endocrinol Metabol 88:1772, 2003.
Van Alfen-Van Der Velden et al. "Successful treatment of severe subcutaneou insulin resistance with inhaled insulin therapy", Pediatric Diabetes 2010: 11:380-382.
Vara E et al. "Glucagon-like peptide-1 (7-36) amide stimulates surfactant secretion in human type II pneumocytes." Am J Resp Crit Care Med 163:840-846, 2001.
Vella A et al. "Effect of glucagon-like peptide 1(7-36) amide on glucose effectiveness and insulin action in people with type 2 diabetes." Diabetes 49:611, 2000.
Vella A et al. "The gastrointestinal tract and glucose tolerance." Curr Opin Clin Nutr Metab Care 7:479, 2004.
Vendrame et al. "Prediabetes: prediction and prevention trials." Endocrinol Metab Clin N Am, 2004, vol. 33, pp. 75-92.
Verdich C, et al., A meta-analysis of the effect of glucagon-like peptide-1 (7-36) amide on ad libitum energy intake in humans. J Clin Endocrinol Metab., 86:4382-4389, 2001.
Vilsboll et al. "Reduced postprandial concentrations of intact biologically active glucagon-like peptide-1 in type 2 diabetic patients." Diabetes 50:609, 2001.
Vilsboll et al. "Similar elimination rates of glucagon-like peptide-1 in obese type 2 diabetic patients and healthy subjects." J Clin Endocrinol Metab 88:220, 2003.
Vilsboll et al., "Evaluation of β-Cell Secretary Capacity Using Glucagon-Like Peptide 1", Diabetes Care, vol. 23, No. 6, pp. 807-812, Jun. 2000.
Vilsboll et al., "Incretin secretion in Relation to Meal Size and Body Weight in Healthy Subjects and People with Type 1 and Type 2 diabetes Mellitus", The Journal of Clinical Endrocronology & Metabolism, vol. 88, No. 6, pp. 2706-2713, 2003.
Amorij et al., Development of stable infleunza vaccine powder formulations challenges and possibilities. Pharmaceutical Research, vol. 25, No. 6, pp. 1256-1273 (2008).
Audouy et al., Development of a dried influenza whole inactivated virus vaccine for pulmonary immunization. Vaccine, vol. 29, pp. 4345-4352 (2011).
Volund "Conversion of insulin units to SI units." American Journal of Clinical Nutrition, Nov. 1993, 58(5), pp. 714-715.
Wachters-Hagedoorn et al. "The rate of intestinal glucose absorption is correlated with plasma glucose-dependent insulinotropic polypeptide concentrations in healthy men." J Nutr 136:1511, 2006.
Wang et al., Glucagon-like peptide-1 is a physiological incretin in rat. J. Clin. Invest, 95 : 417-421 (1995).
Wang et al., Glucagon-like peptide-1 regulates proliferation and apoptosis via activation of protein kinase B in pancreatic INS-1 beta cells. Diabetologia, 47:478-487, 2004.
Wareham et al., "Fasting Proinsulin Concentrations Predict the Development of Type 2 Diabetes", Diabetes Care, 1999, 22, 262-70.
Warren et al. "Postprandial versus prandial dosing of biphasic insulin aspart in elderly type 2 diabetes patients." Diabetes Res Clin Pract 66:23-29, 2004.
Waterhouse et al., "Comparatie assessment of a new breath-actuated inhaler in patients with reversible airways obstruction", Respiration 59:155-158 (1992).
WebMD (retrieved from http://www.webmd.com/pain-management/tc/pain-management-side-effects-of-pain-medicines in 2012, 4 pages).
Wei et al. "Tissue-specific expression of the human receptor for glucagon-like peptide-1: brain and pancreatic forms have the same deduced amino acid sequence." FEBS Letters 358:219, 1995.
Weir et al. "Glucagonlike peptide 1 (7-37) actions on endocrine pancreas." Diabetes 38:338, 1989.
Weiss, SR et al. "Inhaled insulin provides improved glycemic control in patients with type 2 diabetes mellitus inadequately controlled with oral agents." Arch Intern Med 163:2277-2282, 2003.
Weissberger, "Mannkind: Overlooked Biotech with Excellent Prospects (Part V)," http://www.investorvillage.com/smbd.asp?mb=2885&mn=45817&pt=msg&mid=5021385 (posted on Jun. 19, 2008, accessed on Oct. 18, 2012).
West, Solid State Chemistry and its Applications, Chp 10, Solid Solutions. Wiley, New York, 358 (1998).
Wettergren A et al. "Truncated GLP-1 (proglucagon 78-107-Amide) inhibits gastric and pancreatic functions in man." Digestive Diseases and Sciences 38:665, 1993.
White JR et al. "Inhaled insulin: an overview." Clinical Diabetes 19:13-16, 2001.
Wigley et al., Insulin across respiratory mucosae by aerosol delivery. Diabetes 20(8): 552-556 (1971).
Willms B et al. "Gastric emptying, glucose responses, and insulin secretion after a liquid test meal: effects of exogenous glucagon-like peptide-1 (GLP-1)-(7-36) amide in type 2 (noninsulin-dependent) diabetic patients." J. Clin Endocrinol Metab 81:327, 1996.
Wilson BR et al. "Technospheres(TM) for pulmonary and nasal applications." Respiratory Drug Delivery VIII, 2002,p. 545.
Wilson et al., Spray-drying, a viable technosphere formulation process option to lyophilization, http://www.aapsj.org/abstracts/AM_2004/AAPS2004-002724.PDF, 1 page, 2004.
Witchert, Low molecular weight PLA: A suitable polymer for pulmonary administered microparticles. J. Microencapsulation, 10(2): 195-207 (1993).
Wright et al., Inhaled Insulin: Breathing new life into diabetes therapy. Nursing, vol. 37, No. 1, p. 46-48 (2007).

(56) References Cited

OTHER PUBLICATIONS

Wong et al. "From cradle to grave: pancreatic b-cell mass and glucagon-like peptide-1." Minerva Endocrinologica 31:107, 2006.
Wuts et al. "The Role of Protective Groups in Organic Synthesis," John Wiley, New York, 2nd Ed. 1991.
Yan et al., Analgesic action of microinjection of neurokinin A into the lateral reticular nucleus and nucleus raphe magnus in rats. Acta Physiologica Sinica, vol. 48, No. 5, pp. 493-496 (1996)—abstract.
Yang et al., Division and differentiation of natural antibody-producing cells in mouse spleen. PNAS, 104(11): 4542-4546 (2007).
Yoshida et al., Absorption of insulin delivered to rabbit trachea using aerosol dosage form. J. Pharm. Sci. 68(5): 670-671 (1979).
Yoshioka et al., "Serum proinsulin levels at fasting and after oral glucose load in patients with Type 2 (non-insulin dependent) diabetes mellitus", Diabetogia, 1988, 31, 355-60.
Yu W, Marino MT, Cassidy JP, et al. Insulin antibodies associated with Technosphere® insulin. ADA 2010; Abstract 216-OR.
Yusta B et al. "GLP-1 receptor activation improves b-cell function and survival following induction of endoplasmic reticulum stress." Cell Metabolism 4:391, 2006.
Zander et al., Effect of 6-week course of glucagon-like peptide 1 on glycaemic control, insulin sensitivity, and beta-cell function in type 2 diabetes: a parallel-group study. Lancet, 359:824-830, 2002.
Zethelius et al., "Proinsulin is an Independent Predictor of Coronary Heart Disease", Circulation 105:2153-2158 (2002).
Zimmerman, K., "Respiratory System: Fats, Function, and Diseases", <www.livescience.com/22616-respiratory-system.html>, copyright 2013, p. 1.
Zisser et al. "In Patients Using Technospere Insulin. Variation in PPG Stayed Within ADA-recommended Targets Despite Large Variations in Glucose Load." Mannkind Corporation (2010), ADA 2010; Poster 554.
Zisser H, Jovanovic L, Markova K, et al. Technosphere® insulin effectively controls postprandial glycemia in patients with type 2 diabetes mellitus. Diabetes Technology and Therapeutics 2012;14:997-1001.
Wasada, Glucagon-like peptide-1 (GLP-1). Nihon Rinsho, vol. 62, No. 6, pp. 1175-1180 (2004) (full Japanese article with English abstract).
Bosquillon et al., Pulmonary delivery of growth hormone using dry powders and visualization of its local fate in rates. Journal of Controlled Release 96: 233-244 (2004).
Cho et al., Targeting the glucagon receptor family for diabetes and obesity therapy. Pharmacology & Therapeutics 135: 247-278 (2012).
Definition of medicament from http://medical-dictionary.thefreedictionary.com/medicament, retrieved by the Examiner on Mar. 20, 2015 and cited in Office Action issued on Mar. 26, 2015 in U.S. Appl. No. 13/942,482.
Definition of matrix from http://medical-dictionary.thefreedictionary.com/matrix, retrieved by the Examiner on Mar. 5, 2015 and cited in Office Action issued on Mar. 26, 2015 in U.S. Appl. No. 12/471,260.
Diabetes Frontier, vol. 10, No. 5, p. 647-657 (1999) (full Japanese article with translated English portion provided in separate attachment, portion translated in English is the bottom of p. 655 and the left column of p. 656).
Ely et al., Effervescent dry powder for respiratory drug delivery. European Journal of Pharmeutics and Biopharmaceutics 65: 346-353 (2007).
European Search report for European Application 14192154.4 mailed on Mar. 19, 2015.
Extended European Search report for European Application 14187552.6 mailed on Mar. 2, 2015.
Gillespie et al., Using carbohydrate counting in diabetes clinical practice. Journal of the American Diabetic Association, vol. 98, No. 8, p. 897-905 (1998).
Yamamoto et al., Engineering of Poly (DL-lactic-co-glycolic acid) Nano-composite particle for dry powder inhalation dosage forms of insulin with spray fludized bed granulating system. J. Soc. Powder Technol., Japan, 41: 514-521 (2004).
Pfutzner et al. "Inhaled Technosphere/Insulin Shows a Low Variability in Metabolic Action in Type 2 Diabetic Patients." Diabetes 49 Supplement, May 2000, A121.
Pfuetzner A, Rave K, Heise T, et al. Inhaled Technosphere™/insulin results in low variability in metabolic action in type 2 diabetic patients. Exp Clin Endocrinol Diabetes 2000; 108:S161.
Pfuetzner A, Rave K, Heise T, et al. Low variability in metabolic action in type 2 diabetic patients with inhaled Technosphere/insulin. Diabetologia 2000; 43:Abstract 774.
Phillips M, Amin N, Boss AH, et al. Pulmonary functions (over 2 years) in diabetic subjects treated with Technosphere® insulin or usual antidiabetic treatment. Diabetologia 2009; 52 (suppl 1).
Pohl R, Muggenberg BA, Wilson BR, et al. A dog model as predictor of the temporal properties of pulmonary Technosphere/insulin in humans. Respiratory Drug Delivery 2000; VII: 463-465.
Polonsky et al. "Abnormal Patterns of Insulin Secretion in Non-insulin-Dependent Diabetes Mellitus." N Eng J Med 318:1231-39, 1988.
Potocka E, Amin N, Cassidy J, et al. Insulin pharmacokinetics following dosing with Technosphere® insulin in subjects with chronic obstructive pulmonary disease. Current Medical Research and Opinion 2010; 26:2347-2353.
Potocka E, Baughman R A, Derendorf H. Population pharmacokinetic model of human insulin following different routes of administration. Journal of Clinical Pharmacology 2011;51:1015-1024.
Potocka E, Baughman R, Derendorf H. Population Pharmacokinetic Model of Regular Human Insulin Following Different Routes of Administration. AAPS Journal. 2009; 11(S1). Available from: http://www.aapsj.org. Presented at the 2009 AAPS (American Association of Pharmaceutical Scientists) National Biotechnology Conference, Jun. 21-24, Seattle, WA.
Potocka E, Baughman RA, Derendorf J. A population PK/PD model of Technosphere® insulin administered to healthy and type 2 diabetics. ADA 2010; Poster 624.
Potocka E, Baughman RA, Schwartz SL, et al. Pharmacokinetics of AFRESA® unchanged in patients with chronic obstructive pulmonary function ADA 2009; Poster 437.
Potocka E, Cassidy J P, Haworth P, et al. Pharmacokinetic characterization of the novel pulmonary delivery excipient fumaryl diketopiperazine. Journal of diabetes science and technology 2010;4:1164-1173.
Potocka E, Cassidy JP, Haworth P, et al. Pharmacokinetic characterization of fumaryl diketopiperazine. Third International Conference on Advanced Technologies and Treatments for Diabetes 2010; Poster 291.
Potocka E, Hovorka R, Baughman R, et al. Characterization of metabolism parameters following Technosphere® insulin and insulin Lispro. ADA 2010; Poster 1561.
Potocka E, Hovorka R, Baughman RA, et al. AFRESA™ supresses endogenous glucose production earlier than a rapid-acting analog (Lispro) and inhaled Exubera® ADA 2009; Oral 232.
Potocka E, Hovorka R, Baughman RA, et al. Technosphere® insulin suppresses endogenous glucose production earlier than a rapid-acting analog (lispro) and an inhaled insulin (exubera). Diabetologia 2009; 52 (suppl 1).
Prabhu et al. "A study of factors controlling dissolution kinetic of zinc complexed protein suspensions in various ionic species", Int. J. Pharm. 217(1-2):71-8 (2001).
Laube et al., The lung as an alternative route for delivery for insulin in controlling postrprandial glucose levels in patients with diabetes. Chest, Preliminary Report 114 (6) : 1734-1739 (1998).
Quattrin et al. "Efficacy and Safety of Inhaled Insulin (Exubera) Compared with Subcutaneous Insulin Therapy in Patients with Type 1 Diabetes." Diabetes Care, vol. 27, No. 11, Nov. 2004, p. 2622-2627.
Quddusi et al. "Differential effects of acute and extended infusions of glucagon-like peptide-1 on first- and second-phase insulin secretion in diabetic and nondiabetic humans." Diabetes Care 26:791, 2003.

(56) References Cited

OTHER PUBLICATIONS

Rachman et al. "Normalization of insulin responses to glucose by overnight infusion of glucagon-like peptide 1 (7-36) amide in patients with NIDDM." Diabetes 45:1524, 1996.
Raju et al., Naseseazines A and B: a new dimeric diketopiperazine framework from a marine-derived actinomycete, *Streptomyces* sp. Organic letters, vol. 11, No. 17, pp. 3862-3865 (2009).
Raskin et al. "Continuous subcutaneous insulin infusion and multiple daily injection therapy are equally effective in type 2 diabetes." Diabetes Care, vol. 26, No. 9, pp. 2598-2603, Sep. 2003.
Raskin P, Heller S, Honka M, et al. Pulmonary function over 2 years in diabetic patients treated with prandial inhaled Technosphere® Insulin or usual antidiabetes treatment: A randomized trial. Diabetes, Obesity and Metabolism 2012;14:163-173.
Raskin P, Phillips M, Amin N, et al. Hypoglycemia in patients with type 1 diabetes incorporating prandial inhaled Technosphere® insulin into their usual diabetes treatment regimen vs continuing their usual diabetes management. AACE 2010; Poster 283.
Raskin P, Phillips MD, Rossiter A, et al. A1C and hypoglycemia in patients with type 2 diabetes mellitus incorporating prandial inhaled Technosphere® insulin into their usual antihyperglycemic regimen vs continuing their usual antihyperglycemic regimen. ADA 2010; Abstract 359-OR.
Raufman et al., Exendin-3, a novel peptdie from Heloderma horridum venom, interacts with vasoactive intestinal peptide receptors and a newly described receptor on dispersed aciin from guinea pig pancreas. J. Biol. Chem. 266(5) : 2897-2902 (1991).
Raufman et al., Truncated glucagon-like peptide-1 interacts with exendin receptors on dispersed acini from guina pig pancreas. J. Biol. Chem. 267(30) : 21432-21437 (1992).
Raun et al. "Liraglutide, a long-acting glucagon-like peptide-1 analog, reduces body weight and food intake in obese candy-fed rats, where as a dipeptidyl peptidase-IV inhibitor, vildagliptin, does not." Diabetes 56:8, 2007.
Rave et al. "Coverage of Postprandial Blood Glucose Excursions with Inhaled Technosphere Insulin in Comparison to Subcutaneously Injected Regular Human Insulin in Subjects with Type 2 Diabetes." Diabetes Care, vol. 30, No. 9, pp. 2307-2308, Sep. 2007.
Rave et al. "Dose Response of Inhaled Dry-Powder Insulin and Dose Equivalence to Subcutaneous Insulin Lispro." Diabetes Care 28:2400-2405, 2005.
Rave et al. "Inhaled Technosphere Insulin in Comparison to Subcutaneous Regular Human Insulin: Time Action Profile and Variability in Subjects with Type 2 Diabetes." Journal of Diabetes Science and Technology, vol. 2, Issue 2, pp. 205-212, Mar. 2008.
Rave et al. "Results of a Dose-Response Study with a New Pulmonary Insulin Formulation and Inhaler." Diabetes 49, Supplement, May 2000, A75.
Rave et al. "Time-action profile of inhaled insulin in comparison with subcutaneously injected insulin lispro and regular human insulin." Diabetes Care 28:1077, 2005.
Rave K, Heise T, Pfuetzner A, et al. Assessment of dose-response characteristics for a new pulmonary insulin formulation and inhaler. Exp Clin Endocrinol Diabetes 2000; 108:S161.
Rave K, Potocka E, Boss AH, et al. Pharmacokinetics and linear exposure of AFRESA™ compared with the subcutaneous injection of regular human insulin Diabetes, Obesity and Metabolism 2009; 11:715-720.
Raz et al. "Pharmacodynamics and Pharmacokinetics of Dose Ranging Effects of Oralin versus S.C. Regular Insulin in Type 1 Diabetic Patients." Fourth Annual Diabetes Technology Meeting, Philadelphia PA, 2004.
Razavi et al. "TRPVI+ sensory neurons control beta cell stress and islet inflammation in autoimmune disease." Cell 127:1123, 2006.
Retrieved from website: http://groups.molbiosci.northwestern.edu/holmgren/Glossary/Definitions/Def-P/placebo.html, 1 page, Retrieved on Mar. 12, 2013.
Rhodes et al. "Technosphere: Microspherical Particles from Substituted Diketopiperazines for Use in Oral Drug Delivery." 208th ACS National Meeting, Aug. 1994.

Richardson et al. "Technosphere Insulin Technology." Diabetes Technology & Therapeutics, vol. 9, Supplement 1, pp. S65-S72, 2007.
Richardson PC, Potocka E, Baughman RA, et al. Pharmacokinetics of Technosphere® insulin unchanged in patients with chronic obstructive pulmonary disease. Diabetologia 2009; 52 (suppl 1).
Richter et al. "Characterization of glucagon-like peptide-1(7-36)amide receptors of rat membranes by covalent cross-linking." FEBS Letters 280:247, 1991.
Richter et al. "Characterization of receptors for glucagon-like peptide-1 (7-36)amide on rat lung membranes." FEBS Letters 267:78, 1990.
Riddle "Combining Sulfonylureas and Other Oral Agents." Am J Med, 2000, vol. 108(6A), pp. 15S-22S.
Riddle et al. "Emerging therapies mimicking the effects of amylin and glucagon-like peptide 1" Diabetes Care 29:435, 2006.
Ritzel et al. "Pharmacokinetic, insulinotropic, and glucagonostatic properties of GLP-1 (7-36 amide) after subcutaneous injection in healthy volunteers. Dose-response-relationships." Diabetologia 38:720, 1995.
Rosen et al., Substance P microinjected into the periaqueductal gray matter induces antinociception and is released folloing morphine administration. Brain Research, 1001: 87-94 (2004).
Rosenmund et al., Diketopiperazines from Leuchs Anhydrides. Angew Chem Intern. Edit. vol. , No. 2 (1970).
Rosenstock "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018-PO, 2008.
Rosenstock et al. "Efficacy and Safety of Technosphere Inhaled Insulin Compared With Technosphere Powder Placebo in Insulin-Naive Type 2 Diabetes Suboptimally Controlled with Oral Agents." Diabetes Care, vol. 31, No. 11, pp. 2177-2182, 2008.
Rosenstock et al. "Inhaled Insulin Improves Glycemic Control when Substituted for or Added to Oral Combination Therapy in Type 2 Diabetes." Ann Intern Med 143:549-558, 2005.
Rosenstock et al., "Reduced hypoglycemia risk with insulin glargine: a meta-analysis comparing insulin glargine with human NPH insulin in type 2 diabetes", Diabetes Care, 28(4):950-5 (2005).
Rosenstock J, Baughman RA, Ribera-Schaub T, et Al. A randomized, double-blind, placebo controlled study of the efficacy and safety of inhaled Technosphere® insulin in patients with type 2 diabetes (T2DM). Diabetes 2005;54: Abstract 357-OR.
Rosenstock J, Lorber D, Petrucci R, et al. Basal/bolus with prandial inhaled Technosphere® insulin (TI) plus insulin glargine qd vs biaspart 70/30 insulin bid in T2 DM inadequately controlled on insulin with/without oral agents ADA 2009; Poster 466.
Rosenstock J, Lorger DL. Gnudi L, et al.Prandial inhaled insulin plus basal insulin glargine versus twice daily biaspart insulin for type 2 diabetes: a multicentre randomised trial. Lancet 2010;375:2244-2253.
Rossiter A, Amin N, Harris R, et al. Pulmonary safety of inhaled Technosphere® insulin therapy in adults with diabetes using high-resolution computerized tomography of the chest. Diabetologia 2009; 52 (suppl 1).
Rossiter A, Howard C, Amin N, et al. Technosphere® insulin: Safety in type 2 diabetes mellitus. ADA 2010; Poster 523.
Roumeliotis, New inhaler launched with a bag, in-Pharma Technologist.com, Decision News Media SAS (2006).
Rousseau et al. "Drug delivery by fumaryl diketopiperazine particles: evidence for passive transport." Presented at the American Diabetes Association 64th Scientific Sessions, Jun. 2004, abstract 484-P.
Rubin RR, Peyrot M. Psychometric properties of an instrument for assessing the experience of patients treated with inhaled insulin: The inhaled insulin treatment questionnaire (INTQ) Health & Quality of Life Outcomes Aug. 2010:32.
Rubin RR, Peyrot M; Patient reported outcomes in adults with type 1 diabetes using mealtime AFRESA® (inhaled Technosphere® insulin) or rapid acting insulin with basal insulin ADA 2009; Poster 1881.

(56) References Cited

OTHER PUBLICATIONS

Ryan EA et al. "Successful islet transplantation. Continued insulin reserve provides long-term glycemic control." Diabetes 51:2148-2157, 2002.
Sajeesh et al., Cyclodextrin-insulin complex encapsulated polymethacrylic acid based nanoparticles for oral insulin delivery. International Journal of Pharmaceuticals, 2006, 325, pp. 147-154.
Sakagami M et al. "Respirable microspheres for inhalation: the potential of manipulating pulmonary disposition for improved therapeutic efficacy." Clin Pharmacokinet 44(3):263-277, 2005.
Sakr, A new approach for insulin delivery via the pulmonary route: design and pharmacokinetics in non-diabetic rabbits. International Journal of Pharmaceutics, 86: 1-7 (1992).
Salib, Utilization of sodium alginate in drug microencapsulation. Pharazeutische Industrie, 40(11a): 1230-1234 (1978).
Saraceni C et al. "Effects of glucagon-like peptide-1 and long-acting analogues on cardiovascular and metabolic function." Drugs R D 8:145, 2007.
Sarrach et al., "Binding and entrapment of insulin by liposomes made of lecithin-phosphotidix acid in acid solution" Pharmazie 40:642-645, 1985 (German and English Abstract).
Savage et al., "Effects of peptide YY (PYY) on mouth to caecum intestinal transit time and on the rate of gastric emptying healthy volunteers", Gut, vol. 28, pp. 166-170, 1987.
Sawhney et al., Bioerodible hydrogels based on photopolymerized poly(ethylene glycol)-co-poly(a-hydroxy acid) diacrylate macromers. Macromolecules, 26: 581-587 (1993).
Schaffer et al. "Assembly of high-affinity insulin receptor agonists and antagonists from peptide building blocks." PNAS 100:4435-4439, 2003.
Schepp et al., Eur. J. Pharmacol., 269:183-91, 1994.
Scherbaum "Unlocking the opportunity of tight glycaemic control. Inhaled insulin: clinical efficacy." Diabetes Obesity and Metabolism 7:S9-S13, 2005.
Schirra et al. "Gastric emptying and release of incretin hormones after glucose ingestion in humans." J Clin Invest 97:92-103, 1996.
Schluter et al., "Pulmonary Administration of Human Insulin in volunteers and Type I Diabetics", Diabetes, 33, (Suppl) 298 (1984).
Schneider et al., "Stimulation by proinsulin of expression of plasminogen activator inhibitor type 1 in endothelial cells", Diabetes 41(7):890-895 (1992).
Schon, Istvan et al. "Formation of Aminosuccinyl Peptides During Acidolytic Deprotection Followed by their Tranformation to Piperazine-2, 5-dione Derivatives in Neutral Media." International Journal of Peptide & Protein Research, 14(5), 485-494, 1979.
Schroder, "Crystallized carbohydrate spheres as a slow release matrix for biologically active substances", Biomaterials 5:100-104, 1984.
Scrocchi et al. "Glucose intolerance but normal satiety in mice with a null mutation in the glucagon-like peptide 1 receptor gene." Nature Medicine 2:1254-1258, 1996.
Seshiah & Balaji, "Early Insulin Therapy in Type 2 Diabetics", Int. J. Diabetes in Developing Countries, 2003, 23, 90-93.
Seville, P.C. et al., Preparation of dry powder dispersions for non-viral gene delivery by freeze-drying and spray drying. J. Gene Medicine 2002; 4:428-437.
Shah et al. "Lack of suprression of glucagon contributes to postprandial hyperglycemia in subjects with type 2 diabetes mellitus." J Clin Indocrinol Metab 85:4053, 2000.
Shelly et al. "Polysorbate 80 hypersensitivity." The Lancet 345:1312, 1995.
Shimada et al. Translocation pathway of the intertracheally instilled ultrafine particles from the lung into the blood circulationin the mouse. Toxicologic Pathology pp. 949-957 (2006).
Shojania et al. "Effect of quality improvement strategies for type 2 diabetes on glycemic control." JAMA 296:427, 2006.
Silverstein et al., "Care of Children and Adolescens with Type 1 Diabetes, A Statement of the American Diabetes Association", Diabetes Care, Jan. 2005, vol. 28, p. 186-212.
Singh et al., Use of 125I-[Y39]exendin-4 to characterize exendin receptors on dispersed pancreatic acini and gastric chief cells from guinea pig. Regul. Pept. 53 : 47-59 (1994).
Simms JR, Carballo I, Auge CR, et al. Assessment of immunotoxic effects on humoral and cellular immune parameters following repeated inhalation of Technosphere insulin in the rat. Diabetes 2005;54:Abstract 2078-PO.
Skyler, Pulmonary insulin: current status. Diabetes Voice, vol. 51, Issue I, p. 23-25, 2006.
Skyler "Pulmonary Insulin Delivery—State of the Art 2007." Diabetes Tecnology & Therapeutics, vol. 9, Supplement 1, pp. S1-S3. 2007.
Skyler JS et al. "Use of inhaled insulin in a basal/bolus insulin regimen in Type 1 diabetic subjects." Diabetes Care 28:1630-1635, 2005.
Smith et al. "New-onset diabetes and risk of all-cause and cardiovascular mortality." Diabetes Care 29:2012, 2006.
Smutney CC, Friedman EM, Amin N. Inspiratory efforts achieved in use of the Technosphere® insulin inhalation system. Diabetes Technology Meeting 2008; Poster SMUT8052.
Smutney CC, Friedman EM, Amin N. Inspiratory efforts achieved in use of the Technosphere® insulin inhalation system. Journal of Diabetes Science and Technology 2009 3(5):1175-1189.
Smutney CC, Polidoro JM, Adamo B, et al. In-vitro performance improvement realized in a next generation dry powder delivery system. Diabetes Technology Meeting 2009; poster.
Smutney CC, Polidoro JM, Adamo B, Shah S. In vitro performance improvement realized in a next generation dry powder delivery system. Third International Conference on Advanced Technologies and Treatments for Diabetes 2010; Poster 122.
Smutney CC, Polidoro JM. Easy-to-use next-generation pulmonary insulin delivery system. ADA 2010; Abstract 2093.
Smutney CC, Polidoro JM. Improvements realized in a next-generation pulmonary insulin delivery system. ADA 2010; Abstract 2097.
Sodium chloride is a natural product from http://www.wqpmag.com/potassium-chloride-vs-sodium-chloride, pp. 1-3. Accessed by Examiner on May 16, 2014 in Non-Final Office Action dated May 22, 2014 for U.S. Appl. No. 13/797,657 and in Non-Final Office Action dated May 22, 2014 for U.S. Appl. No. 12/883,369.
"An inhaled insulin formulation (Technosphere Insulin) effectively improves glycaemic control in patients with type 2 diabetes mellitus." Inpharma Weekly, vol. 1522, Jan. 28, 2006, p. 8.
Adjusting Mealtime Insulin Doses. BD Diabetes. http://www.bd.com/diabetes/page.aspx?cat=7001&id=7280 (2014).
Ahren "GLP-1 and extra-islet effects." Horm. Med Res 36:842, 2004.
Ahren B et al. "Characterization of GLP-1 effects on b-cell function after meal ingestion in humans." Diabetes Care 26:2860, 2003.
Ahren B., Glucagon-like peptide-1 (GLP-1): a gut hormone of potential interest in the treatment of diabetes. BioEssays, V. 20, pp. 642-651 (1998).
Akerlund et al., Diketopiperazine-based polymers from common acids. Journal of Applied Polymer Science (2000), 78(12), 2213-2218.
Alabraba et al. Diabetes Technology & Therapeutics. Jul. 2009, 11(7): 427-430.
Alcohols limited. Alcohol speciality solvents—Go green! Jul. 24, 2010. Available from: <http://webarchive.org/web/20100724193725/http://www.alcohols.co.uk/speciality_solvents.php>.
Aljada et al. "Insulin inhibits the pro-inflammatroy transcription factor early growth response gene-1 (Egr)-1 expression in mononuclear cells (MNC) and reduces plasma tissue factor (TF) and plasminogen activator inhibitor-1 (PAI-1) concentrations." The Journal of Clinical Endocrinology and Metabolism, vol. 87, No. 3, p. 1419-1422, 2002.
Al-Showair et al., Can all patients with COPD use the correct inhalation flow with all inhalers and does training help? Respiratory Medicine, vol. 101, No. 11, p. 2395-2401 (2007).
American Diabetes Association, "Standards of medical care in diabetes—2009", Diabetes Care, Jan. 2009, 32 Suppl 1: S13-61.

(56) References Cited

OTHER PUBLICATIONS

Amin N, Boss AH, Petrucci R, et al. Pulmonary functions (over 2 years) in diabetic subjects treated with AFRESA® or usual antidiabetic treatment ADA 2009; Poster 570.

Amin N, et al. Long-term sustained safety and efficacy of continued use of Technosphere insulin in subjects with type 2 diabetes. Abstract—Oral Presentation 215, 48th EASD Annual Meeting, Sep. 29-Oct. 2, 2009, Vienna Austria.

Amin N, Marino MT, Cassidy JP, et al. Acute pulmonary effects of Technosphere® insulin inhalation powder administered using a Gen2B inhaler compared to MedTone® C inhaler. Diabetes Technology Meeting 2010; poster.

Amin N, Phillips M, Boss AH, et al. Pulmonary functions (over 2 years) in diabetic patients treated with Technosphere® insulin (TI) or usual antidiabetic treatment. Third International Conference on Advanced Technologies and Treatments for Diabetes. 2010; Poster 290.

Angelo et al., Technosphere Insulin: Defining the Role of Technosphere Particles at the Celluar Level. J. Diabetes Sci. Technol., vol. 3, Issue 3, pp. 545-554 (2009).

Angelo et al. Technosphere® insulin inhalation powder: Defining the mechanism of action. ADA 2008; 57: Poster 428-P.

Antosiewiez et al., Prediction of pH-dependent properties of proteins. J Mol. Biol., 238:415-436 (1994).

Arakawa et al., Preferential interactions determine protein solubility in three-component solutions: the MgCl2 system. Biochemistry, 29:1914-1923 (1990).

Ashwell et al. "Twice-daily compared with once-daily insulin glargine in people with Type 1 diabetes using meal-time insulin aspart." 2006 Diabetes UK, Diabetic Medicine, 23, 879-886.

Ashwell et al., "Optimal timing of injection of once-daily insulin gargine in people with Type 1 diabetes using insulin lispro at meal-times" 2005 Diabetes UK, Diabetic Medicine, 23, 46-52.

Atherton, F. et al. "Synthesis of 2(R)-A3(S)-Acylamino-2-OXO-1-Azetidinyloxy U-Acetic Acids." Tetrahedron, vol. 40, No. 6, Jan. 1, 1984, pp. 1039-1046.

Baggio et al. "A recombinant human glucagon-like peptide (GLP)-1-albumin protein (Albugon) mimics peptidergic activation of GLP-1 receptor-dependent pathways coupled with satiety, gastrointestinal motility, and glucose homeostasis." Diabetes 53:2492, 2004.

Baggio et al. "Glucagon-like peptide-1, but not glucose-dependent insulinotropic peptide, regulates fasting glycemia and noneneteral glucose clearance in mice." Endocrinology 141:3703, 2000.

Baggio et al. "Harnessing the therapeutic potential of glucagon-like peptide-1." Treat Endocrinol 1:117, 2002.

Drucker et al., Minireview: The glucagon-like peptides. Endocrinology, vol. 142, No. 2, pp. 521-527 (2001).

Balkan B et al. "Portal GLP-1 administration in rats augments the insulin response to glucose via neuronal mechanisms." Am J. Physiol Regulatory Integrative Comp Physiol 279:R1449, 2000.

Barnett AH et al. "An open, randomized, parallel-group study to compare the efficacy and safety profile of inhaled human insulin (Exubera) with glibenclamide as adjunctive therapy in patients with Type 2 diabetes poorly controlled on metformin." Diabetes Care 29(8):1818-1825, 2006.

Barnett et al., An open, randomized, parallel-group study to compare the efficacy and safety profile of inhaled human insulin (Exubera) with metformin as adjunctive therapy in patients with type 2 diabetes poorly controlled on a sulfonylurea. Diabetes Care, 29(6): 1282-1287 (2006).

Barragan et al. "Changes in arterial blood pressure and heart rate induced by glucagon-like peptide-1-(7-36) amide in rats." Am J. Physiol 266 (Endocrinol Metab 29):E459, 1994.

Basu A et al. "Effects of a change in the pattern of insulin delivery on carbohydrate tolerance in diabetic and nondiabetic humans in the presence of differing degrees of insulin resistance." J Clin Invest 97:2351-2361, 1996.

Bauer et al., "Assessment o beta-adrenergic receptor blockade after isamoitane, a 5-HT1-receptor active compound, in healthy volunteer", Clin. Pharmacol Ther 53:76-83 (1993).

Bauer et al., "Pharmacodynamic effects of inhaled dry powder formulations of fenterol and colforsin in asthma", Clin Pharmacol Ther 53:76-83, 1993.

Baughman R, Cassidy J, Amin N, et al. A phase I, open-label study of the effect of albuterol or fluticasone on the pharmacokinetics of inhaled Technosphere® insulin inhalation powder in healthy subjects. ADA 2010; Poster 528.

Baughman R, Cassidy J, Levy B, et al. Technosphere® insulin inhalation powder pharmacokinetics unchanged in subjects who smoke. Diabetes 2008; 57: A128.

Baughman R, Haworth P, Litwin J, et al. No cardiac effects found with therapeutic and suprtherapeutic doses of Technosphere® inhalation powder: results from a thorough QTc clinical study. ADA 2011. Poster 933-P.

Baughman, RA, Evans, SH, Boss, AH, et al. Technosphere insulin does not affect pulmonary function in a 6 month study of patients with type 2 diabetes. Diabetologia 2006;49:177-118.

Bayés M et al. "Gateways to clinical trials" Methods Find Exp Clin Pharmacol 24:431-455, 2002.

Beers et al., Section 2—Chapter 13—Diabetes Mellitus, The Merck Manual of Diagnosis and Therapy, Merck Research Laboratories, pp. 165-177 (1999).

Behme et al. "Glucagon-like peptide-1 improved glycemic control in type 1 diabetes." BMC Endocrine Disorders 3:3, 2003.

Bellary et al. "Inhaled insulin:new technology, new possibilities." Int J Clin Pract 60:728, 2006.

Belmin J et al. "Novel drug delivery systems for insulin. Clinical potential for use in the elderly." Drugs Aging 20:303-12, 2003.

Benita, Charaterization of Drug-Loaded Poly(d,l-lactide) Microspheres. J. Pharm. Sci., 73: 1721-1724 (1984).

Benito E et al. "Glucagon-like peptide-1-(7-36) amide increases pulmonary surfactant secretion through a cyclic adenosine 3',5'-monophosphate-dependent protein kinase mechanism in rat type II pneumocytes." Endocrinology 139:2363, 1998.

Bensch et al., Absorption of intact protein molecules across the pulmonary air-tissue barrier, Science 156: 1204-1206 (1967).

Berge et al., "Pharmaceutical Salts", J. Pharmaceutical Sciences, Review Article, 66(1):1-19 (1977).

Bergenstal R, Kapsner P, Rendell M, et al., Comparative efficacy and safety of AFRESA® and a rapid-acting analog both given with glargine in subjects with T1 DM in a 52-week study ADA 2009; Poster 479.

Bergeron et al. "Macromolecular Self-Assembly of Diketopiperazine Tetrapeptides." J. Am. Chem. Soc. 116, 8479-8484, 1994.

Li et al. "GLP-1; a novel zinc finger protein required in somatic cells of the gonad for germ cell development." Dev Biol 301:106, 2007.

Li, Jun. Chapter 15: Drug Therapy of Metabolic Diseases. Clinical Pharmacotherapy, People's Medical Publishing House, 1st Edition, pp. 333-335 (2007).

Lian et al. "A Self-Complimentary Self-Assembling Microsphere System: Application for Intravenous Delivery of the Antiepiletic and Neuroprotectant Compound Felbanate." J Pharm Sci 89:867-875, 2000.

Lim, "Microencapsulation of Living Cells and Tissues", J. Pharm. Sci., 70: 351-354 (1981).

Linder et al., Increase in serum insulin levels is correlated with lung distribution after pulmonary delivery of Technosphere/Insulin. Diabetologia, No. 46, A277 (2003).

Liu et al., "Pulmonary delivery of free and liposomal insulin", Pharmaceuticals Res. 10:228-232, 1993.

Lorber D, Howard CP, Ren H, et al. Reduced incidence and frequency of hypoglycemia in an integrated analysis of pooled data from clinical trials of subjects with type 2 diabetes using prandial inhaled Technosphere® insulin. AACE 2010; Poster 270.

Luque et al. "Glucagon-like peptide-1 (GLP-1) and glucose metabolism in human myocytes." J. Endocrinol 173:465, 2002.

(56) References Cited

OTHER PUBLICATIONS

Luzi, L. and DeFronzo, R.A. "Effect of loss of first-phase insulin secretion on hepatic glucose production and tissue glucose disposal in humans." Am. J. Physiol. 257 (Endocrinol. Metab. 20):E241-E246, 1989.
Luzio, S.D., et al. "Intravenous insulin simulates early insulin peak and reduces post-prandial hyperglycaemia/hyperinsulinaemia in type 2 (non-insulin-dependent) diabetes mellitus." Diabetes Res. 16:63-67, 1991.
Malhotra et al., Exendin-4, a new peptide from Heloderma suspectum venom, potentiates cholecystokinin-induced amylase release from rat pancreatic acini. Regulatory Peptides, 41:149-56, 1992.
Mandal "Inhaled insulin for diabetes mellitus." Am J Health Sys Pharm 62:1359-64, 2005.
Mann "Pulmonary insulin—the future of prandial insulin therapy." Presented at the 5th Annual Meeting of the Diabetes Technology Society, Nov. 2005, abstract A94.
MannKind Corporation "Postprandial hyperglycemia: clinical significance, pathogenesis and treatment." MannKind Corporation Monograph. 2009.
MannKind Corporation, Pulmonary Delivery: Innovative Technologies Breathing New Life into Inhalable Therapeutics, www.ondrugdelivery.com, 2006.
Burcelin et al., Long-lasting antidiabetic effect of a dipeptidyl peptidase IV-resistant analog of glucagon-like peptide-1. Metabolism, vol. 48, No. 2, pp. 252-258 (1999).
Marino MT, Cassidy JP, Smutney CC, et al. Bioequivalence and dose proportionality of Afrezza® inhalation powder administered using a Gen2 inhaler compared to the MedTone® inhaler. Diabetes Technology Meeting 2010; poster.
Marino MT, Cassidy JP, Smutney CC, et al. Improvement in bioavailability of FDKP with the NexGen2A device: Implications for delivery of pulmonary insulin. Third International Conference on Advanced Technologies and Treatments for Diabetes 2010; Poster 108.
Marino MT, Cassidy JP, Smutney CC, et al. Improvement in bioavailability of FDKP and insulin with the NGDSB device. Third International Conference on Advanced Technologies and Treatments for Diabetes 2010; Poster 107.
Marino MT. A pharmacokinetic/pharmacodynamic model of inhaled insulin with application to clinical trial simulation. ADA 2010; Abstract 2105-PO.
Marino MT. Cassidy JP, Baughman RA, et al. C-peptide correction method to determine exogenous insulin levels in pk studies using AFRESA® (Technosphere® insulin [TI]) ADA 2009; Poster 1451.
Marshall "Preventing and detecting complications of diabetes." BMJ 333:455, 2006.
Mastrandrea "A breath of life for inhaled insulin: severe subcutaneous insulin resistance as an indication." Pediatric Diabetes 2010: 11: 377-379.
Mathiowitz, Morphology of Polyanhydride Microsphere Delivery Systems, Scanning Microscopy, 4: 329-340 (1990).
Mathiowitz, Novel microcapsules for delivery systems. Reactive Polymers, 6: 275-283 (1987).
Mathiowitz, Polyanhydride microspheres as drug carriers I, hot-melt microencapsulation. J. Controlled Medicine, 5: 13-22 (1987).
Mathiowitz, Polyanhydride microspheres as drug carriers II, micro-encapsulation by solvent removal. J. Appl. Polymer Sci., 35: 755-774 (1988).
Mathiowitz, Polyanhydride microspheres IV, morphology and characterization systems made by spray drying. J. App. Polymer Sci., 45: 125-134 (1992).
Matsui et al. "Hyperplasia of type II pheumocytes in pulmonary lymphangioleiomyomatosis. Immunohistochemical and electron microscope study." Arch Pathol Lab Med 124:1642, 2000.
Matthews DR et al. "Homeostasis model assessment: insulin resistance and beta-cell function from fasting plasma glucose and insulin concentrations in man." Diabetologia. Jul. 1985;28(7):412-9.

McElduff A et al. "Influence of acute upper respiratory tract infection on the absorption of inhaled insulin using the AERx(R) insulin diabetes management system." Br J Clin Pharmacol 59:546, 2005.
McMahon et al., "Effects of basal insulin supplementation on disposition of mixed meal in obese patients with NIDDM", Diabetes, vol. 38, pp. 291-303 (1989).
Meier et al. "Absence of a memory effect for the insulinotropic action of glucagon-like peptide-1 (GLP-1) in healthy volunteers." Horm Metab Res 35:551, 2003.
Meier et al. "Secretion, degradation, and elimination of glucagon-like peptide-1 and gastric inhibitor polypeptide in patients with chronic renal insufficiency and healthy control subjects." Diabetes 53:654, 2004.
Meier et al. "The glucagon-like peptide-1 metabolite GLP-1-(9-36) amide reduces postprandial glycemia independently of gastric emptying and insulin secretion in humans." Am J Physiol Endocrinol Metab 290:E1118, 2006.
Mendes et al., A non-dimensional functional relationship for the fine particle fraction produced by dry powder inhalers, Aerosol Science 38, pp. 612-624 (2007).
Mentlein et al., Dipeptidyl peptidase IV hydrolyses gastric inhibitory polypeptide, glucagon-like peptide-1 (7-36) amide, peptide histidine methionine and is responsible for their degradation in human serum. Eur J Biochem., 214:829-835, 1993.
Merck Manual 17th, Japanese Edition, NIKKEI BP Corp., 1999, p. 167-179.
Mitchell et al. "Intranasal Insulin: PK Profile Designed Specifically for Prandial Treatment of Type 2 Diabetes." Drug Development Research 69(3):143-152 (2008).
Monnier et al. "Activation of oxidative stress by acute glucose fluctuations compared with sustained chronic hyperglycemia in patients with type 2 diabetes." JAMA 295:1681, 2006.
Montrose-Rafizadeh et al., Diabetes, 45(Suppl. 2):152A, 1996.
Moren, Aerosols in Medicine (2nd Ed.), Elsevier, pp. 321-350 (1993).
Mudaliar et al., Insulin Therapy in Type 2 Diabetes. Endocrinology and Metabolism Clinics, vol. 30, No. 4, pp. 1-32 (2001).
Nagai et al., "Powder Dosage Form of Insulin for Nasal Administration", J. Control Ref., 1:15-22 (1984).
Narayan et al. "Impact of recent increase in incidence on future diabetes burden." Diabetes Care 29:2114, 2006.
Naslund E et al. "GLP-1 slows solid gastric emptying and inhibits insulin, glucagon, and PYY release in humans." Am J Physiol (Regulatory Integrative Comp Physiol 46):R910, 1999.
Naslund E et al. "Prandial subcutaneous injections of glucagon-like petide-1 cause weight loss in obese human subjects." Br J Nutrition 91:439, 2004.
International Search Report mailed on Nov. 21, 2013 for International Application No. PCT/US2013/057397 filed on Aug. 29, 2013.
Eavarone et al., A voxel-based monte carlo model of drug release from bulk eroding nanoparticles. Journal of Nanoscience and Nanotechnology, vol. 10, pp. 5903-5907 (2010).
Marino MT, Cassidy JP, Smutney CC, et al. Improvement in bioavailability of FDKP with the NexGen2A device: Implications for delivery of pulmonary insulin. Diabetes Technology Meeting 2009; poster.
Johnson et al., "Turbuhaler a new device for dry powder terbutaline inhalation", Allergy 43(5):392-395 (1988).
Johnson et al: RyR2 and calpain-10 delineate a novel apoptosis pathway in pancreatic islets. J Biol Chem., 279 (23):24794-802, 2004.
Johnson, Keith A., Preparation of peptide and protein powders for inhalation. Advanced Drug Delivery Reviews 1997; 26:3-15.
Jones et al., An investigation of the pulmonary absorption of insulin in the rat. Third European Congress of Biopharmaceutics and Pharmacokinetics, (1987).
Joseph et al. "Oral delivery of glucagon-like peptide-1 in a modified polymer preparation normalizes basal glycaemia in diabetic db/db mice." Diabetologia 43:1319-1328, 2000.
Joy et al. "Incretin mimetics as emerging treatments for type 2 diabetes." Annal Pharmacother 39:110, 2005.

(56) References Cited

OTHER PUBLICATIONS

Juntti-Berggren et al. "The antidiabetogenic effect of GLP-1 is maintained during a 7-day treatment period and improves diabetic dyslipoproteinemia in NIDDM patients." Diabetes Care 19:1200-1206, 1996.
Kanse et al. "Identification and characterization of glucagon-like peptide-1 7-36 amide-binding sites in the rat brain and lung." FEBS Letters 241:209, 1988.
Kapitza C et al. "Impact of particle size and aerosolization time on the metabolic effect of an inhaled insulin aerosol." Diabetes Tech Ther 6:119, 2004.
Kapitza et al. "Dose-response characteristics for a new pulmonary insulin formulation and inhaler." Presented at the 35th Annual Meeting of the EASD, Sep. 2000, abstract OP29 184.
Kapsner P, Bergenstal RM, Rendell M, et al. Comparative efficacy and safety of Technosphere® insulin and a rapid-acting analog both given with glargine in subjects with type 1 diabetes in a 52-week study. Diabetologia 2009; 52 (suppl 1).
Katchalski E et al. "Synthesis of lysine anhydride", J. Amer Chem Soc 68:879-880, 1946.
Katz et al. "Quantitative insulin sensitivity check index: a simple, accurate method for assessing insulin sensitivity in humans." J. Clin. Endocrinol. Metab. 85:5402-2410, 2000.
Kaur et al. "A Delineation of Diketopiperazine Self-Assembly Processes: Understanding the Molecular Events Involved in Ne-(Fumaroyl)diketopiperazine of L-Lys (FDKP) Interactions." Molecular Pharmaceutics, vol. 5, No. 2, 294-315, Accepted 2007, published on web 2008.
Kawai et al. "Evidence that glucagon stimulates insulin secretion through its own receptor in rats." Diabetologia 38:274, 1995.
Kawamori et al. "Does hyperinsulinemia accelerate atherosclerosis?" Department of Medicine, Juntendo University School, vol. 13, No. 12, p. 954-960, 1994.
Kelley, D. et al. "Impaired postprandial glucose utilization in non-insulin dependent diabetes mellitus." Metabolism 43:1549-1557, 1994.
Kenny AJ et al. "Dipeptidyl peptidase IV, a kidney brush-border serin peptidase." Biochem J. 155:169, 1976.
Kim et al. "Development and characterization of a glucagon-like peptide 1-albumin conjugate. The ability to activate the glucagon-like peptide 1 receptor in vivo." Diabetes 52:751, 2003.
Kinzig et al. "The diverse roles of specific GLP-1 receptors in the control of food intake and the response to visceral illness." J Neurosci 22:10470, 2002.
Kirk et al. "Disparities in HbA1c levels between African-American and non-hispanic white adults with diabetes." Diabetes Care 29:2130, 2006.
Kitabchi, Proinsulin and C-peptide:a review. May 26, 1977 (5):547-87, http://www/ncbi.nlm.nih.gov/pubmed/403392.
Klinger et al., Insulin-micro and nanoparticles for pulmonary delivery. International Journal of Pharmaceutics, vol. 377, pp. 173-179 (2009).
Knop et al. "No hypoglycemia after subcutaneous administration of glucagon-like peptide-1 in lean type 2 diabetic patients and in patients with diabetes secondary to chronic pancreatitis." Diabetes Care 26:2581, 2003.
Knop et al. "Reduced incretin effect in type 2 diabetes. Cause or consequence of the diabetic state?" Diabetes 56:1951, 2007.
Kohler D et al. Non-radioactive approach for measuring lung permeability: inhalation of insulin. Atemw Lungenkrkh 13:230-232, 1987. (English translation attached).
Kohler, "Aerosols for Systemic Treatment", Lung (Suppl.) 677-684 (1990).
Komada et al., Intratracheal delivery of peptide and protein agents: absorption from solution and dry powder by rat lung. J. Pharm. Sci. 83(6): 863-867 (1994).
Komatsu et al. "Glucagonostatic and insulinotropic action of glucagon-like peptide-1 (7-36)-amide." Diabetes 38:902, 1989.
Koning et al., Relationship between inspiratory flow through simulated dry powder inhalers and peak maximal inspiratory pressure. Flow Through a Simulated DPI, Chapter 3, pp. 43-56 (2001).
Labiris et al., Pulmonary drug delivery. Part I: Physiological factors affecting therapeutic effectiveness of aerosolized medications. British Journal of Clinical Pharmocology 56: 588-599 (2003).
Kontny et al., Issues Surrounding MDI Formulation Development with Non-CFC Propellants), J. Aerosol Med 4(3), 181-187 (1991).
Kopple et al. "A convenient synthesis of 2,5-piperazinediones." J Org Chem p. 962, 1967.
Kraft KS, Grant M. Preparation of macromolecule-containing drug powders for pulmonary delivery Methods in Molecular Biology 2009;480:165-174.
Kreymann B et al. "Glucagon-like peptide-1 7-36: a physiological incretin in man." The Lancet, Dec. 5, 1987, p. 1300.
Krssak, M. et al. "Alterations in postprandial hepatic glycogen metabolism in type 2 diabetes." Diabetes 53:3048-3056, 2004.
Krueger et al. "Toxicological profile of pulmonary drug delivery agent." Presented at the American Diabetes Association 64th Scientific Sessions, Jun. 2004, abstract 465-P.
Kwon et al. "Signaling elements involved in the metabolic regulation of mTOR by nutrients, incretins, and growth factors in islets." Diabetes 53:S225, 2004.
Lankat-Buttgereit B et al. "Molecular cloning of a cDNA encoding for the GLP-1 receptor expressed in rat lung." Exp Clin Endocrinol 102:241, 1994.
Laureano et al. "Rapid absorption and elimination of insulin from the lung following pulmonary administration of Technosphere®/Insulin: A pharmacokinetic study in a rat model." Presented at the American Diabetes Association 65th Scientific Sessions, Jun. 2005, abstract 445-P.
Leahy et al. Beta-cell dysfunction in type II diabetes mellitus. Curr Opin Endocrinol Diabetes 2:300-306, 1995.
Lebovitz "Therapeutic options in development for management of diabetes: pharmacologic agents and new technologies." Endocr Pract 12:142, 2006.
Lee et al. "Synthesis, characterization and pharmacokinetic studies of PEGylated glucagon-like peptide-1." Bioconjugate Chem 16:377, 2005.
Lee et al., "Development of an Aerosol Dosage Form Containing Insulin", J. Pharm. Sci. 65(4), 567-572 (1976).
Leiner et al. "Particles facilitate the absorption of insulin in a primary cell culture model of alveolar epithelium without evidence of cytotoxicity." Presented at the American Diabetes Association 64th Scientific Sessions, Jun. 2004, abstract 467-P.
Leiner et al. "The pharmacokinetic profile of insulin administered by inhalation in the rat." Diabetes 53 Supplement, Jun. 2004, A111.
Leone-Bay et al. "Evaluation of novel particles as an inhalation system for GLP-1." Diabetes, Obesity and Metabolism. 11:1050-1059, 2009.
Leone-Bay A, Grant M. Technosphere® Technology: A Platform for inhaled protein therapeutics. OndrugDelivery 2006 (published online).
Leone-Bay A, Grant M. Technosphere®/insulin: mimicking endogenous insulin release. In: Rathbone M, Hadgraft J, Roberts M, et al, eds. Modified Release Drug Delivery, 2e. New York, NY: Informa Healthcare USA, Inc; 2008.
Kieffer et al. "The glucagon-like peptides." Endocrine Reviews 20:876, 1999.
Exubera package insert, p. 1, 2008.
Fadl et al., Effects of MDI spray angle on aerosol penetration efficiency through an oral airway cast. Journal of Science, vol. 38, No. 8, pp. 853-864 (2007). Aerosol.
Falsone et al., The Biginelli dihydropyrimidone synthesis using polyphosphate ester as a mild and efficient cyclocondensation/dehydration reagent. Institute of Chemistry, Organic and Bioorganic Chemistry, Karl-Franzens-University, pp. 122-134 (2001).
Farr, S.J. et al., Pulmonary insulin administration using the AERx®system:physiological and physiochemical factors influencing insulin effectiveness in healthy fasting subjects. Diabetes Tech. Ther. 2:185-197, 2000.

(56) References Cited

OTHER PUBLICATIONS

Fehmann et al. "Cell and molecular biology of the incretin hormones glucagon-like peptide-1 and glucose-dependent insulin releasing polypeptide." Endocrine Reviews 16:390, 1995.
Ferrin et al, Pulmonary retention of ultrafine and fine particles in rats. Am. J. Repir. Cell Mol. Biol., pp. 535-542 (1992).
Festa et al., "LDL particle size in relation to insulin, proinsulin, and insulin sensitivity" Diabetes Care, 22 (10):1688-1693 (1999).
Forst et al., "Metabolic Effects of Mealtime Insulin Lispro in Comparison to Glibenclamide in Early Type 2 Diabetes", Exp. Clin. Endocrinol. Diabetes, 2003, 111, 97-103.
Fritsche et al. "Glimepiride Combined with Morning Insulin Glargine, Bedtime Neutral Protamine Hagedorn Insulin, or Bedtime Insulin Glargine in Patients with Type 2 Diabetes." American College of Physicians 2003.
Galinsky et al., A synthesis of diketopiperazine's using polyphosphoric acid. Journal of the American Pharmaceutical Association, vol. 46, No. 7, pp. 391-393 (1957).
Garber, "Premixed insulin analogues for the treatment of diabetes mellitus", Drugs, 66(1):31-49 (2006).
Garg et al. "Improved glycemic control without an increase in severe hypoglycemic episodes in intensively treated patients with type 1 diabetes receiving morning, evening, or split dose insulin glargine." Diabetes Research and Clinical Practice 66 (2004) 49-56.
Garg SK, Kelly W, Freson B, et al. Treat-to-target Technosphere® insulin in patients with type 1 diabetes. ADA 2011; Abstract 941-P.
Garg SK, McGill JB, Rosenstock J, et al. Technosphere® insulin vs insulin lispro in patients with type 1 diabetes using multiple daily injections. ADA, Abstract 917-P (2011).
Gates BJ "Update on advances in alternative insulin therapy." Advances in Pharmacy 1:159-168, 2003.
Glucagon for Injection (1999) glucagon for injection (rDNA origin), pp. 1-7.
Glucagon-like peptide-1; http://en.wikipedia.org/wiki/Glucagon-like peptide-1 (accessed Apr. 24, 2015).
Glucophage Product Insert. Jan. 2009.
Glucotrol Product Insert. Sep. 2006.
Gnudi L, Lorber D, Rosenstock J, et al. Basal/bolus with prandial inhaled Technosphere® insulin (TI) plus insulin glargine qd vs biaspart 70/30 insulin bid in type T2 diabetes mellitus inadequately controlled on insulin with/without oral agents. Diabetologia 2009; 52 (suppl 1).
Goke et al., Exendin-4 is a high potency agonist and truncated exendin-(9-39)-amide an antagonist at the glucagon-like peptide 1-(7-36)-amide receptor of insulin-secreting beta-cells. J. Biol. Chem. 268(26):19650-19655 (1993).
Golpon et al. "Vasorelaxant effect of glucagon-like peptide-(7-36) amide and amylin on the pulmonary circulation of the rat." Regulatory Peptides 102:81, 2001.
Gonzalez et al., Actualizacion del tratamiento farmacologico de la diabetes mellitus tipo 2. Del Sistema Nacional de Salud. Volumen 32, No. 1, pp. 3-16 (2008)—full article in Spanish with English abstract.
Gotfried M, Cassidy JP, Marino MT, et al. Lung deposition and absorption of insulin from Technosphere® insulin. Diabetologia 2009; 52 (suppl 1).
Grant et al "Both insulin sensitivity and maximal glucose elimination rate are reduced in type 2 diabetes." Presented at the American Diabetes Association 65th Scientific Sessions, Jun. 2005, abstract 2202-PO.
Grant et al. "The distribution of 14C-labeled particles following intra-tracheal liquid installation in the Sprague-Dawley rat." Presented at the American Diabetes Association 64th Scientific Sessions, Jun. 2004, abstract 461-P.
Grant M, Harris E, Leone-Bay A, Rousseau K. Technosphere®/insulin: Method of action. Diabetes Technology Meeting 2006; Poster.
Grant ML, Greene S, Stowell GW, et al. Mimicking endogenous peptide secretion by inhalation APS 2009; poster.

Greene et al. "Effects of GLP-1 Technosphere(TM) powder: administered by pulmonary insufflation in male obese Zucker diabetic fat (ZDF) rats." Diabetes Technology Meeting, San Francisco, Oct. 2007.
Greene et al., Greene's protective groups in organic synthesis. 4th ed., pp. 781-783 (2007).
Gupta et al. "Contemporary Approaches in Aerosolized Drug Delivery to the Lung." J. Controlled Research, 17:129-148, 1991.
Gurrieri et al., Thermal condensation of some alpha-aminoacids with phatalic acid. Thermochimica Acta, 7 (1973) 231-239.
Gutniak et al. "Antidiabetogenic action of glucagon-like peptide-1 related to administration relative to meal intake in subjects with type 2 diabetes." J Int Med 250:81, 2001.
Gutniak et al. "Antidiabetogenic effect of glucagon-like peptide-1 (7-36)amide in normal subjects and patients with diabetes mellitus." NEJM 326:1316, 1992.
Gutniak et al. "GLP-1 tablet in type 2 diabetes in fasting and postprandial conditions." Diabetes Care 20:1874, 1997.
Gutniak et al. "Potential therapeutic levels of glucagon-like peptide I achieved in humans by a buccal tablet." Diabetes Care 19:843, 1996.
Gutniak et al. "Subcutaneious injection of the incretin hormone glucagon-like peptide 1 abolishes postprandial glycemia in NIDDM." Diabetes Care 17:1039, 1994.
Guyton et al., "Acute Control of Llocal Blood Flow", Textbook of Medical Physiology, Chapter 17, 10th Edition, W.B. Saunders Company, pp. 176-177, 2000.
Gyore et al., Thermal Analysis, vol. 2—Proceedding Fourth ICTA Budapest 1974; 387-394.
Haak "New developments in the treatment of type 1 diabetes mellitus." Exp Clin Endocrinol Diabetes 107:Suppl 3:S108, 1999.
Haffner et al., "Proinsulin and insulin concentrations I relation to carotid wall thickness", Strock 29:1498-1503 (1998).
Hagedorn et al. "Protamine Insulin", JAMA, 106:177-180 (1936).
Haino, Takeharu et al. "On-beads Screening of Solid-Attached Diketopiperzines for Calix[5]Arene-Based Receptor." Tetrahedron Letters, 40(20), 3889-3892, 2003.
Hanley et al., "Cross-sectional and prospective associations between proinsulin and cardiovascular disease risk factors in a population experiencing rapid cultural transition" Diabetes Care 24(7): 1240-1247 (2001).
Harsch IA "Inhaled insulins. Their potential in the treatment of diabetes mellitus." Traat. Endicrinol 4:131-138, 2005.
Hassan et al. "A Randomized, Controlled Trial Comparing Twice-a-Day Insulin Glargine Mixed with Rapid-Acting Insulin Analogs Versus Standard Neutral Protamine Hagedorn (NPH) Therapy in Newly Diagnosed Type 1 Diabetes." Pediatrics, 121(3), e466-e472, 2008.
Hassan et al. "In vivo dynamic distribution of 131l-glucagon0like peptide-1 (7-36) amide in the rat studied by gamma camera." Nucl Med Biol 26:413, 1999.
Hausmann et al. "Inhaled insulin as adjunctive therapy in subjects with type 2 diabetes failing oral agents: a controlled proof of concept study." Diabetes Obesity and Metabolism 8:574, 2006.
Hayasaka et al. "Proliferation of type II pneumocytes and alteration in their apical surface membrane antigenicity in pulmonary sarcoidosis." Chest 116:477, 1999.
Heine "Unlocking the opportunity of tight glycaemic control. Promise ahead: the role of inhaled insulin in clinical practice." Diabetes, Obesity and Metabolism 7:S19, 2005.
Heinemann "Variability of Insulin Absorption and Insulin Action." Diabetes Technology & Therapeutics, vol. 4, No. 5, pp. 673-682. 2002.
Heinemann et al. "Current status of the development of inhaled insulin." Br. J. Diabetes Vasc. Dis. 4:295-301, 2004.
Heinemann L et al. "Time-action profile of inhaled insulin." Diabetic Med 14:63-72, 1997.
Heinemann, L. "Intra-individual Variability of the Metabolic Effect of Inhales Insulin Together with an Absorption Enhancer", Diabetes Care, vol. 23, No. 9, Sep. 2000, p. 1343-1347.
Heise et al. "The effect of insulin antibodies on the metabolic action of inhaled and subcutaneous insulin." Diabetes Care 28:2161, 2005.

(56) References Cited

OTHER PUBLICATIONS

Herbst et al., Insulin Strategies for Primary Care Providers. Clinical Diabetes, vol. 20, No. 1, pp. 11-17 (2002).
Heubner et al. "On inhalation of insulin" Klinische Wochenschrift 16:2342, 1924. (Original and English translation provided in one document).
Heyder "Particle Transport onto Human Airway Surfaces", Eur. J. Respir. Dis, Suppl. 119, 29-50 (1982).
Heyder, "Alveolar deposition of inhaled particles in humans", Am. Ind. Hyg. Assoc. J. 43(11): 864-866 (1982).
Hirsch IB "Insulin analogues." N Engl J Med 352:174-83, 2005.
Hirsch, "Type 1 Diabetes Mellitus and the Use of Flexible Insulin Regimens" American Family Phyician, Nov. 15, 1999, p. 1-16.
Hirshberg B et al. "Islet transplantation: where do we stand now?" Diabetes Metab Res Rev 19:175-8, 2003.
Hite et al. "Exhuberance over Exubera." Clin Diabetes 24(3):110-114, 2006.
Hoet et al., Review: Nanoparticles—known and unknown health risks. Journal of Nanobiotechnology, vol. 2, No. 12, (15 pages) (2004).
Hollander et al. "Efficacy and Safety of Inhaled Insulin (Exubera) Compared with Subcutaneous Insulin Therapy in Patients with Type 2 Diabetes." Diabetes Care, vol. 27, No. 10, Oct. 2004, p. 2356-2362.
Holst "Therapy of type 2 diabetes mellitus based on the actions of glucagon-like peptide-1." Diabetes Metab Res Rev 18:430, 2002.
Holst et al. "On the effects of glucagon-like peptide-1 on blood glucose regulation in normal and diabetic subjects." Ann N Y Acad Sci. Dec. 26, 1996;805:729-36.
Howard C, Ren H, Rossiter A, et al. Reduced incidence and frequency of hypoglycemia in an integrated analysis of pooled data from clinical trials of subjects with type 1 diabetes using prandial inhaled Technosphere® insulin. Diabetologia 2009; 52 (suppl 1).
Howard CP, Gnudi L, Lorber D, et al. Prandial inhaled Technosphere® insulin plus insulin glargine vs. biaspart 70/30 insulin in type 2 diabetes inadequately controlled with/without oral agents. Third International Conference on Advanced Technologies and Treatments for Diabetes. 2010; Poster 300.
Howard CP, Lorber D, Ren H, et al. Reduced incidence and frequency of hypoglycemia in pooled data from trials of type 2 diabetics using prandial inhaled Technosphere® insulin. Third International Conference on Advanced Technologies and Treatments for Diabetes 2010; Poster 304.
Howard CP, Petrucci R, Amin N, et al. Pulmonary function test remain similar in patients who received Technosphere® insulin and in patients currently receiving standard antidiabetic therapy. AACE 2010; Poster 267.
Howard CP, Ren H, Rossiter A, Boss AH. Reduced incidence and frequency of hypoglycemia in pooled data from trials of type 1 diabetics using prandial inhaled Technosphere® insulin. Third International Conference on Advanced Technologies and Treatments for Diabetes. 2010; Poster 302.
Howard CP, Ren H, Rossiter A, et al. Reduced incidence and frequency of hypoglycemia in an integrated analysis of pooled data from clinical trials of subjects with type 1 diabetes using prandial inhaled Technosphere® insulin. AACE 2010; Poster 269.
Howard CP, Rubin RR, Peyrot. M. Patient reported outcomes in adults with type 2 diabetes using mealtime AFRESA® (inhaled Technosphere® insulin) and basal insulin versus premixed insulin ADA 2009; Poster 551.
Huda et al. "Gut peptides and the regulation of appetite." Obesity Reviews 7:163, 2006.
Hui et al., The short half-life of glucagon-like peptide-1 in plasma does not reflect its long-lasting beneficial effects. European Journal of Endocrinology, 146: 863-869 (2002).
Hussain et al. "State of insulin self-association does not affects its absorption from the pulmonary route." Eur. J. Pharm. Sciences 25:289-298, 2005.

Ikeda, Kuniki et al. "Peptide Antibiotics. XXVI. Syntheses of Cyclodipeptides Containing N. delta.-p-aminobenzenesulfonyl Ornithine Residue." Chemical & Pharmaceutical Bulletin, 20(9), 1849-55, 1972.
Imeryuz et al. "Glucagon-like peptide-1 inhibits gastric emptying via vagal afferent-mediated central mechanisms." Am J Physiol 273 (Gastrointest Liver Physiol 36):G920, 1997.
Insulin inhalation NN 1998, Drugs R & D, 2004, pp. 46-49, Adis Data Information BV.
Insulin is a natural product from http://www.levemir.com/startingoninsulin/whatisinulin.aspx, pp. 1-3. Accessed by Examiner on Apr. 30, 2014 and in Non-Final Office Action dated May 22, 2014 for U.S. Appl. No. 13/797,657 and in Non-Final Office Action dated May 22, 2014 for U.S. Appl. No. 12/883,369.
International Search Report for PCT International Application No. PCT/US2010/055323 filed on Nov. 3, 2010.
Written Opinion mailed on Jul. 1, 2013 for International Application No. PCT/US2013/032162 filed on Mar. 15, 2013.
International Search Report mailed on Jun. 21, 2010 for International Application No. PCT/US2010/027038 filed on Mar. 11, 2010.
Written Opinion for International Application No. PCT/US2011/060057 filed on Nov. 9, 2011.
International Search Report mailed Mar. 18, 2013 for International Application No. PCT/US2012/061749 filed on Oct. 24, 2012.
International Search Report mailed on Jun. 20, 2012 for International Applicaion No. PCT/US2012/031695 filed on Mar. 30, 2012.
International Search Report mailed on Nov. 19, 2014 for International Application No. PCT/US2014/049817 filed on Aug. 5, 2014.
International Search Report for International Application No. PCT/US2010/020448 filed on Jan. 8, 2010.
International Search Report mailed on Mar. 11, 2010 for International Application No. PCT/US2009/069745 filed on Dec. 29, 2009.
International Search Report mailed on Oct. 17, 2011 for International Application No. PCT/US2010/026271 filed on Mar. 4, 2010.
International Search Report for International Application No. PCT/US2010/038287 filed on Jun. 11, 2010.
Ishibashi, Norio et al. "Studies on Flavord Peptides. Part V. A Mechanism for Bitter Taste Sensibility in Peptides." Agricultural and Biological Chemistry, 52(3), 819-27, 1988.
Iwanij et al., Characterization of the Glucagon Receptor and its Functional Domains Using Monoclonal Antibodies. The Journal of Biological Chemistry, vol. 265, No. 34, pp. 21302-21308, 1990.
Jain et al. "Insulin Therapy in Type 2 Diabetic Subjects Suppresses Plasminogen Activator Inhibitor (PAI-1) Activity and Proinsulin-like Molecules Independently of Glycaemic Control." Diabetic Medicine, vol. 10, No. 1, p. 27-32, 1993.
Johnson et al., Peptide turn mimetics. Biotechnology and Pharmacy, p. 366-378 (1993).
International Search Report for International Application No. PCT/US2013/050392 filed on Jul. 12, 2013.
Nathan DM et al. "Management of hyperglycemia in Type 2 diabetes: a consensus algorithm for the initiation and adjustment of therapy." Diabetes Care 29:1963-1972, 2006.
Nathan DM et al. "Management of hyperglycemia in Type 2 diabetes: a consensus algorithm for the initiation and adjustment of therapy." Diabetes Care 31:173-175, 2008.
Nathan DM et al. "Management of hyperglycemia in Type 2 diabetes: a consensus algorithm for the initiation and adjustment of therapy." Diabetes Care 32:193-203, 2009.
Nathan et al. "Intensive diabetes treatment and cardiovascular disease in patients with Type 1 diabetes." New Eng. J. Med. 353:2643-2653, 2005.
Nathan, "Initial Management of Glycemia in Type 2 Diabetes Melllitus" N. Eng. J. Med., 2002, 347, 1342-9.
Nauck "Is glucagon-like peptide 1 an incretin hormone?" Diabetologia 42:373-379, 1999.
Nauck et al. "Glucagon-like peptide 1 inhibition of gastric emptying outweighs its insulinotropic effects in healthy humans." Am J Physiol 273 (Endocrinol Metabl 36):E981, 1997.
Nauck et al. "Reduced incretin effect in type 2 (non-insulin-dependent) diabetes." Diabetologia 29:46-52, 1986.
Nauck et al., Effects of glucagon-like peptide 1 on counterregulatory hormone responses, cognitive functions, and insulin secretion dur-

(56) References Cited

OTHER PUBLICATIONS ing hyperinsulinemic, stepped hypoglycemic clamp experiments in healthy volunteers. J Clin Endocrinol Metab., 87:1239-1246, 2002.
Nauck et al., Effects of subcutaneous glucagon-like peptide 1 (GLP-1 [7-36 amide]) in patients with NIDDM. Diabetologia, 39:1546-1553, 1996.
Nauck et al., Normalization of fasting hyperglycemia by exogenous GLP-1 (7-36 amide) in type 2 diabetic patients. Diabetologia, 36:741-744, 1993.
Nemmar et al., Passage of inhaled particles into the blood circulation in humans. Circulation pp. 411-414 (2002).
Newman, Principles of metered-dose inhaler design. Respiratory Care, vol. 50, No. 9, pp. 1177-1190 (2005).
Next Generation Inhaler Nears Market, Manufacturing Chemist, Cambridge Consultants, Polygon Media Ltd. (2006).
NHS Clinical Guidelines, "Type 1 diabetes diagnosis and mangement of type 1 diabetes in children and young people", National Collaborating Centre for Women's and Children's Health Commissioned by the National Institute for Clinical Excellence, Sep. 2004, p. 1-217.
Non-covalent interactions from UC Davis ChemWiki, pp. 1-5. Accessed by Examiner on Jul. 23, 2013 and related case U.S. Appl. No. 12/830,557.
Nystrom et al. "Effects of glucagon-like peptide-1 on endothelial function in type 2 diabetic patients with stable coronary artery disease." Am J Physiol Endocrinol Metabl 287:E1209, 2004.
Oberdorster et al., Correlation between particle size, in vivo particle persistence, and lung injury. Environ Health Perspect 102 Suppl 5, pp. 173-179 (1994).
Oberdorster et al., Pulmonary effects of inhaled ultrafine particles. International Archives of Occupational and Environmental Health, vol. 74, pp. 1-8 (2001).
Okumura et al., Intratracheal delivery of insulin: absorption from solution and aerosol by rat lung. Int. J. Pharmaceuticals 88: 63-73 (1992).
O'Neill, Air pollution and inflammation in type 2 diabetes: a mechanism for susceptibility. Occup Environ Med. vol. 64, pp. 373-379 (2007).
Orgsoltab et al., Division of Organic Chemistry. Ohio Northern University. Nov. 24, 2009. Available from: <http://www.2.onu.edu/~b-meyers/organic_solvents.html>.
Oshima et al. "Comparison of half-disappearance times, distribution volumes and metabolic clearance rates of exogenous glucagon-like peptide 1 and glucagon in rats." Regulatory Peptides 21:85, 1988.
Ostrovsky, Gene. Mannkind Inhalation Insulin Going to FDA to Seek Approval [on-line]. MedGadget.com, posted on Mar. 17, 2009, Retrieved from the Internet: <URL:http://medgadget.com/2009/03mannkind_inhalation_insulin_going_to_fda_to_seek_approval.html>.
Owens et al. "Inhaled human insulin." Nature Reviews, Drug Discovery, vol. 5, No. 5, pp. 371-372, May 2006.
Owens et al. "Alternative routes of insulin delivery." Diabetic Medicine 20:886-898, 2003.
Ozyazgan et al. "Effect of glucagon-like peptide-1)7-36) and exendin-4 on the vascular reactivity in streptozotocin/nicotinamide-induced diabetic rats." Pharmacology 74:119, 2005.
Pacini P, Marino MT. Evaluation of endogenous and exogenous components to peripheral insulin concentration during administration of inhaled insulin. ADA 2010; Abstract 2094-PO.
Patton "Mechanisms of macromolecule absorption by the lungs." Advanced Drug Delivery Reviews 19:3, 1996.
Patton "Unlocking the opportunity of tight glycaemic control. Innovative delivery of insulin via the lung." Diabetes Obesity and Metabolism 7:S5, 2005.
Patton & Platz, Routes of Delivery: Case studies: pulmonary delivery of peptides and proteins for systemic action. Adv. Drug. Del. Rev. 8: 179-196 (1992).
Patton et al. "The lungs as a portal of entry for systemic drug delivery." Proc Am Thorac Soc 1:338, 2004.

Patton et al. "Clincal pharmacokinetics and pharmacodynamics of inhaled insulin." Clin Pharmacokinet 43:781-801, 2004.
Patton et al., "Inhaled Insulin", Advanced Drug Delivery Reviews, 35, Feb. 1999, p. 235-247.
Onoue et al., Dry powder inhalation systems for pulmonary delivery of therapeutic peptides and proteins. Expert Opin. Ther. Patents 18(4):429-442 (2008).
Pearson et al., Systematically Initiating Insulin, supplemental to vol. 32, No. 1, 19S-28S, 2006.
Perera et al. "Absorption and Metabolic Effect of Inhaled Insulin." Diabetes Care, vol. 25, No. 12, Dec. 2002, p. 2276-2281.
Pesic, Inhaler delivers more drug to the deep lung, says Cambridge Consultants. in-Pharma Technologist.com, http://www/in-pharmatechnologist.com/content/view/print/344335, Dec. 1, 2010.
Petkowicz et al., "Hypoglycemic effect of liposome-entrapped insulin adminstered by various routes into normal rats", Pol. J. Pharmacol. Pharm. 41:299-304 (1989).
Petrucci R, Amin N, Lovertin P. et al. Pulmonary function tests remain similar in patients who received Technosphere® insulin and in patients currently receiving standard antidiabetic therapy. Diabetologia 2009; 52 (suppl 1).
Peyrot et al. "Resistance to insulin therapy among patients and providers." Diabetes Care 28:2673-2679, 2005.
Peyrot M, Rubin RR, Otterbach K. Effect of Technosphere® inhaled insulin on treatment satisfaction, glycemic control and quality of life. Diabetes 2006; 55:Abstract 423-P.
Pezron et al., Insulin aggregation and asymmetric transport across human bronchial epithelial cell monolayers (Calu-3). J. Pharmaceutical Sci. 91: 1135-1146 (2002).
Pfeiffer MA et al. Insulin secretion in diabetes mellitus. Am J Med 70:579-88, 1981.
Pfutzner et al., Abstract 812: Influence of small dose i.v.s.c. and pulmonary insulin treatment on grandial glucose control in patients with type 2 diabetes. Internet Article [Online] 2001, 37th Annual Meeting of the EASD, Glasgow, Sep. 9-13, 2001.
Pfutzner A et al. "Pulmonary insulin delivery by means of the Technosphere(TM) drug carrier mechanism." Expert Opin Drug Deliv 2:1097-1106, 2005.
Pfützner A et al. "Technosphere®/Insulin—a new approach for effective delivery of human insulin via the pulmonary route." Diab Tech Ther 4:589-594, 2002.
Pfützner A et al. "Lung distribution of radiolabeled Technosphere™/Insulin." Diabetes 52 Supplement, Jun. 2003, A107.
Pfützner A et al. Pilot study with Technosphere/PTH(1-34)—a new approach for effective pulmonary delivery of parathyroid hormone (1-34). Horm Metab Res 35:319-323, 2003.
Pfützner A et al. "Variability of insulin absorption after subcutaneous and pulmonary application in patients with type 2 diabetes." Diabetes 51 Supplement, Jun. 2002, A47-48.
Bilheimer DW, Ren H, Boss AH. Analysis of cardiovascular adverse events in patients with type 1 or type 2 diabetes enrolled in selected therapeutic trials in the phase 2/3 Technosphere® insulin development program. ADA 2011. Poster 922-P.
Billings CC, Smutney CC, Howard CP, et al. Handleability and characterization of inhalation profiles using the Gen2 delivery system in a pediatric population. Diabetes Technology Meeting 2010; poster.
Biodel's Intellecutal Property position strengthened for ultra-rapid-acting insulin programs by notice of intent to grant from European Patent Office. Newswire Feed, published May 2, 2012.
Blazquez E et al. "Glucagon-like peptide-1 (7-36) amide as a novel neuropeptide." Mol Neurobio 18:157, 1998.
Bloomgarden "Gut-derived incretin hormones and new therapeutic approaches." Diabetes Care 27:2554, 2004.
Boer et al., Design and application of a new modular adapter for laser diffraction characterization of inhalation aerosols. International Jornal of Pharmaceutics 249, pp. 233-245 (2002).
Boer et al., Inhalation characteristics and their effects on in vitro drug delivery from dry powder inhalers. Part 1. Inhalation characteristics, work of breathing and volunteers' preference in dependence of the inhaler resistance. Int. J. Pharm. 130 (1996) 231-244.

(56) References Cited

OTHER PUBLICATIONS

Bojanowska "Physiology and pathophysiology of glucagon-like peptide-1 (GLP-1): the role of GLP-1 in the pathogenesis of diabetes mellitus, obesity and stress." Med Sci Monit 11:RA271, 2005.
Bonner-Weir S et al. "New sources of pancreatic beta-cells." Nat Biotechnol 23:857-61, 2005.
Boss AH et al. "Inhaled Technosphere®/Insulin: Glucose elimination at the right time?" Poster presented at the American Diabetes Association 65th Scientific Sessions, Jun. 2005, abstract 443-P.
Boss AH et al. "Insulin bio-effect is limited by speed of absorption and elimination: similarities between an inhaled insulin formulation that mimics first-phase kinetics and i.v. insulin." Diabetologia 47:A314, 2004.
Boss AH et al. "Mimicry of the early phase insulin response in humans with rapidly available inhaled insulin accelerates post prandial glucose disposal compared to slower bioavailable insulin." Presented at the American Diabetes Association 65th Scientific Sessions, Jun. 2005, abstract 1373-P.
Boss AH et al. "Does kinetics matter? Physiological consequences of the ability of Technosphere®/Insulin inhalation to mimic first phase insulin release." Presented at the 5th Annual Meeting of the Diabetes Technology Society, Nov. 2005, abstract A14.
Boss AH et al. "Markedly reduced post prandial glucose excursions through inhaled Technosphere®/Insulin in comparison to SC injected regular insulin in subjects with type 2 diabetes." 1st Annual Meeting of the European Association for the Study of Diabetes, Sep. 2005, abstract 816.
Boss AH et al. "The variability and time-action profile of inhaled Technosphere®/Insulin compares favorably to that of subcutaneous human regular insulin." Presented at the American Diabetes Association 65th Scientific Sessions, Jun. 2005, abstract 358-OR.
Boss et al. "Prandial Insulin: Is Inhaled Enough?" Drug Development Research 69(3):138-142 (2008).
Boss A H, Petrucci R, Lorber D. Coverage of prandial insulin requirements by means of an ultra-rapid-acting inhaled insulin. Journal of diabetes science and technology 2012;6:773-779.
Boss AH, Baughman RA, Evans SH, et al. A 3 month comparison in type 1 diabetes of inhaled Technosphere®/Insulin (TI) to Sc administered rapid-acting insulin analogue (RAA) as prandial insulin in a basal/prandial regimen. Diabetes 2006; 55:A97.
Boss AH, Evans SH, Firsov I, et al. Technosphere® insulin as effective as sc rapid acting insulin analogue in providing glycemic control in a 6-month study of patients with type 2 diabetes. Diabetes Technology Meeting 2006; poster.
Boss AH, Evans, SH, Ren, H, et al. Superior post prandial glucose control in patients with type 1 diabetes when using prandial technosphere insulin compared to NovoLog. Diabetologia 2006; Abstract 181.
Boss AH, Marino MT, Cassidy JP, et al. C-peptide correction method to determine exogenous insulin levels in pharmacokinetic studies using Technosphere® insulin. Diabetologia 2009; 52 (suppl 1).
Boss AH, Raskin P, Philips M, et al. Glycosylated hemoglobin and hypoglycaemia in patients with Type 2 diabetes mellitus: Technosphere® insulin and usual antihyperglycaemic regimen vs usual antihyperglycaemic regimen. Diabetologia 2010;53(suppl 1).
Brandt D, Boss AH. The next generation insulin therapy. OndrugDelivery 2006 (published online).
Brange et al., "Insulin Structure and Stability", Pharm Biotechnol, 5:315-50 (1993).
Bray "Exanatide" Am J Health-Sys Pharm 63:411, 2006.
Brownlee et al. "Glycemic variability: a hemoglobin A1c-independent risk factor for diabetic complications." JAMA 295:1707, 2006.
Bruce, D.G., et al. "Physiological importance of deficiency of early prandial insulin secretion in non-insulin-dependent diabetes." Diabetes 37:736-44, 1988.
Bullock BP et al. "Tissue distribution of messenger ribonucleic acid encoding the rat glucagon-like peptide-1 receptor." Endocrinology 137:2968, 1996.
Burcelin et al. "Encapsulated, genetically engineered cells, secreting glucagon-like peptide-1 for the treatment of non-insulin-dependent diabetes mellitus." Ann N Y Acad Sci. Jun. 18, 1999;875:277-85.
Calles-Escandon, J. and Robbins, D.C. "Loss of early phase insulin release in humans impairs glucose tolerance and blunts thermic effect of glucose." Diabetes 36:1167-72, 1987.
Camilleri, Clinical Practice: Diabetic Gastroparesis. The New England Journal of Medicine, 356: 820-829 (2007).
Campos et al. "Divergent tissue-specific and developmental expression of receptors for glucagon and glucagon0like peptide-1 in the mouse." Endocrinology 134:2156, 1994.
Cassidy J P, Amin N, Marino M, et al. Insulin lung deposition and clearance following Technosphere® insulin inhalation powder administration. Pharmaceutical Research 2011; 28:2157-2164.
Cassidy J, Amin N, Baughman R, et al. Insulin kinetics following Technosphere® insulin inhalation powder administration unchanged in albuterol-treated asthmatics. ADA 2010; Poster 522.
Cassidy J, Baughman RA, Tonelli G, et al. Use of rapid acting insulin analog as the baseline infusion during glucose clamping improves pharmacokinetic evaluation. ADA 2007; 56: Abstract 602-P.
Cassidy JP, Baughman RA, Schwartz SL, et al. AFRESA® (Technosphere® insulin) dosage strengths are interchangeable ADA 2009; Poster 433.
Cassidy JP, Marino MT, Amin N, et al. Lung deposition and absorption of insulin from AFRESA® (Technosphere® insulin) ADA 2009; Poster 425.
Cassidy JP, Potocka E, Baughman RA, et al. Pharmacokinetic characterization of the Technosphere® inhalation platform Diabetes Technology Meeting 2009. poster.
Caumo et al. "First-phase insulin secretion: does it exist in real life" Considerations on shape and function. Am J Physiol Endocrinol Metab 287:E371-E385, 2004.
Cefalu "Concept, Strategies and Feasibility of Noninvasive Insulin Delivery." Diabetes Care 27:239-246, 2004.
Cefalu "Novel routes of insulin delivery for patients with type 1 or type 2 diabetes." Ann Med 33:579-586, 2001.
Cefalu et al., Inhaled human insulin treatment in patients with type 2 diabetes mellitus. Ann. Int. Med., 2001, 134(3): 203-207.
Ceglia et al. "Meta-analysis: efficacy and safety of inhaled insulin therapy in adults with diabetes mellitus." Ann Intern Med 145:665, 2006.
Cerasi, et al. Decreased sensitivity of the pancreatic beta cells to glucose in prediabetic and diabetic subjects. A glucose dose-response study. Diabetes 21(4):224-34, 1972.
Cernea et al. "Dose-response relationship of oral insulin spray in healthy subjects." Diabetes Care 28:1353-1357, 2005.
Cernea et al. "Noninjectable Methods of Insulin Administration." Drugs of Today 2006, 42 (6): 405-424.
Chan et al., "Pharmacological Management of Type 2 Diabetes Mellitus: Rationale for Rational Use of Insulin", Mayo Clin Proc, 2003, 78, 459-467.
Chase et al., "Redefining the clinical remission period in children with type 1 diabetes", Pediatric Diabetes, 2004, 5, 16-19.
Cheatham et al. "Desirable Dynamics & Performance of Inhaled Insulin Compared to Subcutaneous Insulin Given at Mealtime in Type 2 Diabetes: A Report from the Technosphere/Insulin Study Group." Diabetes Technology and Therapeutics, vol. 6, p. 234 (2004).
Cheatham et al. "A novel pulmonary insulin formulation replicates first phase insulin release and reduces s-proinsulin levels." Presented at the American Diabetes Association 64th Scientific Sessions, Jun. 2004, abstract 457-P.
Cheatham et al. "Prandial Technosphere®/Insulin inhalation provides significantly better control of meal-related glucose excursions than prandial subcutaneous insulin." Presented at the Diabetes Technology Society meeting, Oct. 2004.
Chelikani et al., Intravenous infusion of glucagon-like peptide-1 potently inhibits food intake, sham feeding, and gastric emptying in rats. Am J Physiol. Regul. Integr. Comp. Physiol., 288(6):R1695-706, 2005.
Chemical Abstracts, vol. No. 114(22), Abstract No. 214519x (1990).

(56) References Cited

OTHER PUBLICATIONS

Chemicaland21.com. Solvents. Dec. 12, 2008. Available from: <http://web.archive.org/web20081212035748/http://www.chemicalland21.com/info/SOLVENTS.htm.
Chow et al., Particle Engineering for Pulmonary Drug Delivery. Pharmaceutical Research, vol. 24, No. 3, pp. 411-437 (2007).
Clee et al. Nature Genetics 38:688-693, 2006.
Cobble "Initiating and Intensifying Insulin Therapy for Type 2 Diabetes: Why, When, and How." Am J Ther. Jan. 8, 2009.
Coffey et al. "Valuing heath-related quality of life in diabetes." Diabetes Care 25:2238, 2002.
Colagiuri et al., Are lower fasting plasma glucose levels at diagnosis of type 2 diabetes associated with improved outcomes? Diabetes Care, vol. 25, pp. 1410-1417 (2002).
Combettes and Kargar, C, Newly Approved and Promising Antidiabetic Agents. Therapie, Jul.-Aug. 2007: 62 (4): 293-310.
Coors et al., Polysorbate 80 in medical products and nonimmunologic anaphylactoid reactions. Ann. Allergy Astha Immunol., 95(6): 593-599 (2005).
Costello et al., "Zinc inhibition of mitochondrial aconitase and its importance in citrate metabolism in prostate epithelial cells", Journ. Biol. Chem. 272(46):28875-28881 (1997).
Cricket TM Single-Use Inhalers [on-line]. MannKind Technologies Website, posted in 2011, [retrieved on Jul. 30, 2012]. Retrieved from the Internet. <URL:mannkindtechnologies,com/DeviceTechnology/CricketSingleUseInhalers.aspx>.
Crosby, J. "Dog Normals", <http://vetmedicine.about.com/od/diseasesconditionsfaqs/tp/TP_dogfacts.htm>, copyright 2013.
Cruetzfeldt et al. "Glucagonostatic actions and reduction of fasting hyerglycemia by exogenous glucagon-like peptide i(7-36) amide in type 1 diabetic patients." Diabetes Care 19:580, 1996.
D'Alessio et al., Elimination of the action of glucagon-like peptide 1 causes an impairment of glucose tolerance after nutrient ingestion by healthy baboons. J. Clin. Invest., 97:133-38 (1996).
Database adisinsight, "Gucagon-like peptide-1 inhalation-MannKind Corporation", Database accession No. 2009:1048 Abstract.
Davis "Postprandial Physiology and the Pathogenesis of Type 2 Diabetes Mellitus." Insulin, vol. 3, Apr. 1, 2008, pp. 132-140.
De Heer et al. "Sulfonylurea compounds uncouple the glucose dependence of the insulinotropic effect of glucagon-like peptide-1." Diabetes 56:438, 2007.
Deacon "Therapeutic strategies based on glucagon-like peptide 1." Diabetes. Sep;53(9):2181-9, 2004.
Deacon et al., "Glucagon-like peptide 1 undergoes differential tissue-specific metabolism in the anesthetized pig", Am. J. Physiol. 271 (Endocrino. Metab. 34): E458-E464, 1996.
Decode study group. "Glucose tolerance and mortality: comparison of WHO and American Diabetes Association diagnostic criteria." Lancet. Aug. 21, 1999;354(9179):617-21.
DedicatedPhase, "Preclinical Trials and Research", <http://www.dedicatedphase1.com/preclinical-research.html>, copyright 2006-2011, p. 1.
Definition of analog from http://cancerweb.ncl.ac.uk/omd/about.html, pp. 1-5. Accessed by Examiner on Jul. 7, 2005 and cited in Office Action issued on Jul. 26, 2013 in U.S. Appl. No. 12/830,557.
Del Prato S "Unlocking the opportunity of tight glycemic control" Diabetes Obesity and Metabolism 7:S1-S4, 2005.
Delgado-Aros et al. "Effect of GLP-1 on gastric volume, emptying, maximum volume ingested and postprandial symptoms in humans." Am J Physiol Gastrointest Liver Physiol 282:G424, 2002.
Diabetes: Counting Carbs if You Use Insulin, WedMD, http://diabetes.webmd.com/carbohydrate-counting-for-people-who-use-insulin#m Oct. 1, 2010.
Diez et al. "Inhaled insulin—a new therapeutic option in the treatment of diabetes mellitus" Expert Opin. Pharmacother., 2003, 4, 191-200.
Doyle et al. "Glucagon-like peptide-1." Recent Prog Horm Res. 2001;56:377-99.
Dreamboat TM Reusable Inhalers [on-line]. MannKind Technologies Website, posted in 2011, Retrieved from the Internet: <URL: mannkindtechnologies.com/Device Technology/Dream Boat Reuseable Inhalers.aspx>.
Drucker "Development of glucagon-like peptide-1-based pharmaceuticals as therapeutic agents for the treatment of diabetes." Curr Pharma Design 7:1399, 2001.
Drucker et al., "The incretin system:glucagon-like peptide-1 receptor agonists and dipeptidyl peptidase-4 inhibitors in type 2 diabetes", www.thelancet.com, vol. 368, pp. 1696-1705, Nov. 11, 2006.
Drug Delivery, Easing the drug delivery route, Jun. 2006, Pharmaceutical & Medical Packaging News, Canon Communications.
Dungan et al., Glucagon-like peptide 1-based therapies for type 2 diabetes: a focus on exntadtide. Clinical Diabetes, 23: 56-62 (2005).
Dunn, "Zinc-ligand interactions modulate assembly and stability of the insulin hexamer", Biometals, 18(4):295-303 (2005).
Edelman "Type II Diabetes Mellitus." Adv Int Med, 43:449-500, 1998.
Edited by Fukushima, Masanori, "Arterial Sclerosis," Merck Manual 17th, Japanese Edition, NIKKEI BP Corp., p. 1659-1663, 1999.
Edwards CMB et al. "Cardiovascular and pancreatic endocrine response to glucagon-like peptide-1(7-36) amide in the conscious calf." Exp Physiol 82:709, 1997.
Edwards CMB et al. "Subcutaneous glucagon-like peptide-1(7-36) amide is insulinotropic and can cause hypoglycaemia in fasted healthy subjects." Clinical Science 96:719, 1998.
Edwards et al., Recent advances in pulmonary drug delivery using large, porous inhaled particles. Journal of Applied Physiology, pp. 379-385 (1998).
Eggers et al., Molecular confinement influences protein structure and enhances thermal protein stability. Protein Sci., 10:250-261 (2001).
Ehlers et al. "Recombinant glucagon-like peptide-1 (7-36 amide) lowers fasting serum glucose in a broad spectrum of patients with type 2 diabetes." Horm Metab Res 35:611, 2003.
Eissele et al., Rat gastric somatostatin and gastrin relase: interactions of exendin-4 and truncated glucagon-like peptide-1 (GLP-1) amide. Life Sci., 55(8):629-634 (1994).
Elliot et al., Parenteral absorption of insulin from the lung in diabetic children. Austr. Paediatr. J. 23: 293-297 (1987).
Elrick et al. "Plasma insulin response to oral and intravenous glucose administration." J Clin Endocr 24:1076, 1964.
Engelgau MM "Screening for type 2 diabetes." Diabetes Care 23:1563-1580, 2000.
Engwerda et al., Improved pharmackinetic and pharmacodynamic profile of rapid-acting insulin using needle-free jet injection technology. Diabetes Care, vol. 34, Aug. 2011, pp. 1804-1808.
Erlanger et al., Phosphorous pentoxide as a reagent in peptide synthesis. College of Physicians and Surgeons—Columbia Univeristy, vol. 26, pp. 2534-2536 (1960).
Exubera indications, dosage, storage, stability. Http://www.rxlist.com/cgi/generic4/exubera_ids.htm, 2008.
Shields, Irritable bowel syndrome, archived Jun. 21, 2009, available at: https://web.archive.org/web/200906211 00502/http://www.gastroenterologistpaloalto.com/conditions-diseases-irritable-bowelsyndrome-palo-alto-ca. html; Aug. 26, 2015 is U.S. Appl. No. 14/139,714.
Smith et al., Evaluation of novel aerosol formulations designed for mucosal vaccination against infleunza virus. Vacine, vol. 21, pp. 2805-2812 (2003).
U.S. Appl. No. 14/873,041, filed Oct. 1, 2015.
Design U.S. Appl. No. 29/504,212, filed Oct. 2, 2014.
U.S. Appl. No. 14/774,311, filed Sep. 10, 2015.
U.S. Appl. No. 14/746,656, filed Jun. 22, 2015.
Young et al., Encapsulation of lysozyme in a biodegradable polymer by preparation with a vapor-over-liquid antisolvent. Journal of Pharmaceutical Sciences, 88:640-650 (1999).
Hazard Prevention and Control in the Work Environment: Airborne Dust WHO/SDE/OEH/99. 14 Chapter 1—Dust: Definitions and Concepts [retrieved from internet by Examiner in European case on

(56) References Cited

OTHER PUBLICATIONS

Sep. 22, 2015]. <URL: http://www.who.int/occupational_health/publications/airdust/en/> published on Oct. 29, 2004 as per Wayback Machine.

Owens et al., Blood glucose self-monitoring in type 1 and type 2 diabetes: reaching a multidisciplinary consensus. Diabetes and Primary Care, vol. 6, No. 1, pp. 8-16 (2004).

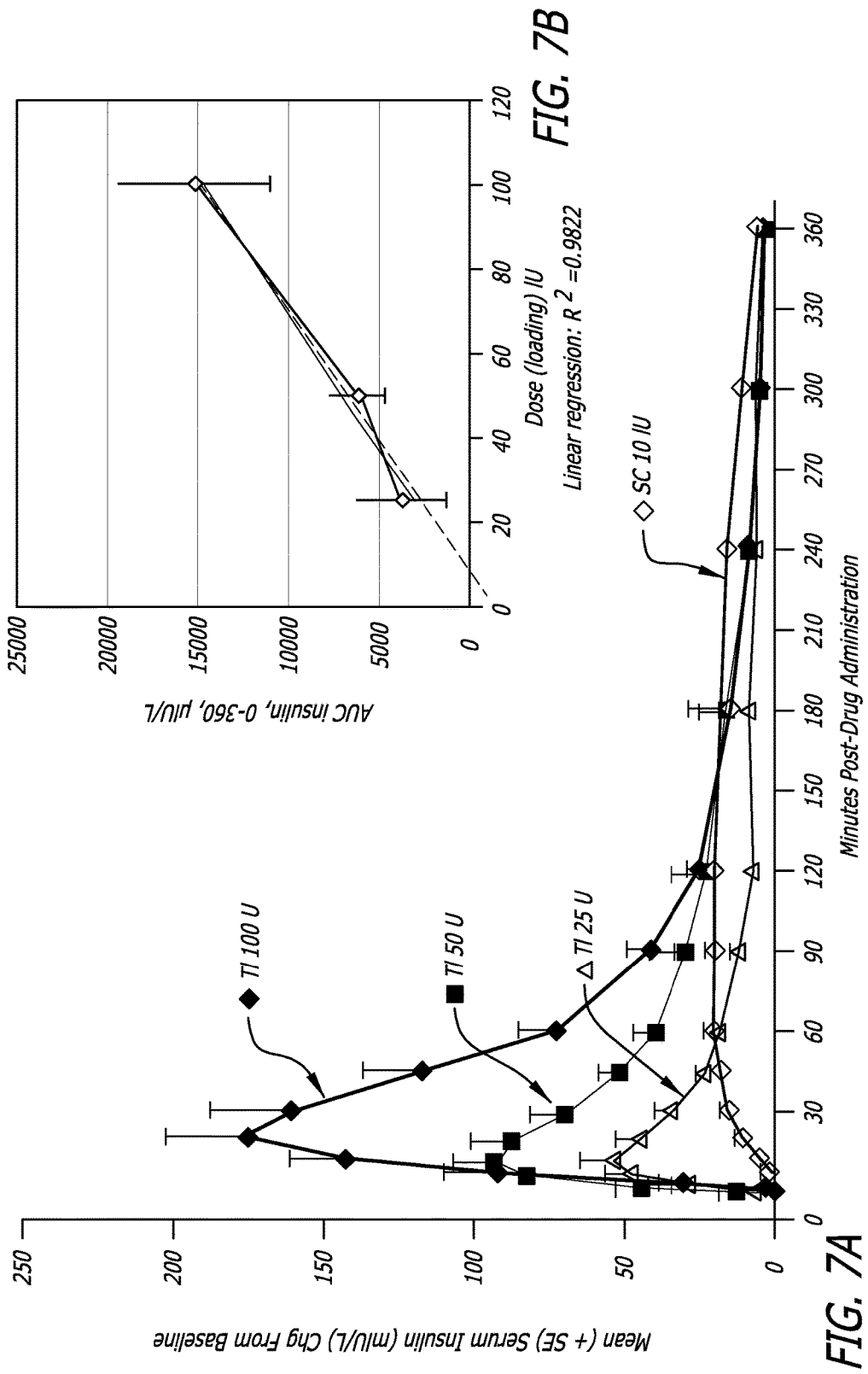

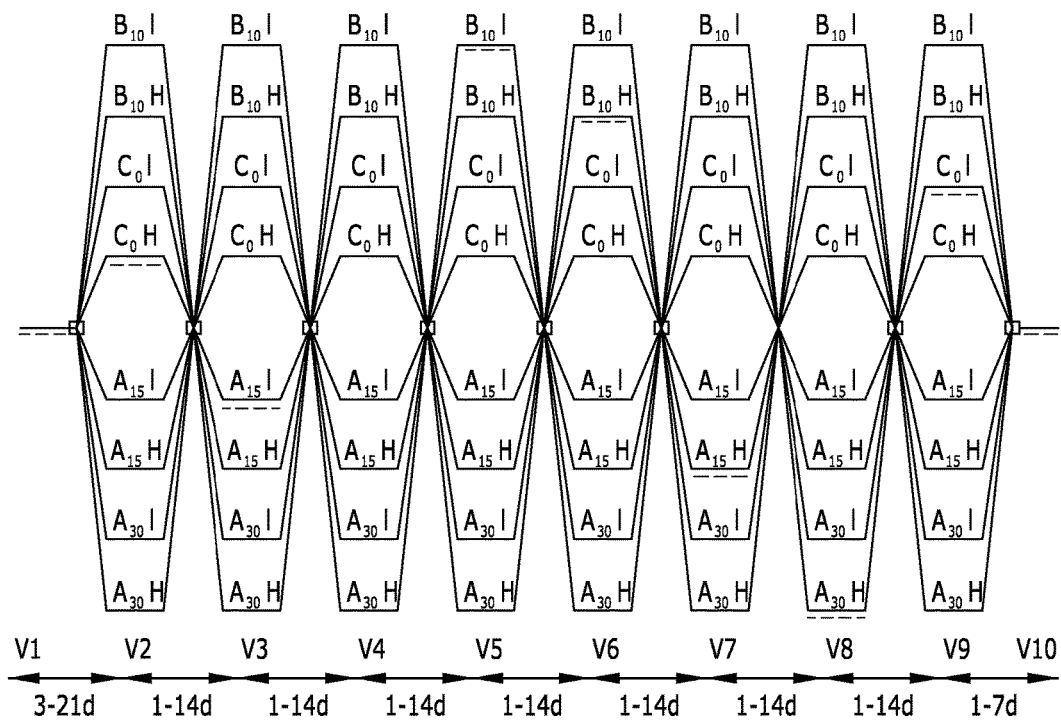

FIG. 20

------ *example for one patient*

$B_{10}$ I — Inhalation of Technosphere/Insulin 10 min BEFORE isocaloric meal $B_{10}$ H — Inhalation of Technosphere/Insulin 10 min BEFORE hypercaloric meal $C_0$ I — Inhalation of Technosphere/Insulin DIRECTLY PRIOR TO isocaloric meal $C_0$ H — Inhalation of Technosphere/Insulin DIRECTLY PRIOR TO hypercaloric meal $A_{15}$ I — Inhalation of Technosphere/Insulin 15 min AFTER isocaloric meal $A_{15}$ H — Inhalation of Technosphere/Insulin 15 min AFTER hypercaloric meal $A_{30}$ I — Inhalation of Technosphere/Insulin 30 min AFTER isocaloric meal $A_{30}$ H — Inhalation of Technosphere/Insulin 30 min AFTER hypercaloric meal

POTENTIATION OF GLUCOSE ELIMINATION

CROSS REFERENCE TO RELATED APPLICATIONS

This application is a continuation of U.S. patent application Ser. No. 11/329,686 filed Jan. 10, 2006, which claims priority under 35 U.S.C. §119(e) to U.S. Provisional Patent Application No. 60/643,070 filed Jan. 10, 2005 and U.S. Provisional Patent Application No. 60/667,393, filed Mar. 31, 2005 and is a continuation-in-part of U.S. patent application Ser. No. 10/719,734 filed Nov. 21, 2003 which is a continuation of U.S. patent application Ser. No. 10/224,761 filed Aug. 20, 2002, now U.S. Pat. No. 6,652,885, which is a division of U.S. patent application Ser. No. 09/606,468 filed Jun. 29, 2000, now U.S. Pat. No. 6,444,226 which claims priority under 35 U.S.C. §119(e) to U.S. Provisional Patent Application No. 60/141,433 filed Jun. 29, 1999, each of which are incorporated by reference herein in their entirety.

FIELD OF THE INVENTION

The present invention relates to methods of treating diabetes and improving the efficiency of insulin utilization. The method enables effective control of prandial glucose levels while reducing the risk of post-prandial hypoglycemia. In particular the method of the present invention potentiates the activity of endogenous insulin in type 2 diabetics and exogenous long-acting insulin in diabetics requiring basal insulin replacement.

BACKGROUND TO THE INVENTION

Diabetes mellitus currently afflicts at least 200 million people worldwide. Type 1 diabetes accounts for about 10% of this number, and results from autoimmune destruction of insulin-secreting β-cells in the pancreatic islets of Langerhans. Survival depends on multiple daily insulin injections. Type 2 diabetes accounts for the remaining 90% of individuals affected, and the rate of prevalence is increasing. Type 2 diabetes is often, but not always, associated with obesity, and although previously termed late-onset or adult diabetes, is now increasingly manifest in younger individuals. It is caused by a combination of insulin resistance and inadequate insulin secretion.

In a non-stressed normal individual, the basal glucose level will tend to remain the same from day to day because of an intrinsic feedback loop. Any tendency for the plasma glucose concentration to increase is counterbalanced by an increase in insulin secretion and a suppression of glucagon secretion, which regulate hepatic glucose production (gluconeogenesis and release from glycogen stores) and tissue glucose uptake to keep the plasma glucose concentration constant. If the individual gains weight or becomes insulin resistant for any other reason, blood glucose levels will increase, resulting in increased insulin secretion to compensate for the insulin resistance. Therefore the glucose and insulin levels are modulated to minimize changes in these concentrations while relatively normal production and utilization of glucose are maintained.

In this normal individual, a meal induces the secretion of a burst of insulin, generating a rapid spike in serum insulin concentration that then decays relatively quickly (see FIG. 1). This is referred to as first-phase kinetics and is responsible for the shut-off of release of glucose from the liver. Homeostatic mechanisms then match insulin secretion (and serum insulin levels) to the glucose load. This is observed as a slow decay of modestly elevated serum insulin levels back to baseline and is referred to as second-phase kinetics.

Type 2 diabetics typically exhibit a delayed response to increases in blood glucose levels. While normal individuals usually release insulin within 2-3 minutes following the consumption of food, type 2 diabetics may not secrete endogenous insulin until blood glucose begins to rise, and then with second-phase kinetics, that is a slow rise to an extended plateau in concentration. As a result, endogenous glucose production continues after consumption and the patient experiences hyperglycemia due to elevated blood glucose levels.

Loss of eating-induced insulin secretion is one of the earliest disturbances of β-cell function. While genetic factors play an important role, some insulin secretory disturbances seem to be acquired and may be at least partly reversible through optimal glucose control. Optimal glucose control via insulin therapy after a meal can lead to a significant improvement in natural glucose-induced insulin release by requiring both normal tissue responsiveness to administered insulin and an abrupt increase in serum insulin concentrations. Therefore, the challenge presented in treatment of early stage type 2 diabetics, those who do not have excessive loss of n-cell function, is to restore the rapid release of insulin following meals.

In addition to the loss of first-phase kinetics, early stage type 2 diabetics do not shut-off glucose release after a meal. As the disease progresses, the demands placed on the pancreas further degrades its ability to produce insulin and control of blood glucose levels gradually deteriorates. If unchecked, the disease can progress to the point that the deficit in insulin production approaches that typical of fully developed type 1 diabetes. Type 1 diabetes can involve an early "honeymoon" stage, following an initial crisis, in which insulin is still produced but defects in release similar to early type 2 disease are exhibited.

Most early stage type 2 diabetics currently are treated with oral agents, but with limited success. Subcutaneous injections are also rarely effective in providing insulin to type 2 diabetics and may actually worsen insulin action because of delayed, variable and shallow onset of action. It has been shown, however, that if insulin is administered intravenously with a meal, early stage type 2 diabetics experience the shutdown of hepatic glucose release and exhibit increased physiologic glucose control. In addition their free fatty acids levels fall at a faster rate that without insulin therapy. While possibly effective in treating type 2 diabetes, intravenous administration of insulin, is not a reasonable solution, as it is not safe or feasible for patients to intravenously administer insulin at every meal.

Significant pathology (and morbidity) in diabetics is associated with inadequate control of blood glucose. Excursions of blood glucose concentration both above and below the desired, normal range are problematic. In treatments that fail to mimic physiologic insulin release, the rise in insulin concentration does not produce sufficiently high glucose elimination rates to completely respond to the glucose load resulting from a meal. This can be further exacerbated by failure to shut off glucose release from the liver. Additionally, with many forms of insulin therapy, serum insulin levels and glucose elimination rates also remain elevated after the prandial glucose load has abated, threatening hypoglycemia. Attempts to better control peak glucose loads by increasing insulin dose further increase this danger.

Current insulin therapy modalities can supplement or replace endogenously-produced insulin to provide basal and second-phase-like profiles but do not mimic first-phase kinetics (see FIG. 2). Additionally, conventional insulin therapy often involves only one or two daily injections of insulin. However, more intensive therapy such as three or more administrations a day, providing better control of blood glucose levels, are clearly beneficial (see for example Nathan, D. M., et al., *N Engl J Med* 353:2643-53, 2005), but many patients are reluctant to accept the additional injections.

Until recently, subcutaneous (SC) injection has been the only route of delivering insulin to patients with both type 1 and type 2 diabetes. However, SC insulin administration does not lead to optimal pharmacodynamics for the administered insulin. Absorption into the blood (even with rapid acting insulin analogues) does not mimic the prandial physiologic insulin secretion pattern of a rapid spike in serum insulin concentration. Since the discovery of insulin, alternative routes of administration have been investigated for their feasibility in improving the pharmacodynamics of the administered insulin and improving compliance by reducing the discomfort associated with sc injections.

The alternative routes of insulin administration which have been evaluated in detail include the dermal, oral, buccal, nasal and pulmonary routes. Dermal insulin application does not result in reproducible and sufficient transfer of insulin across the highly efficient skin barrier. Oral insulin has not yet been achieved, primarily due to digestion of the protein and lack of a specific peptide carrier system in the gut. Nasal insulin application leads to a more rapid absorption of insulin across the nasal mucosa, however not with first-phase kinetics. The relative bioavailability of nasal administered insulin is low and there is a high rate of side effects and treatment failures. Buccally absorbed insulin also fails to mimic a first-phase release (Raz, I. et al., Fourth Annual Diabetes Meeting, Philadelphia, Pa., 2004).

Recently, pulmonary application of insulin has become a viable insulin delivery system. Some pulmonary insulin formulations in development provide faster appearance of insulin in the blood than typical subcutaneously delivered products (see FIG. 3), but apparently do not adequately reproduce all aspects of first-phase kinetics.

Therefore, a need exists for an insulin formulation which can mimic first-phase kinetics to provide physiologic post-prandial insulin pharmacokinetics and pharmacodynamics for maintenance of normal physiologic blood glucose levels.

SUMMARY OF THE INVENTION

The present invention provides methods of treating diabetes and improving the efficiency of insulin utilization. The method enables effective control of prandial glucose levels while reducing the risk of post-prandial hypoglycemia. In particular the method of the present invention improves the potentiation of exogenous prandial insulin as well as potentiating the activity of endogenous insulin in type 2 diabetics and exogenous long-acting insulin in diabetics requiring basal insulin replacement.

In one embodiment of the present invention, a method of improving potentiation of the glucose elimination rate of the present invention is provided comprising producing a first-phase insulin-like spike in serum insulin levels with an exogenously-administered insulin composition, wherein the exogenously-administered insulin composition is not administered intravenously.

In another embodiment of the method of improving potentiation of the glucose elimination rate of the present invention, the exogenously administered insulin composition is administered in proximity to a meal. In yet another embodiment the exogenously administered insulin composition is administered from approximately 10 minutes prior to a meal to approximately 30 minutes after a meal.

In yet another embodiment of the method of improving potentiation of the glucose elimination rate of the present invention, the insulin-related disorder is diabetes mellitus, such as type 1 or type 2 diabetes mellitus.

In an embodiment of the method of improving potentiation of the glucose elimination rate of the present invention, the first-phase-like spike in serum insulin concentration is greater than about 75 mU/L, greater than about 100 mU/L or greater than about 125 mU/L In another embodiment of the method of improving potentiation of the glucose elimination rate of the present invention, the first-phase-like spike in serum insulin concentration is achieved within about 20 minutes, within about 15 minutes or within about 10 minutes.

In another embodiment of the method of improving potentiation of the glucose elimination rate of the present invention, the potentiation comprises the glucose elimination rate reaching maximum within about 1 hour. In yet another embodiment the potentiation comprises the glucose elimination rate reaching maximum within about 45 minutes.

In an embodiment of the method of improving potentiation of the glucose elimination rate of the present invention, the glucose elimination rate continues to rise after serum insulin concentration begins to fall.

In another embodiment of the method of improving potentiation of the glucose elimination rate of the present invention, the glucose elimination rate begins to fall by about 1 hour after insulin administration.

In yet another embodiment of the method of improving potentiation of the glucose elimination rate of the present invention, the glucose elimination rate returns to baseline by about 6 hours.

In another embodiment of the method of improving potentiation of the glucose elimination rate of the present invention, the exogenously-administered insulin composition comprises a complex between a diketopiperazine and human insulin. In yet another embodiment the diketopiperazine is fumaryl diketopiperazine.

In an embodiment of the method of improving potentiation of the glucose elimination rate of the present invention, the exogenously-administered insulin composition is inhaled.

In an embodiment of the present invention, a method of mimicking first-phase human beta cell insulin release is provided comprising administering an exogenously-administered insulin composition.

In another embodiment of the method of mimicking first-phase human beta cell insulin release of the present invention, the exogenously-administered insulin composition comprises a complex between a diketopiperazine and human insulin. In another embodiment, the diketopiperazine is fumaryl diketopiperazine. In yet another embodiment, the exogenously-administered insulin composition is inhaled.

In one embodiment of the present invention, a method of treating an insulin-related disorder is provided comprising administering to a patient having an insulin-related disorder an exogenously-administered composition such that the exogenously-administered insulin composition mimics first-phase insulin kinetics, and wherein the exogenously-administered insulin composition is not administered intravenously.

In another embodiment of the method of treating an insulin-related disorder of the present invention, the exogenously-administered insulin composition comprises a complex between a diketopiperazine and human insulin. In another embodiment, the diketopiperazine is fumaryl diketopiperazine. In yet another embodiment, the exogenously-administered insulin composition is inhaled.

In yet another embodiment of the method of treating an insulin-related disorder of the present invention, the insulin-related disorder is diabetes mellitus, such as type 1 or type 2 diabetes mellitus.

In one embodiment of the present invention, a method of maintaining blood glucose levels in a patient with an insulin-related disorder in a normal range is provided comprising providing an exogenously-administered insulin composition wherein first-phase insulin pharmacokinetics are obtained within about 30 minutes of administration, alternatively within about 15 minutes of administration and wherein the exogenously-administered insulin composition is not administered intravenously.

In another embodiment of the method of maintaining blood glucose levels of the present invention, the exogenously-administered insulin composition comprises a complex between a diketopiperazine and human insulin. In another embodiment, the diketopiperazine is fumaryl diketopiperazine.

In another embodiment of the method of maintaining blood glucose levels of the present invention, the exogenously administered insulin composition is a non-naturally occurring form of insulin.

In one embodiment of the present invention, a method of restoring normal insulin kinetics in a patient in need thereof is provided comprising administering to a patient having an insulin-related disorder an inhaled insulin composition such that the inhaled insulin composition mimics first-phase insulin kinetics. In another embodiment, the insulin-related disorder is diabetes mellitus. In yet another embodiment, the method further comprises administering a long-acting basal insulin.

BRIEF DESCRIPTION OF THE DRAWINGS

FIGS. 7A-B depict the mean serum insulin concentration (FIG. 7A) and insulin absorption, as AUC (FIG. 7B), in individuals with type 2 diabetes mellitus at different dose levels of Technosphere®/Insulin (TI) and SC insulin according to the teachings of the present invention.

and forced vital capacity (FVC, FIG. 19B) over time in a three month placebo-controlled clinical study with Technosphere®/Insulin according to the teachings of the present invention.

FIG. 20 depicts the study schema for the clinical trial disclosed in Example 6.

Figure 21A:
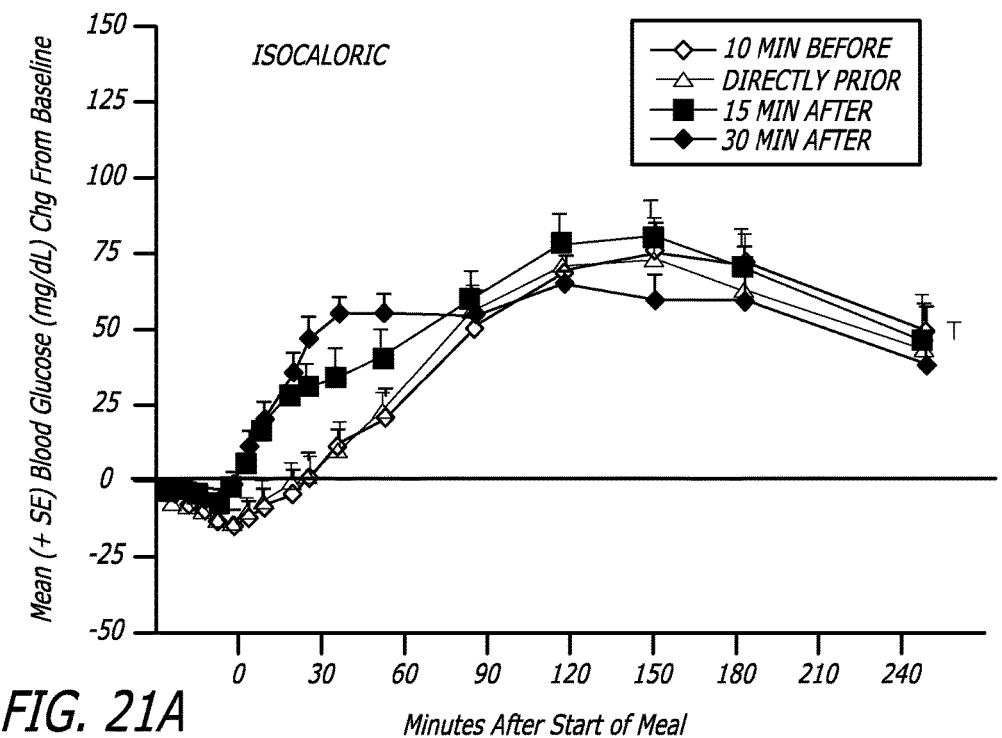
Figure 21B:
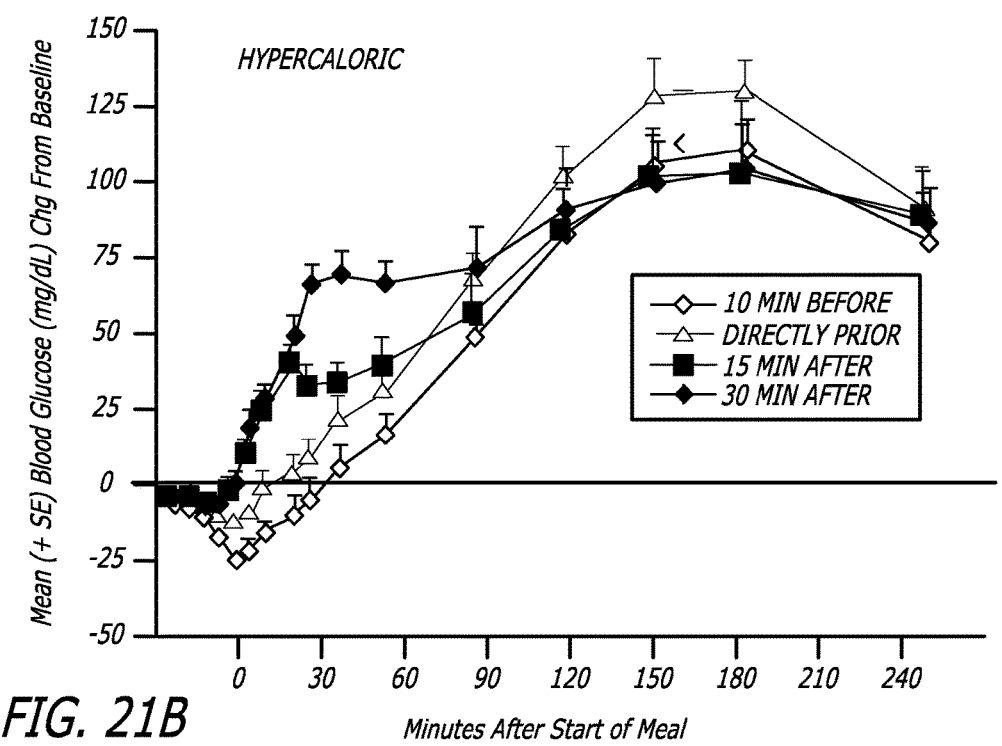

FIGS. 21A-B depict the baseline-corrected blood glucose concentration versus time by treatment group after administration of Technosphere®/Insulin and a isocaloric meal (FIG. 21A) or a hypercaloric meal (FIG. 21B) according to the teachings of the present invention.

Figure 22A:
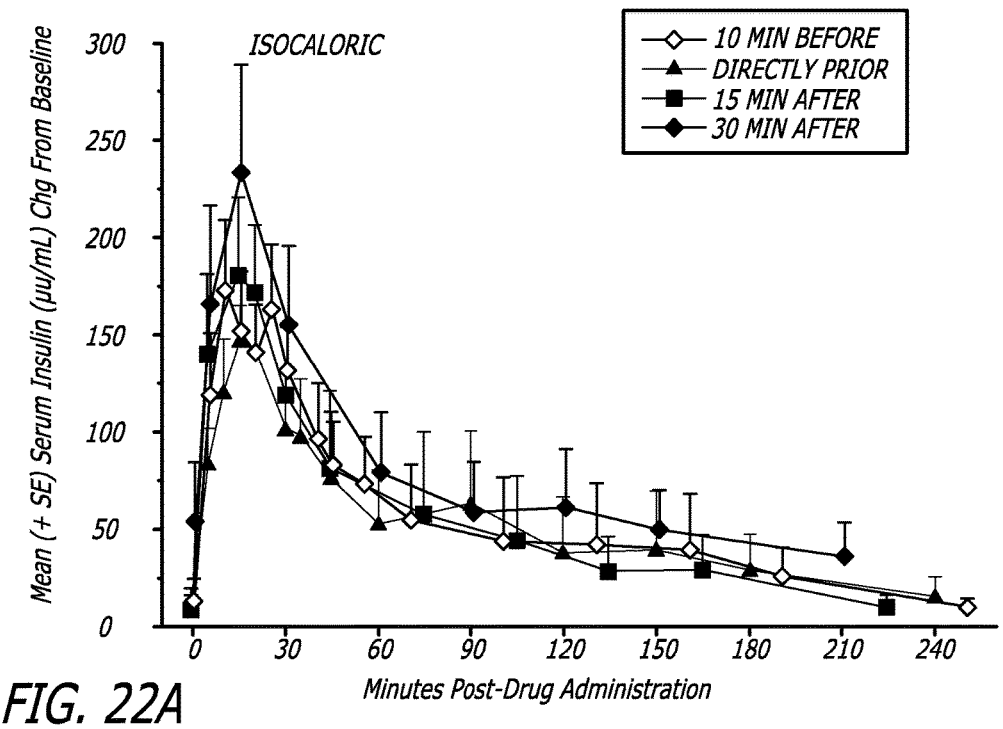
Figure 22B:
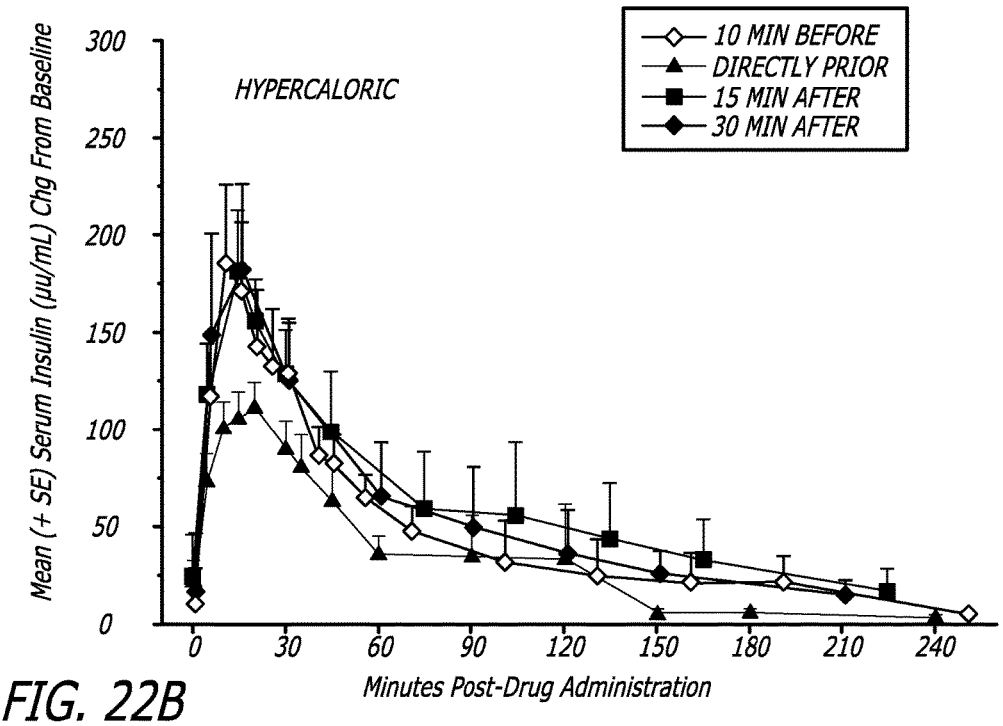

FIGS. 22A-B depict the baseline-corrected serum insulin concentration versus time by treatment group after administration of Technosphere®/Insulin and a isocaloric meal (FIG. 22A) or a hypercaloric meal (FIG. 22B) according to the teachings of the present invention.

Figure 23A:
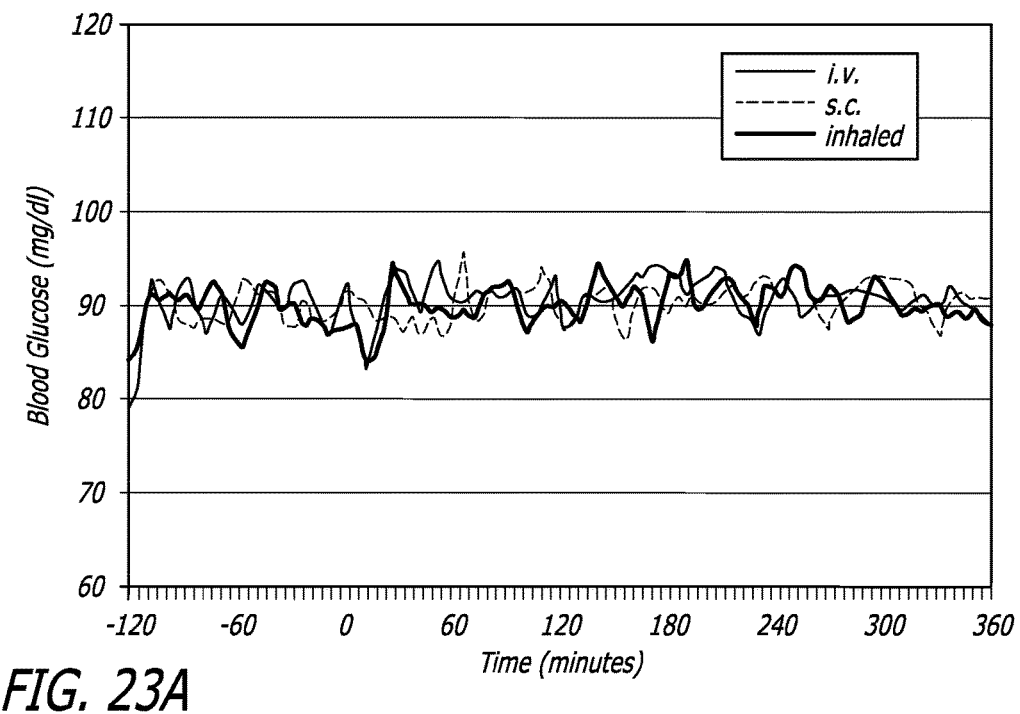
Figure 23B:
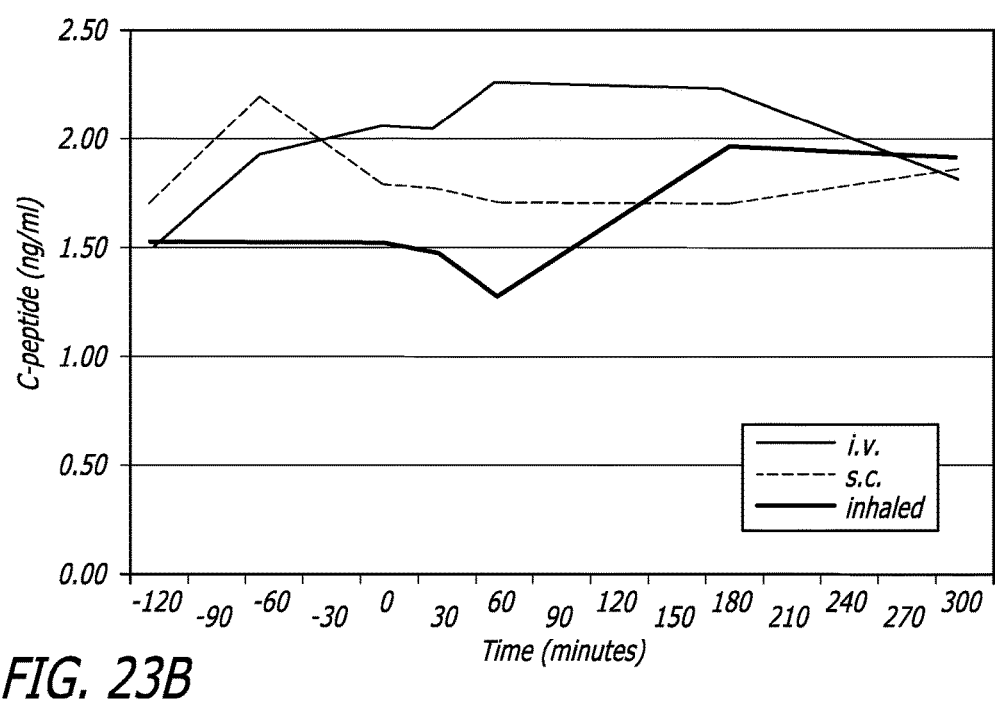

FIGS. 23A-B depict the mean blood glucose levels (FIG. 23A) or C-peptide levels (FIG. 23B) over time after administration of IV, SC or TI (inhaled) insulin according to the teachings of the present invention.

Figure 24A:
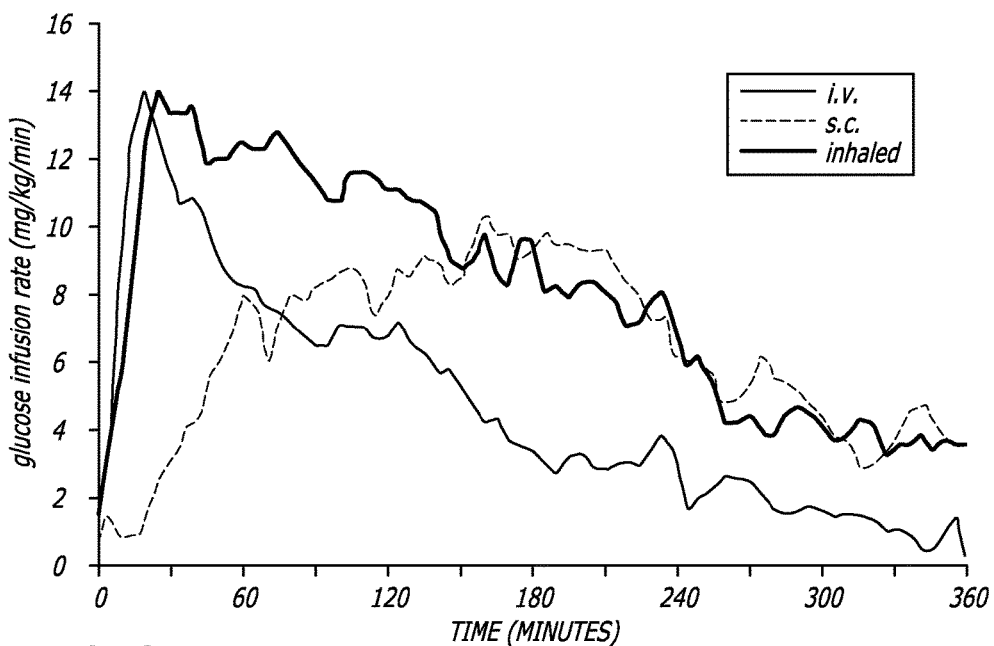
Figure 24B:
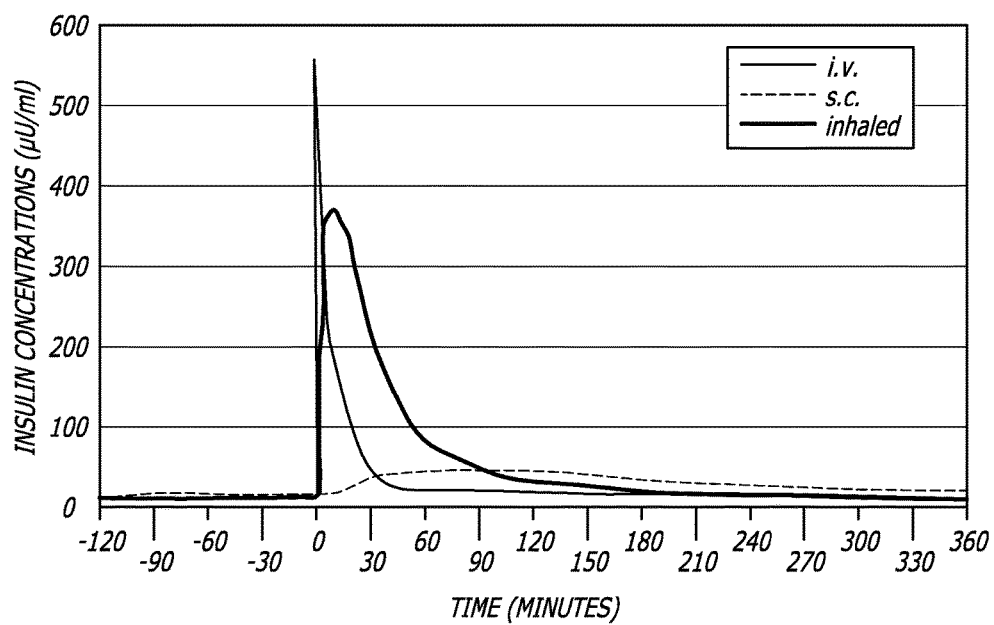

FIGS. 24A-B depict glucose infusion rate (FIG. 24A) or mean insulin concentration (FIG. 24B) over time after administration of IV, SC or TI (inhaled) insulin according to the teachings of the present invention.

DEFINITION OF TERMS

Prior to setting forth the invention, it may be helpful to provide an understanding of certain terms that will be used hereinafter:

Dry powder: As used herein "dry powder" refers to a fine particulate composition that is not suspended or dissolved in a propellant, carrier, or other liquid. It is not meant to imply a complete absence of all water molecules.

Excursion: As used herein, "excursion" refers to blood glucose concentrations that fall either above or below a pre-meal baseline or other starting point. Excursions are generally expressed as the area under the curve (AUC) of a plot of blood glucose over time. AUC can be expressed in a variety of ways. In some instances there will be both a fall below and rise above baseline creating a positive and negative area. Some calculations will subtract the negative AUC from the positive, while others will add their absolute values. The positive and negative AUCs can also be considered separately. More sophisticated statistical evaluations can also be used. In some instances it can also refer to blood glucose concentrations that rise or fall outside a normal range. A normal blood glucose concentration is usually between 70 and 110 mg/dL from a fasting individual, less than 120 mg/dL two hours after eating a meal, and less than 180 mg/dL after eating.

First-Phase: As used herein, "first-phase" refers to a burst of insulin release from the pancreas induced as a result of a meal. A first-phase insulin release generates a spike in blood insulin concentration that is a rapid peak which then decays relatively quickly.

Glucose Elimination Rate: As used herein, "glucose elimination rate" is the rate at which glucose disappears from the blood and is determine by the amount of glucose infusion required to maintain stable blood glucose, often around 120 mg/dL during the study period. This glucose elimination rate is equal to the glucose infusion rate, abbreviated as GIR.

Hyperglycemia: As used herein, "hyperglycemia" is a higher than normal fasting blood glucose concentration, usually 126 mg/dL or higher. In some studies hyperglycemic episodes were defined as blood glucose concentrations exceeding 280 mg/dL (15.6 mM).

Hypoglycemia: As used herein, "hypoglycemia" is a lower than normal blood glucose concentration, usually less than 60 mg/dL, but in some instances less than 3.5 mM (63 mg/dL).

Insulin Composition: As used herein, "insulin composition" refers to any form of insulin suitably for administration to a mammal and includes insulin isolated from mammals, recombinant insulin, insulin associated with other molecules and also includes insulin administered by any route including, pulmonary, subcutaneous, nasal, oral, buccal and sublingual. Insulin compositions can be formulated as dry powders or aqueous solutions for inhalation; aqueous solutions for subcutaneous, sublingual, buccal, nasal or oral administration and solid dosage forms for oral and sublingual administration.

Insulin-Related Disorder: As used herein, "insulin-related disorders" refers to disorders involving production, regulation, metabolism, and action of insulin in a mammal. Insulin related disorders include, but are not limited to, type 1 diabetes mellitus, type 2 diabetes mellitus, hypoglycemia, hyperglycemia, insulin resistance, loss of pancreatic beta cell function and loss of pancreatic beta cells.

Periprandial: As used herein, "periprandial" refers to a period of time starting shortly before and ending shortly after the ingestion of a meal or snack.

Postprandial: As used herein, "postprandial" refers to a period of time after ingestion of a meal or snack.

Potentiation: Generally, potentiation refers to a condition or action that increases the effectiveness or activity of some agent over the level that the agent would otherwise attain. Similarly it may refer directly to the increased effect or activity. As used herein, "potentiation" particularly refers to the ability of elevated blood insulin concentrations to boost effectiveness of subsequent insulin levels to, for example, raise the glucose elimination rate.

Prandial: As used herein, "prandial" refers to a meal or a snack.

Second-Phase: As used herein, "second-phase" refers to the slow decay of modestly elevated blood insulin levels back to baseline after the first-phase has passed. Second-phase can also refer to the non-spiking release of insulin in response to elevated blood glucose levels.

Technosphere®/Insulin: As used herein, "Technosphere®/Insulin" refers to an insulin composition comprising regular human insulin and Technosphere® microparticles, a drug delivery system. Technosphere® microparticles comprise a diketopiperazine. Specifically, Technosphere®/Insulin comprises a fumaryl diketopiperazine/human insulin composition.

Technosphere®/Placebo: As used herein, "Technosphere®/Placebo" refers to Technosphere® particles which are not associated with insulin.

Units of measure: Subcutaneous and intravenous insulin dosages are expressed in IU which is defined by a standardized biologic measurement. Amounts of insulin formulated with fumaryl diketopiperazine (FDKP) are also reported in IU as are measurements of insulin in the blood. Technosphere®/Insulin dosages are expressed in arbitrary units (U) which are numerically equivalent to the amount of insulin formulated in the dosage.

DETAILED DESCRIPTION OF THE INVENTION

A common problem in the use of insulin therapy in the treatment of diabetes is that doses sufficient to control prandial glucose loads produce elevated glucose elimination rates for extended intervals that can persist after the meal, leading to post prandial hypoglycemia. It is now disclosed that a short sharp rise to peak serum insulin concentration (which then declines) results in an accelerated approach to maximal glucose elimination rates. This has the effect of compressing the bulk of the effect of the administered insulin to the periprandial time interval reducing the risks of post-prandial hypoglycemia. The field has generally assumed that the rate of glucose elimination at any point in time is a function of insulin concentration at that point in time. In point of fact the glucose elimination rate achieved by any particular insulin concentration is influenced by prior insulin concentration. Thus glucose elimination rate is potentiated by previous high insulin levels such that, for any particular insulin concentration, the glucose elimination rate is greater when the subject has experienced a high insulin concentration in a preceding time interval. The present inventors have now surprisingly discovered that this potentiation drives the glucose elimination rate to maximum much more quickly in response to a large and rapid peak in insulin concentration than when peak insulin concentration is approached more gradually.

Figure 1:
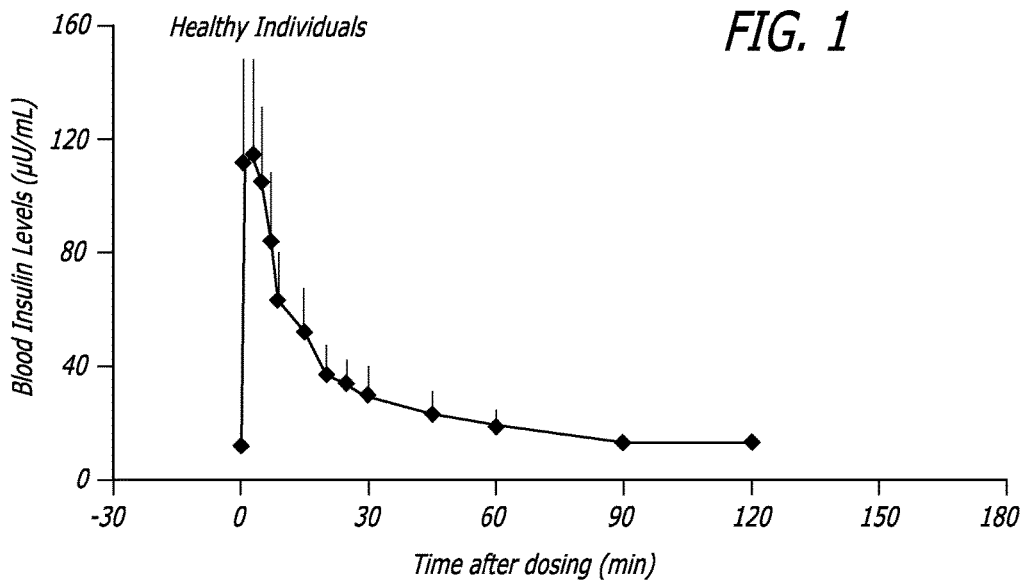
FIG. 1 depicts the measurement of first-phase insulin release kinetics following artificial stimulation by bolus glucose infusion.
Figure 2:
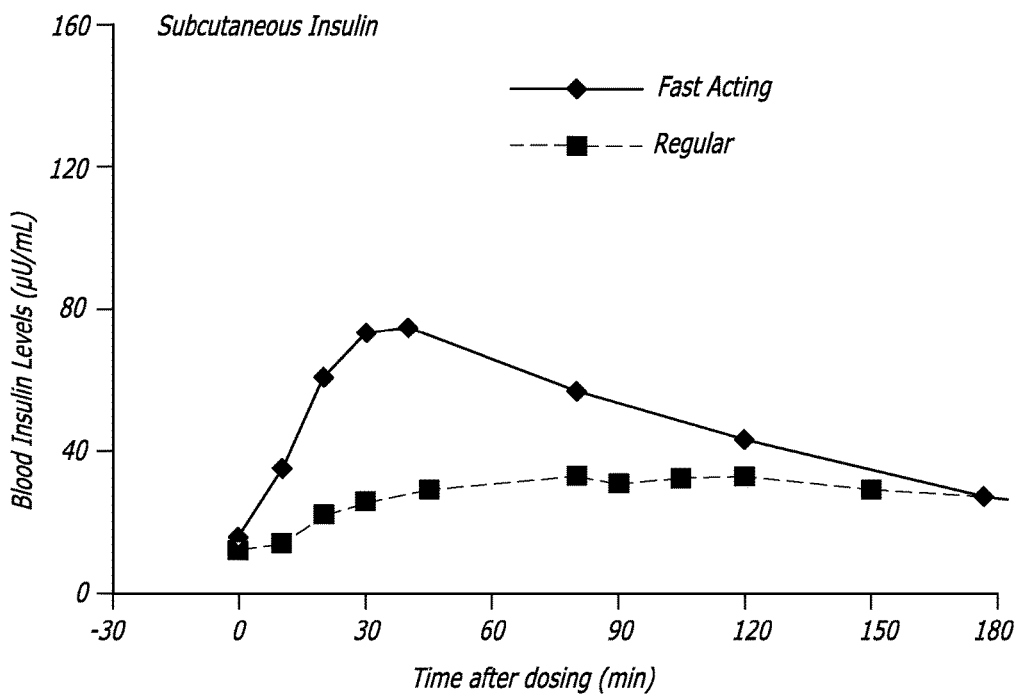
FIG. 2 depicts serum insulin concentration after administration of subcutaneous (SC) regular human insulin or sc fast acting insulin (Novolog™) Novolog™ is a registered trademark of Novo Nordisk Pharmaceuticals, Bagsvaerd, Denmark.
Figure 3:
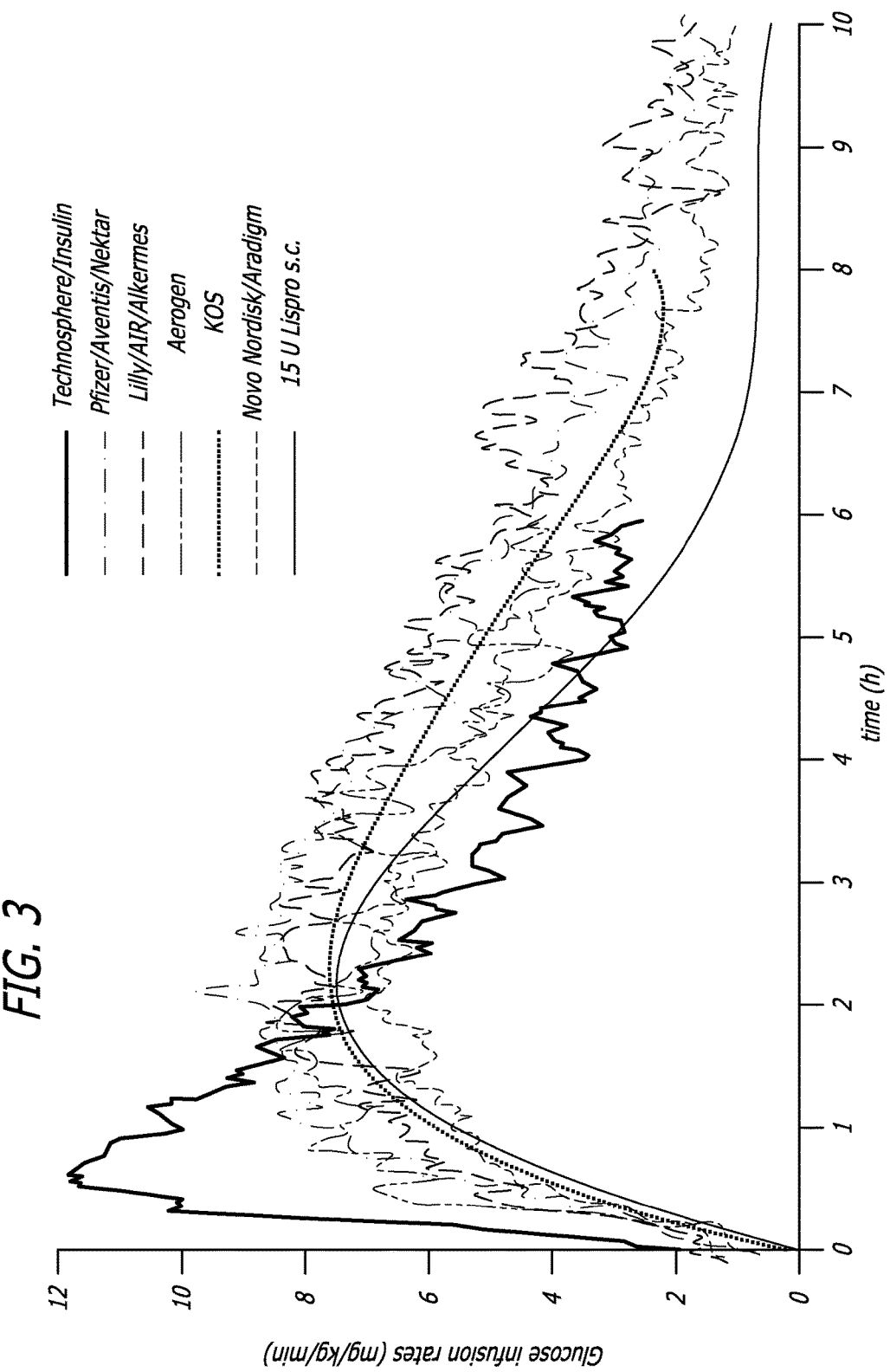
FIG. 3 depicts a composite of time-action profiles of a variety of forms of inhaled (MannKind, Pfizer/Aventis/Nektar, Alkermes, Aerogen, KOS, Novo Nordisk/Aradigm) and injected (Lispro sc) insulin from different manufacturers (from: Br J Diab Vasc. Dis 4:295-301, 2004).
Figure 4:
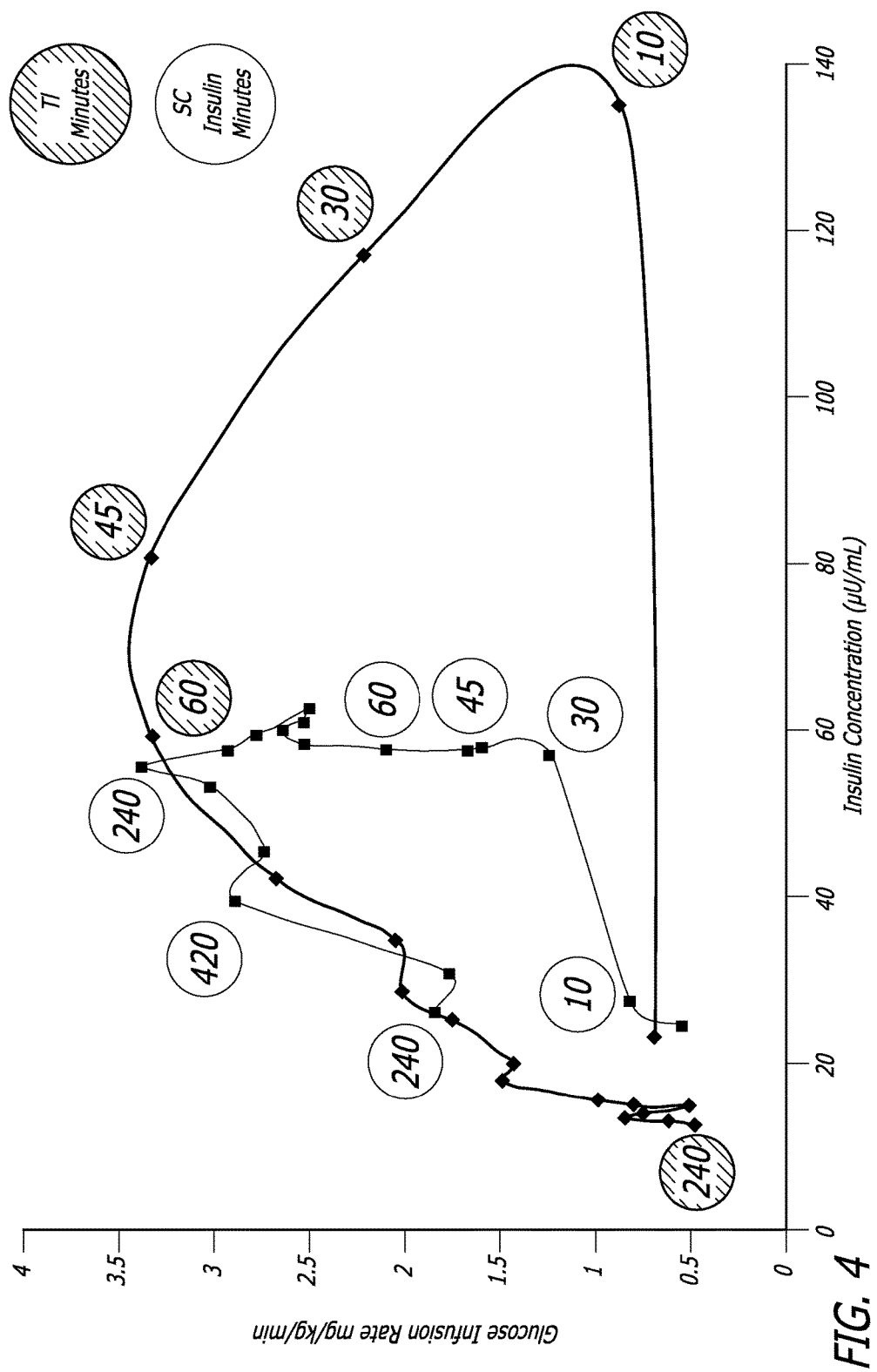
FIG. 4 depicts the relationship over time between serum insulin concentration and glucose elimination rate, as glucose infusion rate (GIR) under a glucose clamp, for a fast-acting subcutaneously administered insulin (SC) and a pulmonary dry powder insulin formulated with fumaryl diketopiperazine (Technosphere®/Insulin, TI) according to the teachings of the present invention.
Figure 5:
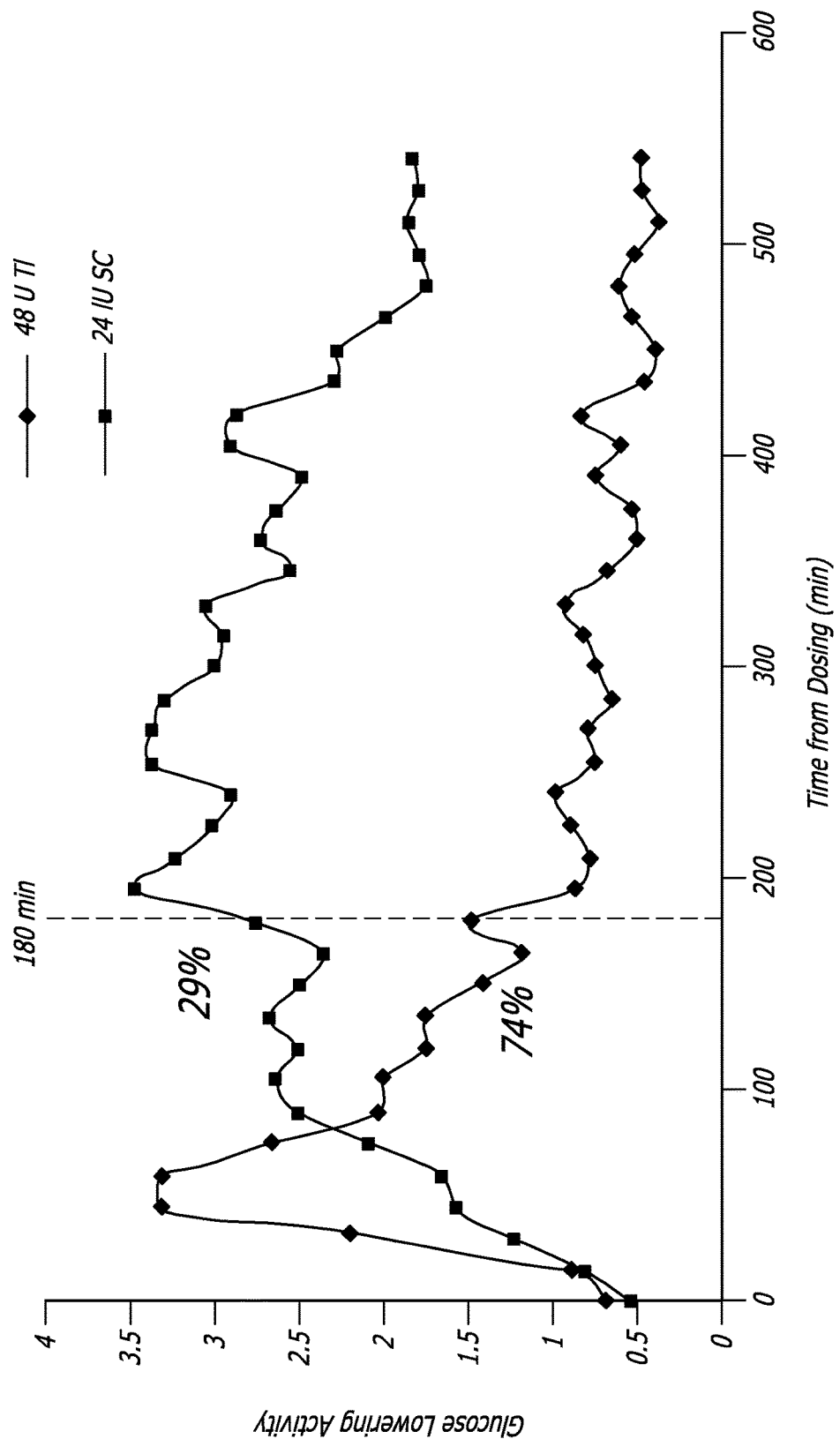
FIG. 5 depicts increased postprandial glucose elimination for Technosphere®/Insulin (48 U TI) versus a fast-acting subcutaneously administered insulin (24 IU SC) in individuals with type 2 diabetes mellitus according to the teachings of the present invention.

With a typical fast-acting subcutaneously (SC) administered insulin, maximal insulin concentrations can be achieved in about 30 to 45 minutes and remain at this plateau for several hours (FIG. 2). The glucose elimination rate (measured as the glucose infusion rate [GIR]) however continues to rise throughout this plateau phase (FIG. 5), peaking only as insulin concentration begins to decay (FIG. 4). In contrast, with an administration that mimics a physiological first-phase insulin release, insulin concentration peaks at a much higher level and begins to fall by about 15 minutes (FIG. 1). The GIR, however, continues to rise after the peak in insulin concentration but reaches its maximum in less than an hour and then falls in concert with insulin concentration (FIG. 4). By three hours, the bulk of glucose elimination to be accomplished by this insulin has occurred, yet the subcutaneous insulin has exerted less than a third of its effect (FIG. 5).

By taking advantage of the potentiating effects of a rapid spike in insulin concentration, an insulin therapy methodology that mimics first-phase kinetics can offer several advantages. Such insulin formulations are generally administered within a few minutes of commencing a meal, unlike more slowly absorbed insulins which are usually taken at defined period before a meal. The interval is generally based on the time needed to achieve maximal insulin concentration on the tacit assumption that glucose elimination rate is a function of insulin concentration. However, since glucose elimination rate continues to increase throughout the plateau in insulin concentration, doses large enough to keep glucose levels from exceeding the normal range pose a risk that the resultant high glucose elimination rate hours after the meal will lead to hypoglycemia. Due to the potentiating effect of an insulin preparation causing a rapid peak in serum insulin concentration, it can be more readily coordinated with a meal. The quick acquisition of maximal glucose elimination rate is well suited to mealtime administration, or even up to an hour after commencing a meal. The second-phase decay in insulin concentration reduces the risk of inducing hypoglycemia hours after the meal. Further advantages are realized in diabetics who retain some ability to produce insulin in that their endogenous second-phase and basal insulin will also be potentiated, increasing the effectiveness of that limited insulin and reducing pancreatic stress. Methods of reducing pancreatic stress with the exogenously-administered insulin compositions of the present invention are disclosed in U.S. Provisional Patent Application No. 60/704, 295 entitled "Methods of Preserving the Function of Insulin-Producing Cells in Diabetes," which is incorporated by reference herein for all it teaches regarding methods of reducing pancreatic stress by administering diketopiperazine/insulin compositions. The administration of exogenous insulin also suppresses insulin secretion from the pancreas. The quicker return to baseline achieved with a rapidly peaking insulin allows for earlier reassertion of pancreatic secretion and re-establishment of homeostatic control of blood glucose levels, further reducing the risk of post-treatment hypoglycemia. Similar advantages are contemplated from combined treatment with rapid-peaking and long acting exogenous insulin for diabetics who do not produce significant levels of insulin.

As used herein, mimicking physiologic mealtime first-phase insulin release (or pharmacokinetics) does not necessarily indicate exact replication of all features of the physiologic response. It can refer to methodologies producing a spike or peak of insulin concentration in the blood that constitutes both a relatively quick rise (less than about 15 minutes from administration or first departure from baseline) and fall (descent through half maximal by 80 minutes, preferably 50 minutes, more preferably 35 minutes after peak) in concentration. This is in contrast to methods producing a more gradual rise (from over 20 minutes to several hours) to the maximal insulin concentration achieved and a prolonged plateau at near maximal concentrations. It can also refer to methodologies in which the spike in insulin concentration can be reliably coordinated with the start of a meal. It can also refer to methodologies achieving maximal glucose elimination rate within about 30-90 minutes, preferably around 45-60 minutes, after administration. A methodology that mimics first-phase release is generally also one that can be practiced by diabetics upon themselves without special medical training, such as training in intravenous injection. Special medical training would not include training to use medical devices, such as dry powder inhalers, that are routinely used by persons who are not medical professionals. As used herein, "meal", "meals", and/or "mealtime", etc. include traditional meals and meal times; however, these also include the ingestion of any sustenance regardless of size and/or timing.

Superior blood glucose control can be appreciated as reduced exposure to (elevated) glucose concentrations ($AUC_{GLU}$), reduced levels of HbA1c (glycosylated hemoglobin), lessened potential or incidence of hypoglycemia, reduced variability of response to treatment, and the like. Glycosylated hemoglobin levels correlate with the overall blood glucose control over the past three months. Generally one compares outcomes of different procedures at similar levels of exposure to insulin ($AUC_{INS}$) for various time intervals. Glucose exposure and risk of hypoglycemia ultimately depends on how well glucose elimination rate matches glucose load over time. This in turn will generally depend on the shape of the insulin concentration curve rather than simply on the area under the curve. The rapid rise and fall of insulin concentration typical of physiologic first-phase response is well suited to matching glucose elimination rate to prandial glucose load.

The desirable first phase kinetics can be obtained through the pulmonary administration of a dry powder insulin formulation containing insulin complexed to 3,6-di(fumaryl-4-aminobutyl)-2,5-diketopiperazine (hereinafter fumaryl diketopiperazine or FDKP). The use of diketopiperazines for drug delivery is known in the art (see for example U.S. Pat.

No. 5,352,461 entitled "Self Assembling Diketopiperazine Drug Delivery System; U.S. Pat. No. 5,503,852 entitled Method for Making Self-Assembling Diketopiperazine Drug Delivery System; U.S. Pat. No. 6,071,497 entitled Microparticles for Lung Delivery Comprising Diketopiperazine; and U.S. Pat. No. 6,331,318 entitled Carbon-Substituted Diketopiperazine Delivery System, each of which is incorporated herein by reference for all that it teaches regarding diketopiperazines and diketopiperazine-mediated drug delivery). Pulmonary drug delivery using diketopiperazine and other microparticles is disclosed in U.S. Pat. No. 6,428,771 entitled "Method for Drug Delivery to the Pulmonary System," which is hereby incorporated by reference for all that it teaches regarding delivery of diketopiperazine-based compositions to the pulmonary system. Complexes of insulin and FDKP, their formation, properties, and use are disclosed in U.S. Pat. Nos. 6,444,226 and 6,652,885 both entitled "Purification and Stabilization of Peptide and Protein Pharmaceutical Agents," each of which is incorporated herein by reference for all that they teach regarding formation and administration of FDKP-complexed agents. Additional methods of manufacture of complexes of diketopiperazines and insulin are disclosed in U.S. Provisional Patent Application No. 60/717,524 entitled "Method of Drug Formulation Based on Increasing the Affinity of Active Agents for Crystalline Microparticle Surfaces," which is incorporated herein by reference for all it teaches regarding manufacture of complexes of diketopiperazines and insulin. Particularly advantageous devices for delivery of the powder are disclosed in U.S. patent application Ser. No. 10/655,153 entitled "Unit Dose Cartridge and Dry Powder Inhaler" and in U.S. Pat. No. 6,923,175 entitled "Inhalation Apparatus", each of which is incorporated herein by reference for all that they teach regarding pulmonary delivery of insulin compositions.

Complexation of large polymers, such as proteins and peptides in diketopiperazines can be used to remove impurities or contaminants such as metal ions or other small molecules. The diketopiperazines also serve both to stabilize and enhance delivery of the complexed materials. Formulations also have been developed facilitate transport of active agents across biological membranes. These formulations include microparticles formed of (i) the active agent, which may be charged or neutral, and (ii) a transport facilitator that masks the charge of the agent and/or that forms hydrogen bonds with the membrane. The formulations can provide rapid increases in the concentration of active agent in the blood following administration of the formulations.

Technosphere® refers to a diketopiperazine-based drug delivery system which can complex and stabilize peptides in small particles. Diketopiperazines, particularly fumaryl diketopiperazine (FDKP), self-assemble into microparticles with a mean diameter of about 2 microns. In the process it can entrap or complex with peptides, such as insulin, present in the solution during or after self-assembly. Once dried, these microparticles become a suitable composition for pulmonary delivery to the systemic circulation. When administered by the pulmonary route, Technosphere® particles dissolve in the pH neutral environment of the deep lung and facilitate the rapid and efficient absorption of the peptide into systemic circulation. The FDKP molecules are excreted un-metabolized in the urine within hours of administration.

Additionally, salts of diketopiperazines can be used in the compositions of the present invention as disclosed in co-pending U.S. patent application Ser. No. 11/210,710 entitled "Diketopiperazine Salts for Drug Delivery and Related Methods" which is incorporated by reference herein for all it teaches regarding diketopiperazine salts and their use to in pulmonary delivery of insulin.

Insulin, a polypeptide with a nominal molecular weight of 6,000 daltons, traditionally has been produced by processing pig and cow pancreas to isolate the natural product. More recently, however, recombinant technology has been used to produce human insulin in vitro. Natural and recombinant human insulin in aqueous solution is in a hexameric conformation, that is, six molecules of recombinant insulin are noncovalently associated in a hexameric complex when dissolved in water in the presence of zinc ions. Hexameric insulin is not rapidly absorbed. In order for recombinant human insulin to be absorbed into a patient's circulation, the hexameric form must first disassociate into dimeric and/or monomeric forms before the material can move into the bloodstream.

For example, it was discovered that hexameric insulin can be delivered to the lung in fumaryl diketopiperazine formulation, reaching peak blood concentrations within 3-10 minutes. In contrast, insulin administered by the pulmonary route without fumaryl diketopiperazine typically takes between 25-60 minutes to reach peak blood concentrations, while hexameric insulin takes 30-90 minutes to reach peak blood level when administered by subcutaneous injection. This feat has been successfully replicated several times and in several species, including humans.

Removing zinc from insulin typically produces unstable insulin with an undesirably short shelf life. Purification to remove zinc, stabilization and enhanced delivery of insulin is demonstrated by the examples. Formulations of insulin complexed with fumaryl diketopiperazine were found to be stable and have an acceptable shelf life. Measurement of the zinc levels demonstrated that the zinc had been largely removed during the complexation process, yielding monomeric insulin in a stable delivery formulation.

The insulin compositions of the present invention can be administered to patients in need of insulin therapy. The compositions preferably are administered in the form of microparticles, which can be in a dry powder form for pulmonary administration or suspended in an appropriate pharmaceutical carrier, such as saline.

The microparticles preferably are stored in dry or lyophilized form until immediately before administration. The microparticles then can be administered directly as a dry powder, such as by inhalation using, for example, dry powder inhalers known in the art. Alternatively, the microparticles can be suspended in a sufficient volume of pharmaceutical carrier, for example, as an aqueous solution for administration as an aerosol. The microparticles also can be administered via oral, subcutaneous, and intravenous routes.

The insulin compositions can be administered to any targeted biological membrane, preferably a mucosal membrane of a patient. In one embodiment, the patient is a human suffering from an insulin-related disorder such as diabetes mellitus. In another embodiment, the composition delivers insulin in biologically active form to the patient, which provides a spike of serum insulin concentration which simulates the normal response to eating.

EXAMPLES

Example 1

Insulin Concentration at Different Dose Levels Indicates Linear Absorption

Various dosages of Technosphere®/Insulin (TI, MannKind Corporation) were administered to human subjects and insulin concentration in the blood was measured (FIG. 7A). Insulin absorption, as AUC, was linear with dosage at least up to 100 U TI (FIG. 7B).

Example 2

Mimicry of the Early Phase Insulin Response in Humans with Rapidly Bioavailable Inhaled Insulin Accelerates Post Prandial Glucose Disposal Compared to Insulin with Slower Bioavailability The relationship between time, insulin concentration and glucose elimination rate in a group of 12 subjects with type 2 diabetes, during an isoglycemic insulin clamp was studied. Each subject received 24 IU subcutaneous insulin (Actrapid®, Novo Nordisk) or 48 U Technosphere®/Insulin on separate study days in a cross-over design.

Figure 8:
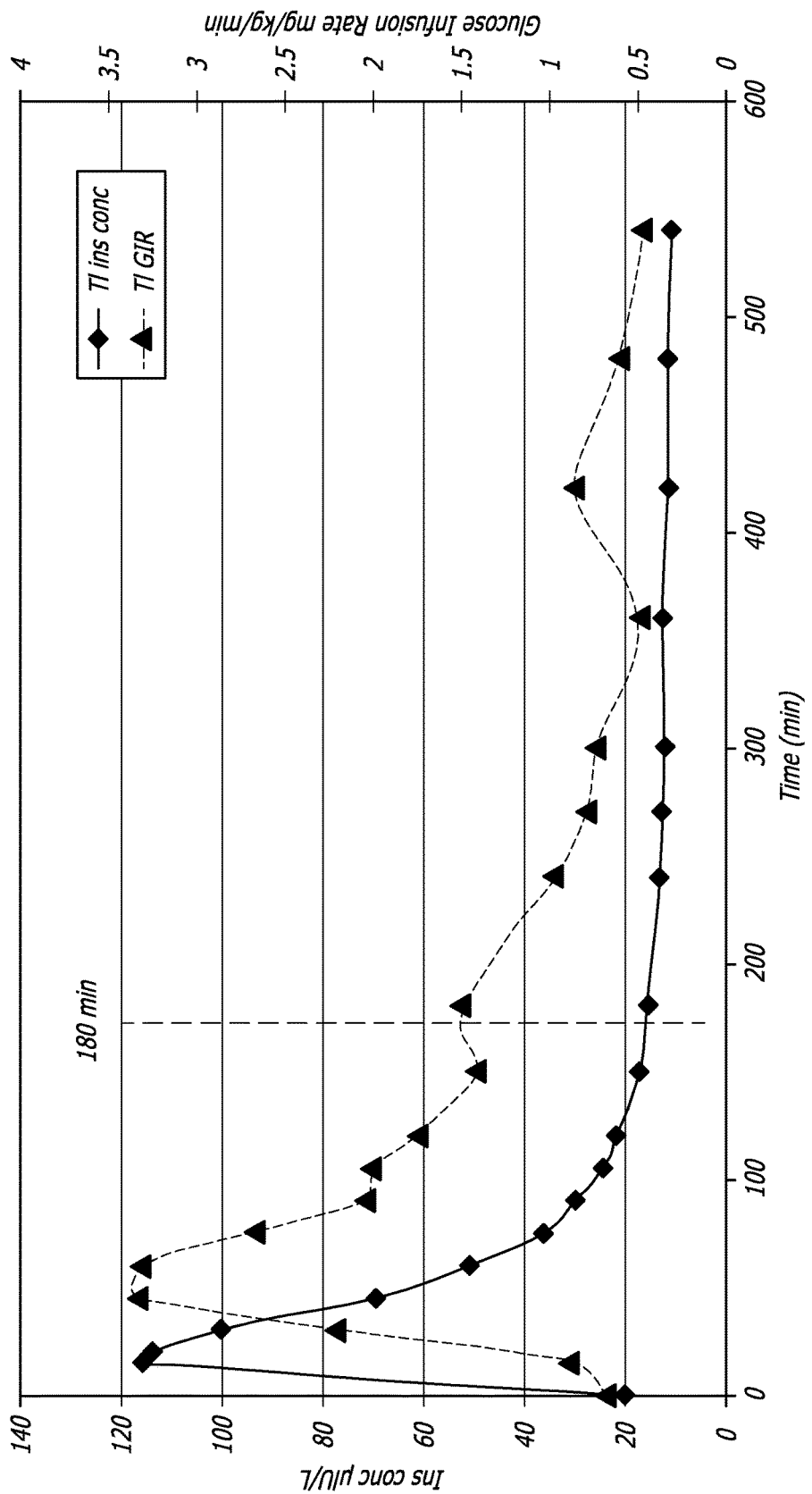
FIG. 8 depicts a comparison of insulin concentration and glucose elimination rate over time in individuals with type 2 diabetes mellitus after administration of 48 U of Technosphere®/Insulin (TI) according to the teachings of the present invention.

The glucose elimination rate (GIR) was determined by the amount of glucose infusion required to maintain stable blood glucose of 120 mg/dL during the 540 min study period (FIG. 4). Forty-eight units TI provided a mean maximum concentration of insulin ($C_{max}$) of 114.8±44.1 (mean±SD) mIU/L and had a median time to maximum concentration ($T_{max}$) of 15 min, whereas 24 IU subcutaneous insulin (SC) had a $C_{max}$ of 63±10.1 mIU/L with a $T_{max}$ of 150 min. Technosphere®/Insulin reached maximal GIR values, 3.33±1.35 mg/min/kg, at 45 min, while at that timepoint, SC was only 1.58±1.03 and did not reach maximal value, 3.38±1.45 before 255 min, despite almost constant insulin concentrations. The data for GIR and insulin concentration for TI are also plotted individually versus time in FIG. 8. Once maximal insulin effect was reached, the concentration-effect relationship was the same for TI and SC. At 180 min, glucose disposal was 326±119 mg/kg or 61% of total for TI and 330±153 mg/kg (27% of total) for SC.

A fast, sharp increase in insulin concentration, similar to the early phase insulin response, provided maximal glucose elimination rate. Forty-eight units TI achieved maximal effect within 45 min, whereas it took 270 min for 24 IU SC to reach similar effect. This phenomenon is not caused by differences in the dose-effect relationship for the two insulin types, but reflects a difference in response when the increment in insulin concentration is more modest over time as opposed to the more rapid bioavailable insulin provided by Technosphere®/Insulin. This can have consequences for postprandial glucose control.

Figure 14A:
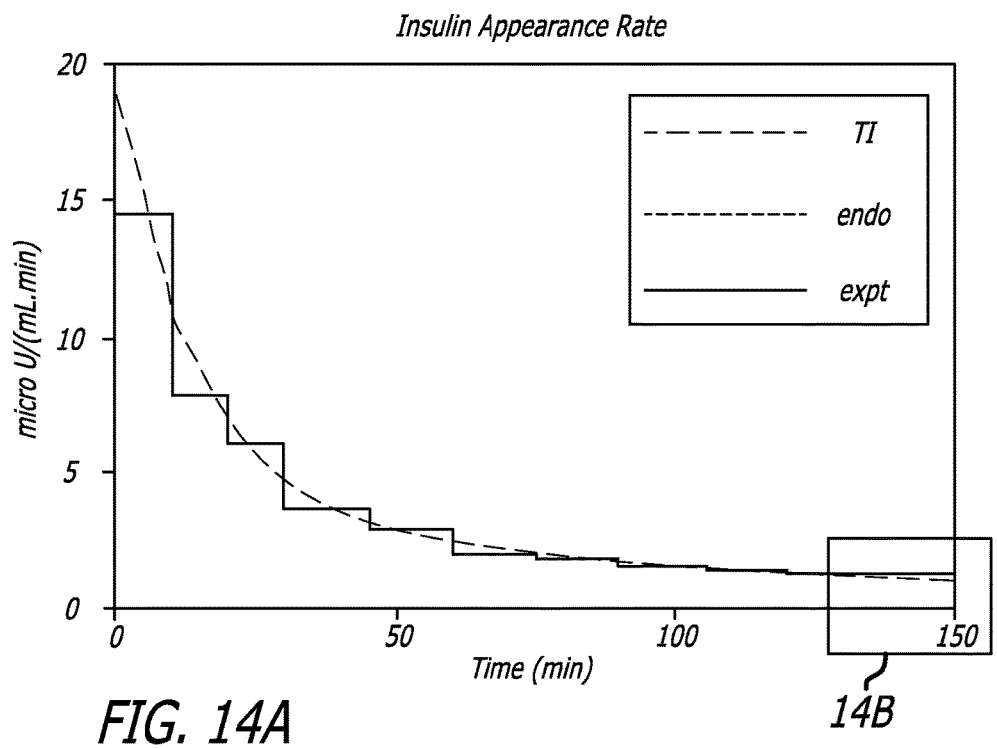
FIGS. 14A-B depict the insulin appearance rate over time for TI and endogenous insulin after administration of Technosphere®/Insulin (TI) in patients with type 2 diabetes according to the teachings of the present invention
Figure 14B:
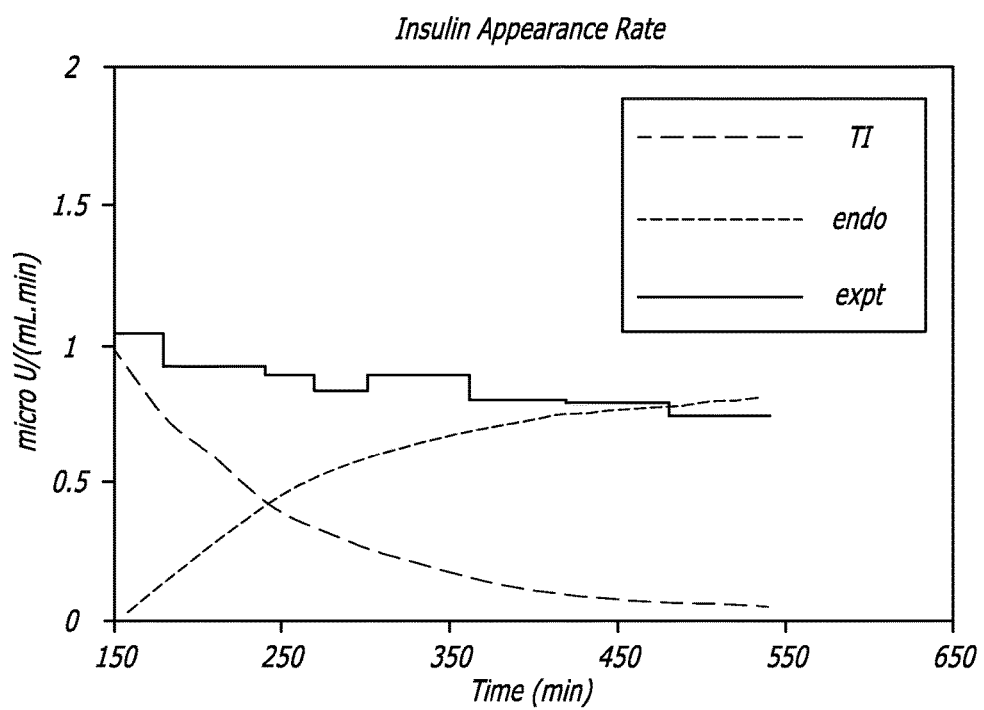

Additionally, three hours after dosing, 48 U TI and 24 IU SC had exerted the same glucose lowering effect. However, less than ⅓ of the total glucose lowering effect for the SC dose had been obtained. The glucose lowering activity 180 minutes after a meal was 74% for TI and 29% for SC insulin (FIG. 5). If the prandial insulin dose is titrated towards a goal of normoglycemia at three hours after a meal, the large remaining glucose lowering effect of SC insulin may increase the risk of late post prandial hypoglycemia, as compared to TI. In addition to confining the bulk of glucose lowering activity to a time period more similar to the glucose load created by a meal, the kinetics exhibited by TI also allowed for the reassertion of endogenous insulin secretion sooner, that is glycemic control is returned to homeostatic mechanisms. At late time points (>150 minutes), the fall in insulin concentration lags behind what would have been expected based on the decay rate seen at earlier time points. This can be understood as the superimposition of falling exogenous insulin (from TI) and rising endogenous insulin (FIG. 14). Endogenous insulin secretion should be accompanied by the production of C-peptide.

Figure 16:
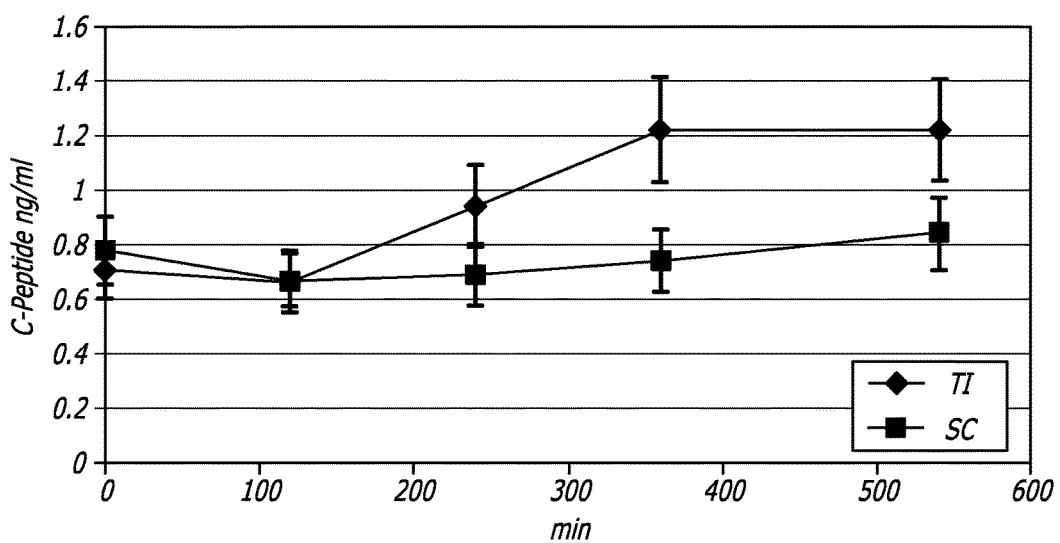
FIG. 16 depicts the levels of C-peptide after administration of Technosphere®/Insulin (TI) or SC insulin in individuals with type 2 diabetes mellitus according to the teachings of the present invention.

Mean serum C-peptide concentrations over time for inhaled Technosphere®/Insulin and injectable SC regular insulin are presented in FIG. 16. C-peptide concentrations were essentially unchanged during SC treatment but rose with TI treatment with a timing consistent with the model depicted in FIG. 14.

One of the most important aims of drug therapy in patients with type 2 diabetes is to restore or to replace the first phase of the meal-related insulin response which is lost early in the course of type 2 diabetes mellitus. The rapid onset and short duration of action of inhaled Technosphere®/Insulin should make it suitable for replacement of prandial insulin secretion in patients with diabetes mellitus.

Example 3

A Fast Insulin Spike does not Increase Risk of Hypoglycemia

Figure 15:
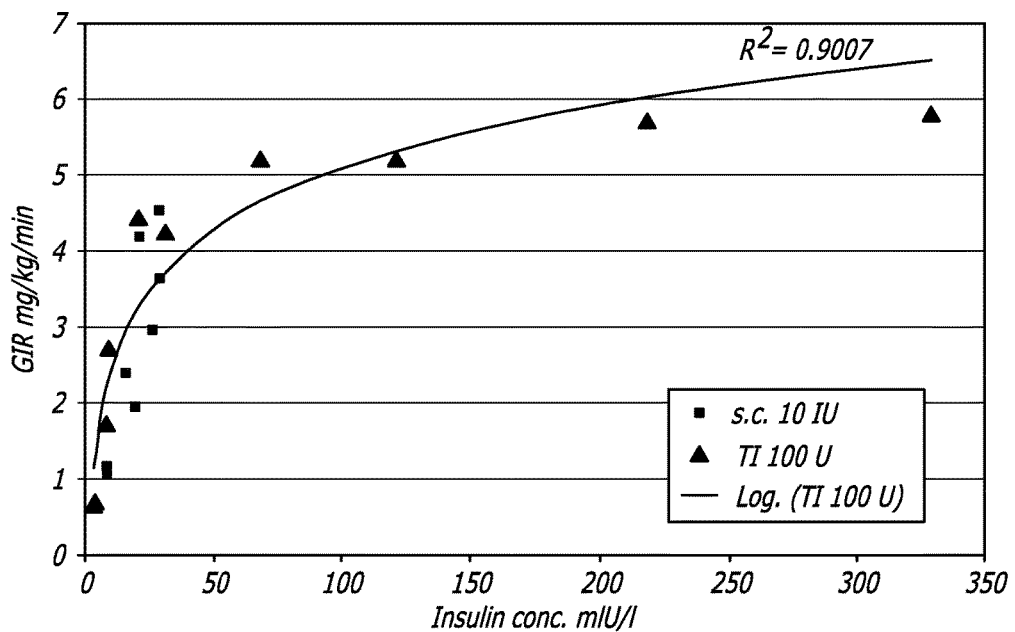
FIG. 15 depicts the relationship between insulin concentration and glucose elimination rate in individuals with type 2 diabetes mellitus after administration of intravenous (IV, 5 IU), SC (10 IU) or inhaled (TI, 100 U) insulin according to the teachings of the present invention.

It might be feared that the large concentrations of insulin, especially combined with their potentiation effect, would drive glucose elimination rates so high that they would pose a danger of inducing hypoglycemia. However this is not the case. Healthy human subjects under a euglycemic clamp were given intravenous, subcutaneous, or pulmonary insulin and the GIR was plotted against blood insulin concentration starting 20 minutes after administration. In normal subjects GIR hysteresis in response to insulin is much less pronounced than that for type 2 diabetics as disclosed in Example 1 above. Thus for normal subjects, 20 minutes after insulin administration and onward the relation between GIR and insulin concentration approximates a true mathematical function. It was observed that while at lower insulin concentrations the function appeared linear, consideration of higher concentrations showed that the relationship was actually logarithmic; as insulin concentration rose, ever smaller increases in GIR were obtained (FIG. 15). Thus glucose elimination did not reach catastrophically high rates and appeared unable to do so.

Example 4

Figure 6A:
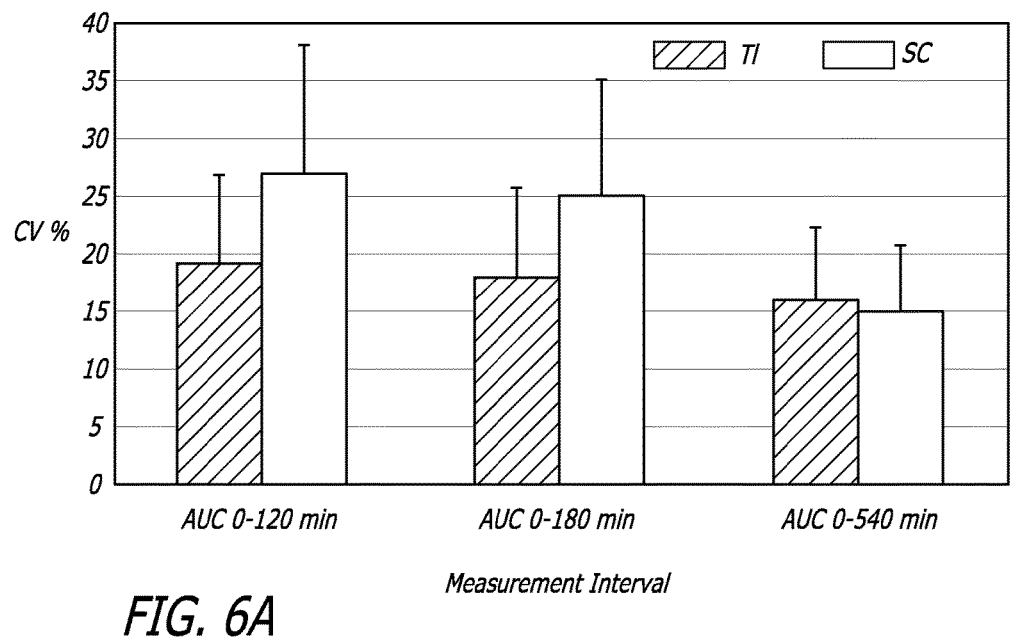
FIGS. 6A-B depict comparisons in intra-patient variability in GIR (FIG. 6A) and insulin concentration (FIG. 6B) in individuals with type 2 diabetes mellitus at various time points for subcutaneous (SC) and pulmonary (TI) insulin according to the teachings of the present invention.
Figure 6B:
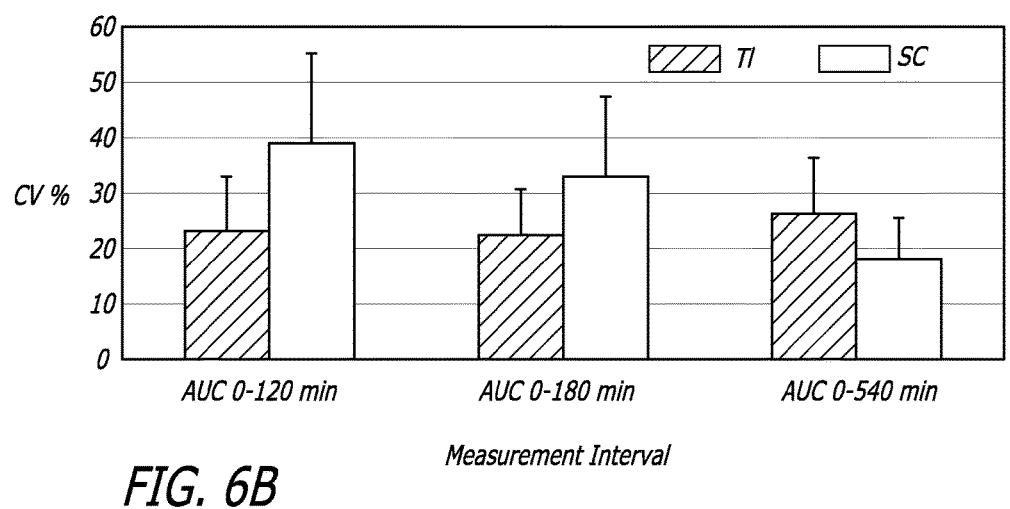

The Variability and Time-Action Profile of Inhaled Technosphere/Insulin Compares Favorably to that of Subcutaneously Administered Human Insulin Reproducibility of insulin's metabolic effect is critical to appropriate dose adjustment decisions including the selection of dose titration intervals and absolute dose quantity, in particular when near-normal glucose control is the objective. The intra-subject variability in insulin absorption and insulin effect between repeated doses of 48 U Technosphere®/Insulin and 24 IU subcutaneously injected human insulin (SC, Actrapid®) were compared. Each dose was given on three separate occasions on separate study days in a randomized sequence. Using a euglycemic glucose clamp, insulin concentrations and glucose infusion rates were measured over 540 min following each form of insulin administration (see FIG. 6). Variability of absorption and effect, expressed as CV % of $AUC_{0-t}$, was determined at 120, 180 and 540 min after dosing. For TI, the variability in insulin effect (GIR) was 23%, 22% and 26% at 120, 180 and 540 min respectively, as compared to 39%, 33% and 18% for SC (FIG. 6A). The variability in insulin concentrations (FIG. 6B) followed a similar pattern (19%, 18% and 16% for TI and 27%, 25% and 15% for SC). Thus for the glucose lowering effect, repeated inhalations of TI exhibited advantageous intra-patient variability compared to SC insulin during the first three hours after dosing. At 270 min, GIR for TI had returned to baseline, and the variability in measured plasma insulin at 540 min was comparable to the variation of SC insulin.

Example 5

A Randomized, Double-Blind, Placebo Controlled Study of the Efficacy and Safety of Inhaled Technosphere®/Insulin in Patients with Type 2 Diabetes Technosphere dry powder, pulmonary insulin delivered via the small MannKind™ inhaler has a bioavailability that mimics normal, meal-related, first- or early-phase insulin release. This multicenter, randomized, double-blind, placebo-controlled study was conducted in type 2 diabetes mellitus patients inadequately controlled on diet or oral agent therapy (HbA1c>6.5% to 10.5%). A total of 123 patients were enrolled and 119, the intention-to-treat population (ITT), were randomized in a 1:1 ratio to receive prandial inhaled Technosphere®/Insulin (TI) from unit dose cartridges containing between 6 to 48 units of human insulin (rDNA origin) or inhaled Technosphere/placebo for 12 weeks. TI was inhaled at the time of the first mouthful of food at each main or substantive meal of the day, amounting to 3 or 4 administrations per day throughout the 12 week trial. Subjects continued whatever oral diabetes drugs they were using prior to entering the study. Differences in HbA1c from the first and final treatment visits, and between the first and two intermediate visits, were determined, as was the change in blood glucose, as AUC at various time points, and $C_{max}$ and $T_{max}$, after a meal challenge.

Patients were given a standardized meal several times during the study and their blood glucose levels measured. The study drug was administered at the study site in conjunction with a standardized breakfast (Uncle Ben's Breakfast Bowl™) that was prepared at the site. Fasting plasma glucose was measured immediately before the meal. Spirometry was performed before the subject took the first dose of study drug. Subjects then inhaled the study drug and, within 60 seconds, performed a single spirometry test procedure. Within 90 seconds of the study drug inhalation, and after the spirometry test, the subject began eating the test meal. Once the meal was completed, the plasma glucose values and glucose meter readings were obtained at immediately before and at 30, 60 and 120 minutes after beginning the meal.

Figure 11:
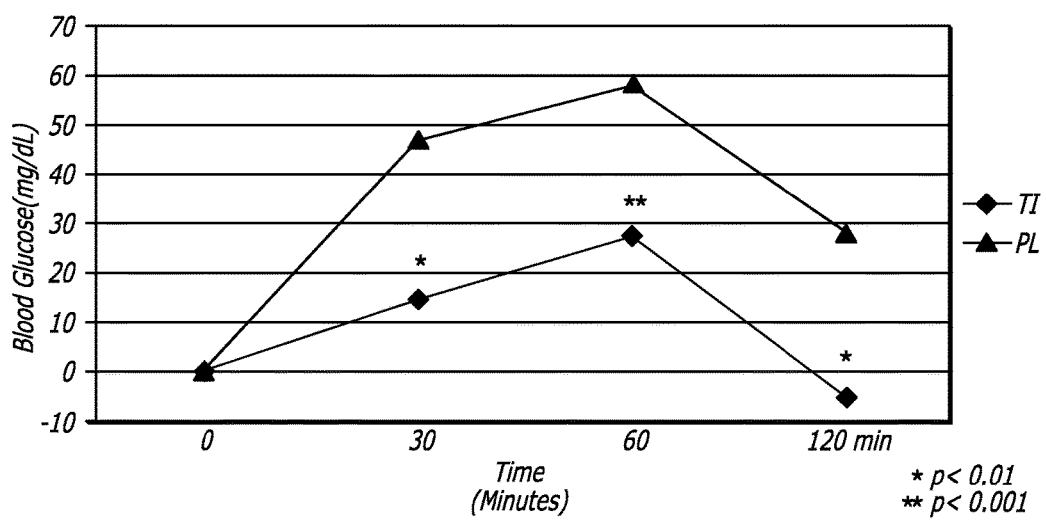
FIG. 11 depicts maintenance of the effects of inhaled insulin postprandial glucose levels after three months of insulin therapy in individuals with type 2 diabetes mellitus with Technosphere®/Insulin (TI) or placebo (PL) according to the teachings of the present invention.
Figure 12A:
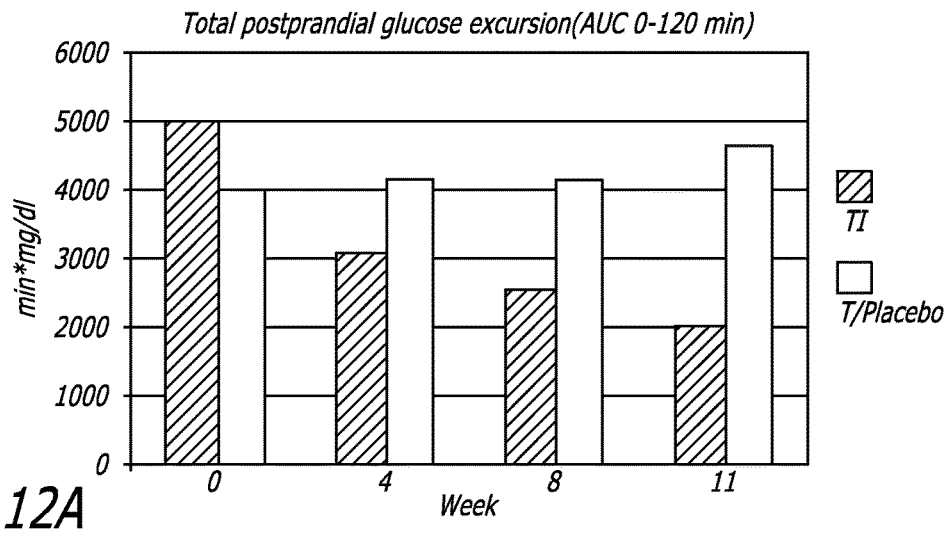
FIGS. 12A-B depict total (FIG. 12A) and maximum (FIG. 12B) postprandial glucose excursion in individuals with type 2 diabetes mellitus after administration of Technosphere®/Insulin (TI) or placebo (PL) according to the teachings of the present invention.
Figure 12B:
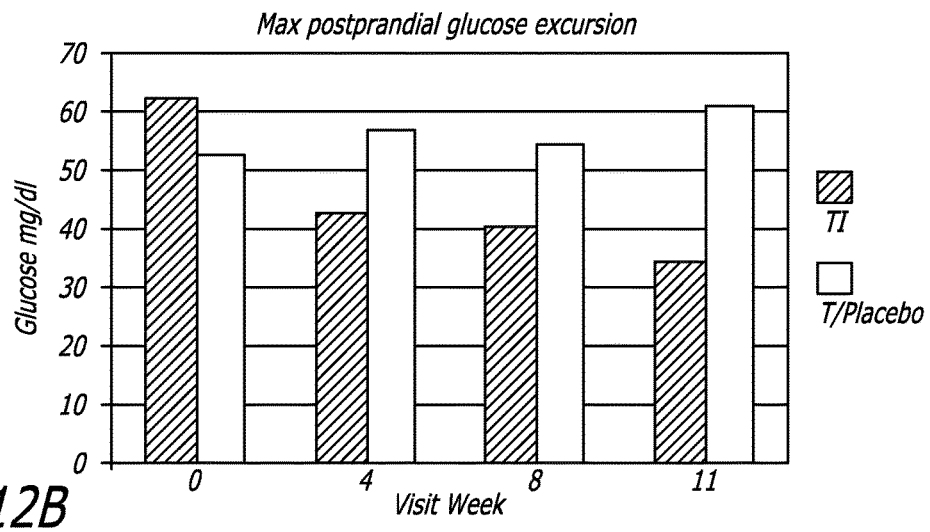
Figure 13:
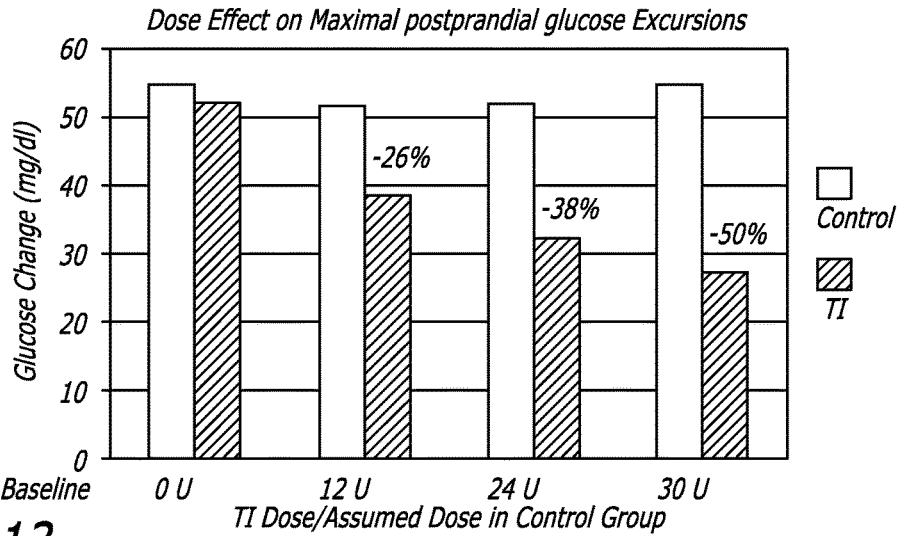
FIG. 13 depicts the dose effect on maximal postprandial glucose excursions after administration of Technosphere®/Insulin (TI) compared to the assumed dose in a control group (Control) in individuals with type 2 diabetes mellitus according to the teachings of the present invention.

For patients receiving either TI or placebo, blood glucose rose after meal challenge, but significantly less for the TI group and returned to baseline sooner (FIG. 11). Thus total glucose exposure, expressed as $AUC_{0-120}$, (FIG. 12A) and maximal glucose excursion ($C_{max}$; FIG. 12B) were reduced. FIG. 13 shows the observed difference in maximal glucose excursions between the patients receiving different dosages of TI versus those in the control arm. Note that at a dose of 30 U the maximal glucose excursions for the TI patients were 50% of the level for the patients in the control group. Also note that the average glucose excursion was about 28 mg/dL vs. 50 mg/dL when the TI patients entered the study. An excursion of only 28 mg/dL is within the range that is a goal of clinical treatment.

Figure 17:
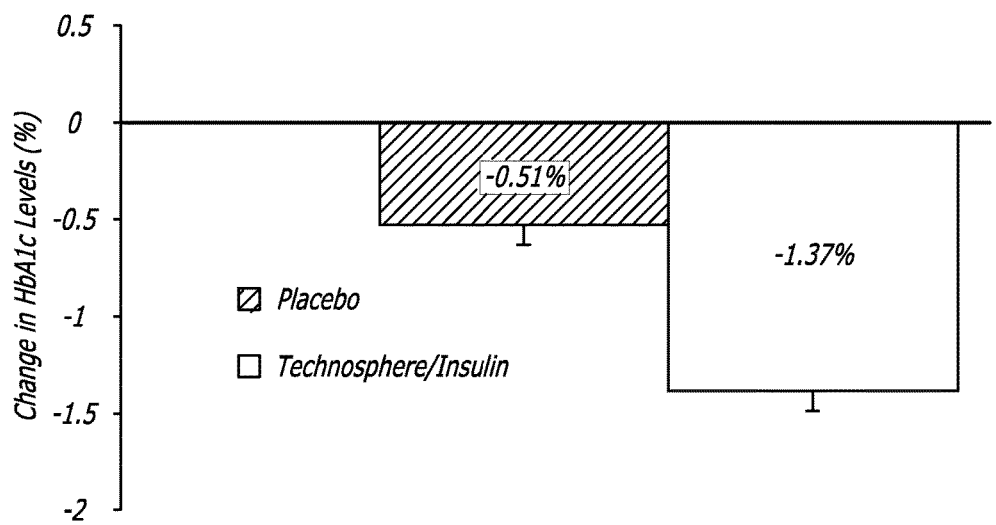
FIG. 17 depicts the change in mean glycosylated hemoglobin (HbA1c) levels after 12 weeks of administration of Technosphere®/Insulin (TI) or placebo in individuals with type 2 diabetes mellitus according to the teachings of the present invention.

Glycosylated hemoglobin A1c (HbA1c) results were analyzed by a pre-determined statistical analysis plan for the Primary Efficacy Population (PEP, defined prior to unblinding as those who adhered to study requirements including minimal dosing and no adjustments of concomitant diabetes drugs), for a PEP Sub-group A (those with baseline HbA1c of 6.6 to 7.9%), for a PEP Sub-group B (those with baseline HbA1c of 8.0 to 10.5%), as well as for the ITT. These results are summarized in Table 1, and for PEP Sub-group B in FIG. 17. In this "individualized dose" study, the mean dose of TI used before each meal in the active treatment group was approximately 30 units, with 28 units used in PEP Sub-group A and 33.5 units used in PEP Sub-group B.

TABLE 1

HbA1c Pharmacokinetics

|  | Technosphere ®/Placebo | Technosphere ®/Insulin |
|---|---|---|
| PEP n = 90 | n = 42 | n = 48 |
| Mean HbA1c Baseline (%) | 7.75 | 7.74 |
| Mean Δ from baseline | −0.32 (p = 0.0028) | −0.76 (p < 0.0001) |
| Comparison to Placebo |  | p = 0.0019 |
| PEP Sub-group B n = 35 | n = 18 | n = 17 |
| Mean HbA1c Baseline (%) | 8.52 | 8.72 |
| Mean Δ from baseline | −0.51 (p = 0.0094) | −1.37 (p < 0.0001) |
| Comparison to Placebo |  | p = 0.0007 |
| PEP Sub-group A n = 55 | n = 24 | n = 31 |
| Mean HbA1c Baseline (%) | 7.16 | 7.19 |
| Mean Δ from baseline | −0.18 (p = 0.1292) | −0.43 (p = 0.0001) |
| Comparison to Placebo |  | p < 0.05 |
| ITT (LOCF) n = 119 | n = 61 | n = 58 |
| Mean HbA1c Baseline (%) | 7.78 | 7.87 |
| Mean Δ from Baseline (%) | −0.31 (p = 0.0020) | −0.72 (p < 0.0001) |
| Comparison to Placebo |  | p = 0.0016 |

No episodes of severe hypoglycemia occurred in the TI group. There was no statistically significant difference in the rate of hypoglycemic events between those subjects receiving placebo and those receiving TI. (Table 2).

TABLE 2

Incidence of Hypoglycemia after Pulmonary Administration of TI

|  | Technosphere ®/Insulin | Technosphere ®/Placebo |
|---|---|---|
| Hypoglycemia (% of patients) | 42.6% | 35.5% |
| Hypoglycemia (events/week) | 0.16 | 0.20 |

Figure 19A:
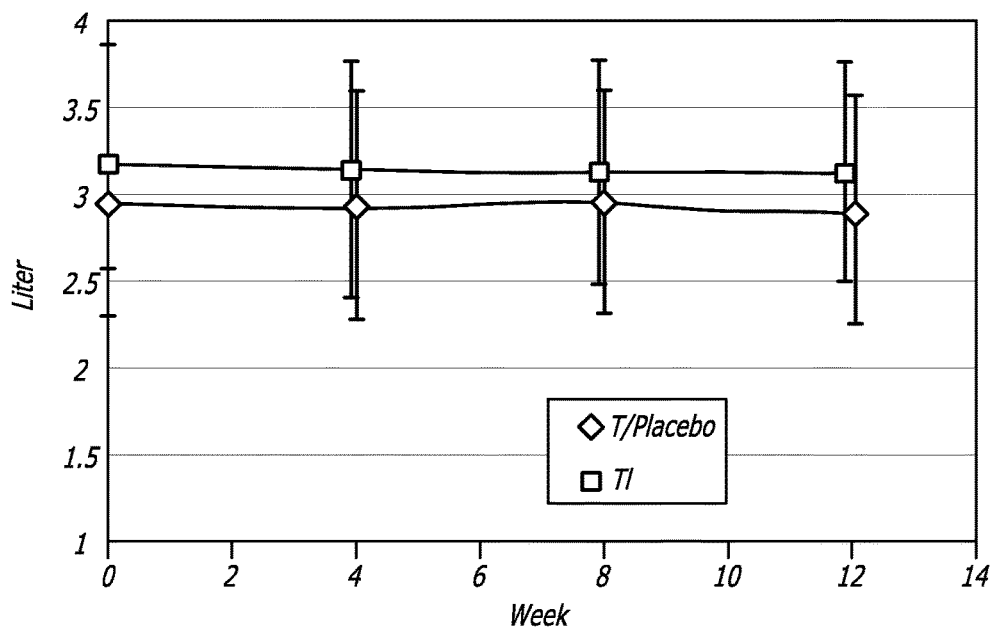
FIGS. 19A-B depict pulmonary function, expressed as forced expiratory volume in one second (FEV1, FIG. 19A)
Figure 19B:
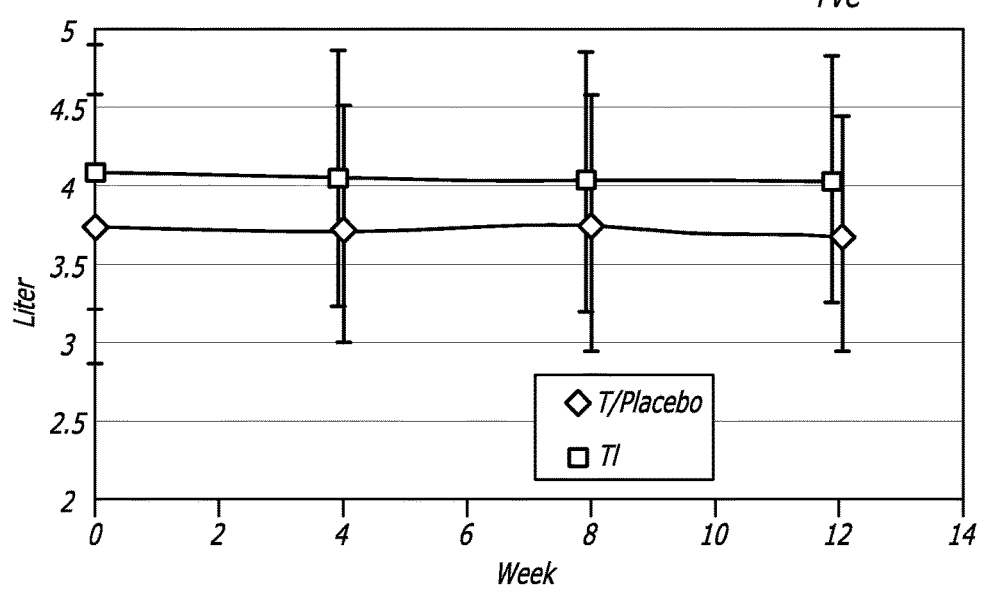

Pulmonary function tests, including DLco (diffusing capacity of the lung for carbon monoxide) (Table 3), FEV1 (forced expiratory volume in one second), and total alveolar volume (forced vital capacity, FVC) showed no significant differences between patients on TI compared to their baseline values or compared to the results of those receiving placebo (FIG. 19).

TABLE 3

Pulmonary Function After Pulmonary Administration of TI

| DLco | Technosphere ®/Insulin | Technosphere ®/Placebo |
|---|---|---|
| 0 weeks | 24.9 ± 4.8 | 26.5 ± 5.6 |
| 12 weeks | 25.0 ± 4.5 | 25.7 ± 5.2 |

Figure 18:
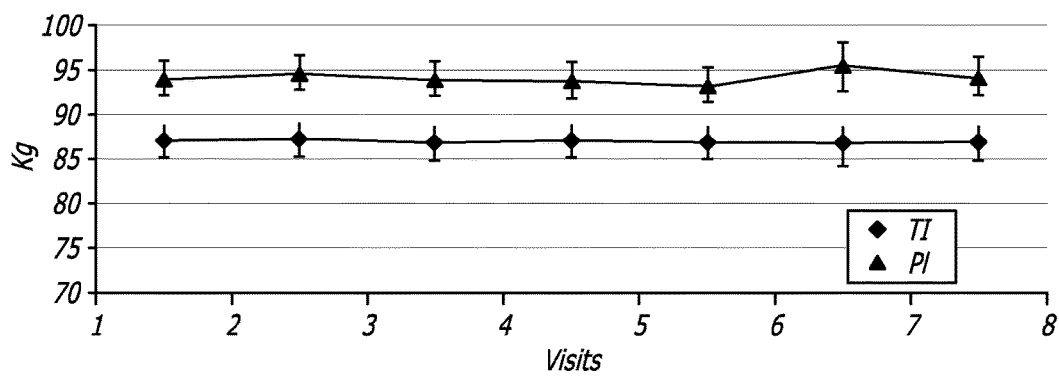
FIG. 18 depicts weight levels in individuals with type 2 diabetes mellitus administered Technosphere®/Insulin (TI) or placebo (PL) according to the teachings of the present invention.

There was no evidence of induction of insulin antibodies with TI (Table 4) or of weight gain (FIG. 18) during the 12 week period of exposure.

TABLE 4

Incidence of Antibodies to Insulin after
Pulmonary Administration of TI

| | Techno-sphere ®/Insulin | Techno-sphere ®/Placebo |
|---|---|---|
| Negative at Visit 1/Negative at Visit 9 | 38 | 34 |
| Negative at Visit 1/Positive at Visit 9 | 2 | 3 |
| Positive at Visit 1/Positive at Visit 9 | 8 | 10 |
| Positive at Visit 1/Negative at Visit 9 | 2 | 4 |

In conclusion, this study has demonstrated that Technosphere® pulmonary insulin, in replication of the kinetics of the early phase of insulin release, when used in patients with inadequate glycemic control previously on only diet and exercise alone or on oral agent therapy, safely and significantly improved glycemic control with no significantly increased incidence of hypoglycemia, no induction of insulin antibodies, no tendency toward weight gain, and no evidence of overall impact on pulmonary function.

Example 6

A FDKP/Insulin Provides Glycemic Control when Administered from 10 Minutes Before to 30 Minutes after the Beginning of a Meal A clinical trial was conducted to evaluate the effect of the timing of pulmonary administration of an FDKP-insulin complex as a dry powder (FDKP/Insulin; also referred to as Technosphere®/Insulin, TI). Subjects were type 1 diabetics who were not receiving any drug, other than insulin, for treatment of their diabetes, nor any other drug affecting carbohydrate metabolism. The trial was a prospective, single-center, randomized, crossover, open-label study. At each of 8 treatment visits, human subjects inhaled a single individualized dose 10 min before (B10), immediately before (C0), 15 min after (A15), or 30 min after (A30) eating an isocaloric (I; approximately 500 kcal) or hypercaloric (H; approximately 720 kcal) meal. Each subject received each of the eight possible timings of administration/meal combinations (i.e., B10I, B10H, C0I, C0H, A15I, A15H, A30I, and A30H) on separate occasions and in random order, with 1 to 14 days elapsing between treatment visits (see FIG. 20). Blood samples taken before and after inhalation of the TI and meal consumption were used to determine pharmacokinetic parameters for glucose and insulin.

The dose of TI was individualized for each subject. The individualized dose was based on the carbohydrate content of the meal to be consumed during the treatment visit, a correction factor for TI bioavailability, and the subject's individual "insulin factor" (Fi), which was determined during a preliminary visit before the first treatment visit. The method of dose individualization was calculated at each treatment visit according to the following formula:

$$IUdose = (BE * Fi)/0.30$$

where:
IUdose was the number of IU of TI to be administered
BE (Brot-Einheit, bread unit) was 1/10 of the carbohydrate content (in grams) of the meal to be consumed (5 for the isocaloric and 8.5 for the hypercaloric meals, respectively)

Fi was the individual insulin factor, equivalent to the units of insulin required to cover one BE.
0.30 was the correction factor for TI bioavailability.
After calculation, the dose of TI was rounded to the nearest dose that could be administered using multiples of the TI cartridges, which contained 6 U, 12 U, or 24 U insulin.

During treatment visits, insulin was infused intravenously at a rate of 1 IU/hour and glucose was infused at a rate adjusted to achieve a stable capillary blood glucose concentration within the range of 80 to 140 mg/dL before meal consumption and/or TI inhalation. This infusion was continued without adjustment during the study. Venous blood samples were collected at varying intervals, starting at 45 min prior to meal consumption and continuing until four hours after consumption. The samples were used for determination of blood (serum) glucose and serum insulin concentrations.

The primary efficacy variable was blood glucose concentration. As well as providing a profile of the blood glucose concentration before and after TI and meal administration, the blood glucose concentration values were used to calculate the following pharmacokinetic parameters to describe total glucose excursion:

Maximal (Cmax) and minimal (Cmin) blood glucose concentrations after the start of meal consumption, corrected for baseline values.

Minimal (Cmin) blood glucose concentrations after TI inhalation, corrected for baseline values.

Time to Cmax (Tmax), time to Cmin (Tmin), and time to last glucose excursion above baseline levels after start of meal ($T_X$).

Area under the blood glucose concentration curve (AUC) was calculated using trapezoidal method for three separate time periods:
AUC: from 10 min before to 240 min after start of meal
AUC1: from 10 min before to $T_X$, and
AUC2: from $T_X$ to 240 min after start of meal.

Blood glucose concentration at 1 hour (BG1) and 2 hours (BG2) after start of meal.

To ensure baselines were comparable between treatments, blood glucose and serum insulin baselines were computed based on the average of the −45, −30 and −20 min pre-meal measurements.

The secondary efficacy variable was serum insulin concentration. Insulin absorption was assumed to be independent of the time of dose relative to meals. The pharmacokinetic profile for insulin was determined based on serum insulin values normalized for dose and using dosing time as T=0 for all data sets. Mean Cmax (peak insulin concentration), AUC (area under the insulin concentration time curve), Tmax (time from dosing to peak concentration), time from dosing to reach 50% of Cmax (early T50%), and time from Tmax to 50% decline in Cmax (late T50%) were calculated. Following normalization (to a hypothetical 100 IU) for individual dose, intra- and inter-individual variation was determined as the CV % for the mean of individual Cmax and AUC.

The primary efficacy variable was blood glucose concentration. The effect of timing of administration of TI on the mean (SD) baseline-corrected blood glucose concentrations before and after an isocaloric or hypercaloric meal is illustrated in FIG. 21 for the primary efficacy population. Overall, the comparative excursions in blood glucose, while greater after the hypercaloric meal than the isocaloric meal, were similar in profile for the two meal types but were dependent upon the timing of administration of TI (FIG. 21).

Notably, when TI was inhaled 10 min before either meal, there was an initial decrease in blood glucose levels. After reaching a nadir about 10 min after the start of the meal, blood glucose levels rose above baseline levels approximately 30 min later. By comparison, when TI was inhaled 15 or 30 min after the start of the meal, glucose levels rose above baseline approximately 10-15 min after starting meal consumption (FIG. 21).

A comparison of pharmacokinetic parameters for blood glucose following each type of meal and for each timing of administration of TI is shown in Table 5 for the primary efficacy population. As indicated by the mean minimum blood glucose levels (Cmin, expressed as change from baseline) and initial period of the area under the glucose concentration curve (AUC1), the greatest reduction in blood glucose occurred when TI was inhaled 10 min before subjects started eating either the isocaloric or hypercaloric meal (Cmin −21 mg/dL and −27 mg/dL, respectively; AUC1 −722 and −907 min*mg/dL, respectively) (Table 5). When TI was inhaled either 10 min before or immediately before meal consumption, blood glucose levels reached a nadir in approximately 10 to 13 min (as indicated by the median Tmin), and did not rise above baseline levels until 20 to 30 min later (as indicated by the median TX) (Table 5). By comparison, when TI was inhaled either 15 min or 30 min after the start of meal consumption, reductions in blood glucose were smaller (Cmin −10 to −13 mg/dL; AUC1 −141 to −176 min*mg/dL), they occurred sooner (Tmin 3 to 5 min), and they were more short-lived (approximately 6 to 7 min). The largest individual reductions in blood glucose were in subjects who inhaled TI immediately before isocaloric or hypercaloric meal consumption (Cmin −58 mg/dL and −57 mg/dL, respectively).

Mean Cmax values (expressed as change from baseline), AUC, and AUC2 were generally comparable whether TI was given before or after a particular type of meal, though all were lower after the isocaloric meal than the hypercaloric meal (Table 5). The median time to Cmax (Tmax) ranged between 120 and 165 min for the isocaloric meal and between 150 to 180 min for the hypercaloric meal. Mean blood glucose levels one hour (BG1) and two hours (BG2) after the start of meal showed no consistent relationship to time of inhalation of TI relative to either meal (Table 5), although BG1 was lowest when TI was given 10 min before the start of a meal and highest when given 30 min after the start of a meal.

The comparative effects of different times of TI inhalation on selected glucose pharmacokinetic parameters was expressed as a ratio of the value at the corresponding C0 (i.e, B10/C0, A15/C0, and A30/C0) for each meal type. These ratios, along with their 95% confidence intervals (CI), are summarized in Table 6 (primary efficacy population). These results indicated that the comparative effects of inhalation of TI immediately before meal consumption were no different than that of inhalation 10 min before meal consumption on any pharmacokinetic parameter (i.e, most B10/C0 ratios were close to 1 and the 95% CI encompassed 1 within their range). Most comparisons also yielded no differences between TI immediately before meal consumption and 15 or 30 min after.

TABLE 5

Summary of Bluclose Blood Glucose Pharmacokinetic Parameters by Meal and Timing of Administration of Technosphere ®/Insulin

| Parameter | Isocaloric Meal Timing of Dosing | | | | Hypercaloric Meal Timing of Dosing | | | |
|---|---|---|---|---|---|---|---|---|
| | B10 (N = 12) | C0 (N = 12) | A15 (N = 12) | A30 (N = 12) | B10 (N = 12) | C0 (N = 12) | A15 (N = 12) | A30 (N = 12) |
| $C_{min}$ (mg/dL) | −21 | −18 | −11 | −13 | −27 | −16 | −11 | −10 |
| | (14) | (15) | (14) | (7) | (8) | (14) | (7) | (7) |
| $T_{min}$ (minutes) | 10 | 13 | 5 | 5 | 13 | 10 | 5 | 3 |
| $C_{max}$ (mg/dL) | 86 | 84 | 88 | 81 | 119 | 130 | 116 | 113 |
| | (28) | (38) | (36) | (23) | (46) | (40) | (50) | (47) |
| $T_{max}$ (minutes) | 165 | 135 | 150 | 120 | 180 | 180 | 150 | 165 |
| AUC1 (min*mg/dL) | −722 | −648 | −154 | −176 | −907 | −418 | −149 | −141 |
| | (950) | (840) | (180) | (176) | (511) | (549) | (148) | (149) |
| AUC2 (min*mg/dL) | 11499 | 10989 | 13055 | 12431 | 14818 | 17395 | 16346 | 18402 |
| | (4640) | (7030) | (7616) | (4682) | (6018) | (6050) | (8326) | (8968) |
| AUC (min*mg/dL) | 10777 | 10342 | 12901 | 12255 | 13911 | 16977 | 16197 | 18261 |
| | (5339) | (7349) | (7739) | (4895) | (5840) | (6008) | (8407) | (8982) |
| BG1 (mg/dL) | 21 | 23 | 41 | 55 | 16 | 33 | 38 | 65 |
| | (32) | (25) | (32) | (23) | (23) | (21) | (31) | (24) |
| BG2 (mg/dL) | 68 | 71 | 78 | 68 | 81 | 101 | 82 | 89 |
| | (34) | (34) | (32) | (32) | (28) | (33) | (47) | (46) |
| $T_x$ (minutes) | 36.6 | 36.9 | 11.7 | 11.3 | 42.2 | 33.2 | 12.4 | 10.3 |

All values are presented as mean (SD) except for $T_{min}$, $T_{max}$ and $T_x$, which are median.

TABLE 6

Comparison of Blood Glucose Pharmacokinetic Parameters Relative to
Inhalation of Technosphere ®/Insulin Immediately Before Meal Consumption

| | Isocaloric Meal Ratio of Test to Reference Parameter | | | Hypercaloric Meal Ratio of Test to Reference Parameter | | |
|---|---|---|---|---|---|---|
| Parameter | B10/C0 (N = 12) | A15/C0 (N = 12) | A30/C0 (N = 12) | B10/C0 (N = 12) | A15/C0 (N = 12) | A30/C0 (N = 12) |
| $C_{min}$ | 0.997 | 0.425 | 0.581 | 1.748 | 0.988 | 0.532 |
| | (0.470, 2.112) | (0.210, 0.860) | (0.302, 2.112) | (0.470, 2.112) | (0.470, 2.112) | (0.470, 2.112) |
| AUC1 | 0.608 | 0.300 | 0.214 | 1.995 | 0.381 | 0.334 |
| | (0.133, 2.775) | (0.067, 1.334) | (0.053, 0.863) | (0.803, 4.762) | (0.154, 0.942) | (0.137, 0.814) |
| $C_{max}$ | 1.002 | 1.088 | 0.953 | 0.848 | 0.778 | 0.814 |
| | (0.809, 1.240) | (0.887, 1.334) | (0.784, 1.157) | (0.630, 1.143) | (0.581, 1.041) | (0.616, 1.076) |
| AUC2 | 1.077 | 1.035 | 1.158 | 0.780 | 0.771 | 0.907 |
| | (0.727, 1.596) | (0.711, 1.506) | (0.809, 1.657) | (0.497, 1.226) | (0.496, 1.198) | (0.594, 1.385) |
| AUC | 1.105 | 0.722 | 1.245 | 0.727 | 0.753 | 0.910 |
| | (0.555, 2.200) | (0.378, 1.380) | (0.671, 2.310) | (0.426, 1.238) | (0.448, 1.266) | (0.553, 1.500) |
| BG1 | 0.833 | 1.203 | 7.932 | 0.768 | 1.256 | 1.985 |
| | (0.451, 1.536) | (0.656, 2.207) | (1.143, 3.267) | (0.491, 1.200) | (0.810, 1.948) | (1.379, 2.857) |
| BG2 | 0.630 | 1.109 | 0.906 | 0.771 | 0.665 | 0.758 |
| | (0.258, 1.536) | (0.468, 2.627) | (0.399, 2.058) | (0.533, 1.114) | (0.464, 0.953) | (0.537, 1.069) |

All values are presented as ratio (95% confidence interval).

The secondary efficacy variable was serum insulin concentration. The profile of the mean (SD) baseline-corrected serum insulin concentrations after TI inhalation is illustrated in FIG. 22 for the primary efficacy population. There was a sharp increase in serum insulin immediately after inhalation of TI, which was independent of dosing time and meal type. Serum insulin concentrations peaked approximately 15 min after dosing and thereafter rapidly declined until 60 min after administration, after which there was a slower decline, consistent with first-order elimination.

A comparison of pharmacokinetic parameters for serum insulin for each timing of administration of TI relative to each type of meal is shown in Table 7 for the primary efficacy population. Overall, the mean Cmax (expressed as change from baseline) and AUC values for serum insulin were generally comparable, irrespective of meal type and whether TI was given before or after the meal (Table 7). Irrespective of meal type and time of dosing relative to the meal, serum insulin concentrations rose rapidly after TI inhalation, with the early T50% ranging between three and five min and peak concentrations being observed 10 to 20 min after administration. Thereafter, serum insulin concentrations declined, with the late T50% ranging between 33 and 43 min, and again showed no consistent variation with time of inhalation of TI or meal type (Table 7).

Thus inhalation of an individualized dose of TI provides glycemic control in subjects with type 1 diabetes who consume isocaloric or hypercaloric meals. There were no differences in the pharmacokinetics of insulin based on the timing of administration relative to the meals. The administration of TI between 10 minutes prior to the time of the first bite of food and up to 30 minutes after starting a meal provides comparable glycemic control in the postprandial period.

Example 7

Bioavailability of Insulin in Diketopiperazine Pulmonary Formulation

Subjects and Methods

The study was reviewed and approved by the ethical review committee of the Heinrich-Heine-University, Dusseldorf, and conducted according to local regulations, the Declaration of Helsinki and the rules of Good Clinical Practice.

The study was conducted with 5 healthy male volunteers. Inclusion criteria were good health, as judged by physical examination, age: 18 to 40 years, body mass index: 18 to 26 kg/m², capability to reach peak inspiratory flow of ≥4 L/sec

TABLE 8

Summary of Serum Insulin Pharmacokinetic Parameters by Meal and
Timing of Administration of Technosphere ®/Insulin

| | Isocaloric Meal Timing of Dosing | | | | Hypercaloric Meal Timing of Dosing | | | |
|---|---|---|---|---|---|---|---|---|
| Parameter | B10 (N = 12) | C0 (N = 12) | A15 (N = 12) | A30 (N = 12) | B10 (N = 12) | C0 (N = 12) | A15 (N = 12) | A30 (N = 12) |
| $C_{max}$ (mIU/L) | 207 | 179 | 188 | 215 | 211 | 137 | 191 | 193 |
| | (145) | (125) | (137) | (196) | (138) | (74) | (114) | (163) |
| $T_{max}$ (minutes) | 13 | 15 | 15 | 15 | 10 | 20 | 15 | 15 |
| AUC (min*mIU/L) | 12635 | 11291 | 11642 | 12649 | 10654 | 7710 | 12874 | 11662 |
| | (15681) | (17449) | (18373) | (14838) | (7623) | (7313) | (16785) | (13210) |
| Early $T_{50\%}$ (min) | 4 | 4 | 3 | 3 | 4 | 5 | 4 | 3 |
| Late $T_{50\%}$ (min) | 40 | 40 | 33 | 43 | 43 | 42 | 39 | 39 |

All values are presented as mean (SD) except for $T_{max}$ and $T_{50\%}$, which are median.

measured by a computer assisted spirometry and a FEV1 equal to or greater than 80% of predicted normal (FEV1=forced expiratory volume in one second). Exclusion criteria were diabetes mellitus type 1 or 2, prevalence of human insulin antibodies, history of hypersensitivity to the study medication or to drugs with similar chemical structures, history or severe or multiple allergies, treatment with any other investigational drug in the last three months before study entry, progressive fatal disease, history of drug or alcohol abuse, current drug therapy with other drugs, history significant cardiovascular, respiratory, gastrointestinal, hepatic, renal, neurological, psychiatric and/or hematological disease, ongoing respiratory tract infection or subjects defined as being smokers with evidence or history of tobacco or nicotine use.

Conduct of the Study

On the morning of the study days, the subjects came to the hospital (fasting, except for water, from midnight onward) at 7:30 a.m. The subjects were restricted from excessive physical activities and an intake of alcohol for 24 hours before each treatment day. They were randomly assigned to one of the three treatment arms. The subjects received a constant intravenous regular human insulin infusion, which was kept at 0.15 mU min$^{-1}$ kg$^{-1}$ so that serum insulin concentrations were established at 10-15 μU/mL during a period of two hours before time point 0. This low-dose infusion was continued throughout the test to suppress endogenous insulin secretion. Blood glucose was kept constant at a level of 90 mg/dL throughout the glucose clamp by a glucose controlled infusion system (Biostator™). The glucose clamp algorithm was based on the actual measured blood glucose concentration and the grade of variability in the minutes before to calculate the glucose infusion rates for keeping the blood glucose concentration constant. The insulin application (5 IU IV or 10 IU SC injection or three deep breaths inhalation per capsule (2 capsules with 50 U each) applied with a commercial inhalation device (Boehringer Ingelheim)) had to be finished immediately before time point 0. The duration of the clamp experiment was six hours from time point 0. Glucose infusion rates, blood glucose, serum-insulin and C-peptide were measured.

Bioefficacy and Bioavailability

To determine bioefficacy, the areas under the curve of the glucose infusion rates were calculated for the first three hours (AUC0-180) after the administration and for the overall observation period of six hours after the administration (AUC0-360) and were correlated to the amount of insulin applied. To determine bioavailability, the areas under the curve of the insulin concentrations were calculated for the first three hours (AUC0-180) after the administration and for the overall observation period of six hours after the administration (AUC0-360) and correlated to the amount of insulin applied.

In this clamp study, inhalation of 100 U of Technosphere®/Insulin was well tolerated and was demonstrated to have a substantial blood glucose lowering effect with a relative bioavailability of 25.8% for the first three hours as calculated from the achieved serum insulin concentrations. Technospheres® are microparticles (also referred to herein as microspheres) formed of diketopiperazine that self-assembles into an ordered lattice array at particular pHs, typically a low pH. They typically are produced to have a mean diameter between about 1 and about 5 μm.

Results

The pharmacokinetic results are illustrated in FIGS. 23 and 24 and in Table 8.

Efficacy Results

Inhalation of 100 U of Technosphere®/Insulin revealed a peak of insulin concentration after 13 min (intravenous (IV) (5 IU): 5 min, subcutaneous (SC) (10 IU): 121 min) and a return of the insulin levels to baseline after 180 min (IV: 60 min, SC: 360 min). Biological action as measured by glucose infusion rate peaked after 39 min IV: 14 min, SC: 163 min) and lasted for more than 360 min (IV: 240 min, SC: >360 min). Absolute bioavailability (comparison to IV application) was 14.6±5.1% for the first three hours and 15.5±5.6% for the first six hours. Relative bioavailability (comparison to SC application) was 25.8±11.7% for the first three hours and 16.4±7.9% for the first six hours.

TABLE 8

Pharmacokinetic Parameters after Pulmonary Administration of TI

| | Pharmacokinetic Parameters | | |
|---|---|---|---|
| | Intravenous Administration | Inhaled TI | Subcutaneous Administration |
| Parameter Calculated on Glucose Infusion Rate | | | |
| T50%* | 9 min | 13 min | 60 min |
| Tmax | 14 min | 39 min | 163 min |
| T–50%** | 82 min | 240 min | 240 min |
| T to baseline | 240 min | >360 min | >360 min |
| Parameter Calculated on Insulin Levels | | | |
| T50%* | 2 min | 2.5 min | 27 min |
| Tmax | 5 min | 13 min | 121 min |
| T–50%** | 6 min | 35 min | 250 min |
| T to baseline | 60 min | 180 min | 360 min |

*time from baseline to half-maximal values
**time from baseline to half-maximal after passing Tmax Safety Results Technosphere®/Insulin was shown to be safe in all patients. One patient was coughing during the inhalation without any further symptoms or signs of deterioration of the breathing system.

Conclusions

Inhalation of 100 U of Technosphere®/Insulin was well tolerated and was demonstrated to have a substantial blood glucose lowering effect with a relative bioavailability of 25.8% for the first three hours as calculated from the achieved serum insulin concentrations.

Summary

In this study, the inhalation of Technosphere®/Insulin was demonstrated in healthy human subjects to have a time-action profile with a rapid peak of insulin concentration ($T_{max}$: 13 min) and rapid onset of action ($T_{max}$: 39 min) and a sustained action over more than six hours. The total metabolic effect measured after inhalation of 100 U of Technosphere®/Insulin was larger than after subcutaneous injection of 10 IU of insulin. The relative bioefficacy of Technosphere®/Insulin was calculated to be 19.0%, while the relative bioavailability was determined to be 25.8% in the first three hours.

The data also show that inhalation of Technosphere®/Insulin resulted in a much more rapid onset of action than SC insulin injection that was close to the onset of action of IV insulin injection, while duration of action of Technosphere®/Insulin was comparable to that of SC insulin injection.

The drug was well tolerated and no serious adverse events were reported during the entire trial.

Example 8

Prandial Technosphere®/Insulin Provides Significantly Better Control of Meal-Related Glucose Excursions than Prandial Subcutaneous Insulin Technosphere®/Insulin (TI) is a dry powder formulation of human insulin comprising insulin complexed to fumaryl diketopiperazine microparticles. Technosphere®/Insulin was delivered by pulmonary administration with a dry powder inhaler (MedTone® Inhaler) accomplishing a rapid onset of action and a duration of action long enough to cover meal-related glucose absorption. The primary objective of this study was to assess safety and efficacy of pre-prandially administered TI compared to subcutaneous (SC) regular insulin on blood glucose concentration over a 7 day treatment period.

Sixteen non-smoking subjects with Type 2 diabetes (age 59 (range 39-69) yrs; BMI 29.6 (23.8-34.9) kg/m$^2$; mean diabetes duration 12.3 yrs; with normal pulmonary function (forced expiratory volume in 1 sec and forced vital capacity >80% of predicted normal) and treated with intensified insulin therapy were enrolled in this randomized, open-label, two period cross-over study. Subjects covered their prandial insulin needs either by inhaled TI or by SC insulin over a treatment period of one week, respectively, while continuing their usual basal insulin therapy. The doses of TI and SC insulin were determined during a 24 hours in-house period prior to randomization. TI was inhaled using a 12 U or 24 U cartridge via a hand-held inhaler. After an out-patient period during which subjects administered the assigned pre-meal therapy with either SC or TI, performed 4-point blood glucose self-measurements, and pursued their usual activities and diet for 5 to 7 days, postprandial blood glucose and serum insulin (INS) excursions were determined under in-house conditions after ingestion of a standardized breakfast (496 kcal, 55% carbohydrates) covered with either 48±9 (mean±SD) U of TI or 14±5 IU of SC insulin.

Figure 9B:
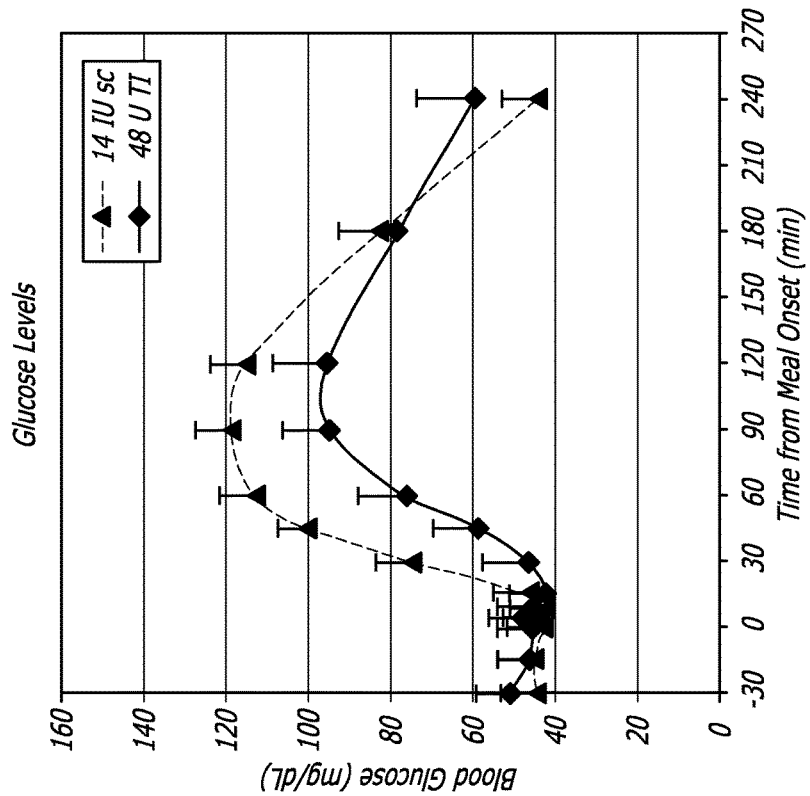
FIGS. 9A-B depict blood insulin (FIG. 9A) and glucose levels (FIG. 9B) in individuals with type 2 diabetes mellitus after administration of 14 IU SC insulin or 48 U Technosphere®/Insulin (TI) according to the teachings of the present invention.
Figure 9A:
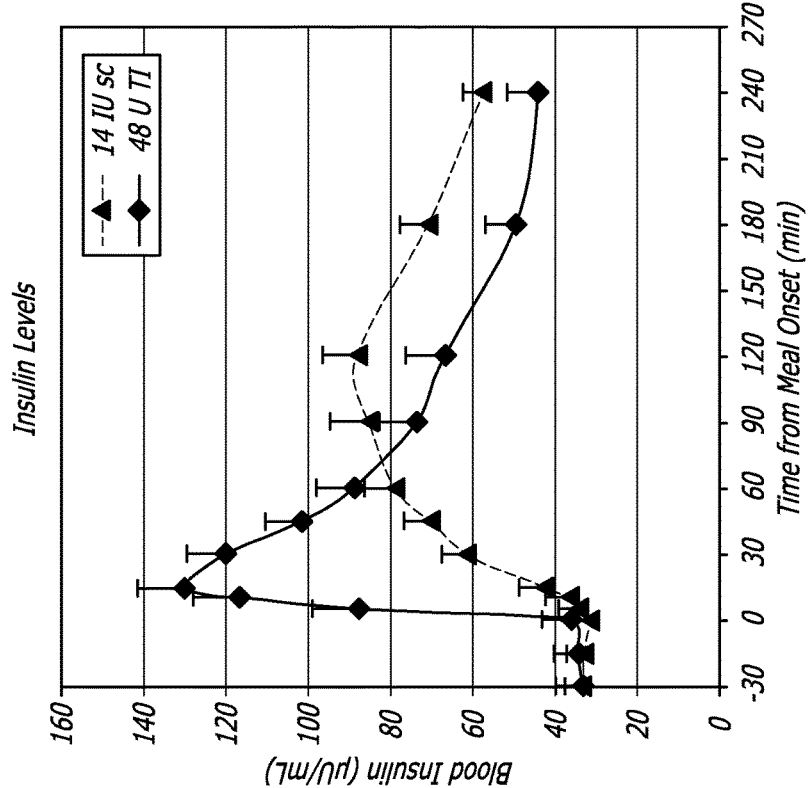
Figure 10:
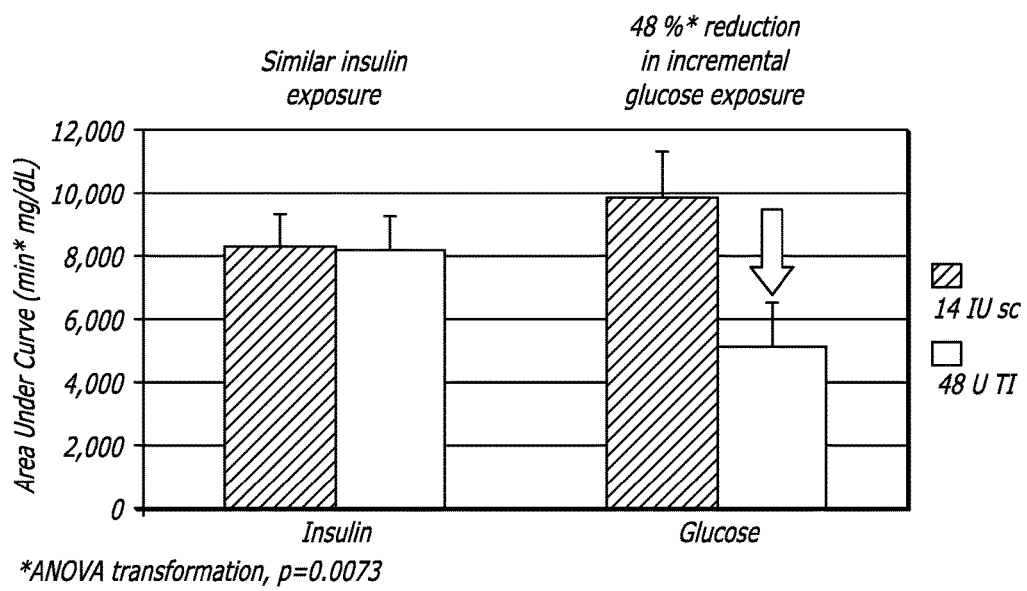
FIG. 10 depicts the improved postprandial glucose exposure with similar insulin exposure in individuals with type 2 diabetes mellitus after administration of 14 IU SC insulin or 48 U Technosphere®/Insulin (TI) according to the teachings of the present invention.

When treated with SC insulin, subjects demonstrated insulin median Tmax of 120 min with median Cmax of 54 µU/mL. In comparison, when treated with TI, subjects demonstrated insulin median Tmax of 14 min and median Cmax of 102 µU/mL (FIG. 9). Total insulin exposure for each treatment cycle was comparable for SC and for TI with mean $AUC_{INS}$ measured at 9155 and 9180 µU/mL respectively (FIG. 10). Mean excursion of glucose from baseline for SC was 85 mg/dL and $AUC_{GLU}$ was 10925 min*mg/dL. In comparison, mean excursion of glucose from baseline for TI was 59 mg/dL and $AUC_{GLU}$ was 6969 min*mg/dL (FIG. 10). Thus the ratio of glucose excursion to insulin exposure in the above units, an indication of the effectiveness of the absorbed insulin dose, was only about 0.76 versus about 1.2 for TI and SC, respectively. The data demonstrate a 31% reduction (p=0.0022) of mean glucose excursion and a 36% reduction (p=0.0073) of glucose exposure over the 240 min measured for TI relative to SC.

With comparable exposure to insulin (as measured in the plasma), to meal quantity, and to meal composition, prandial TI resulted in significantly improved control of post-prandial peak glucose and total glucose exposure compared to prandial SC. The only differences between therapies were the insulin formulations and the methods of insulin administration. TI provided insulin Tmax that mimicked first-phase insulin release kinetics and which occurred at a time when it would be expected to have an effect on hepatic glucose release. SC insulin levels were much lower than TI during the early post-prandial period, did not exhibit a clear "peak" as did TI, and demonstrated a slow rise to maximum concentration—too late to be expected to control hepatic glucose release but sufficient to represent a risk for late post-prandial hypoglycemia.

Example 9

Markedly Reduced Postprandial Glucose Excursions Through Inhaled Technosphere®/Insulin in Comparison to SC Injected Regular Insulin in Subjects with Type 2 Diabetes Baseline adjusted postprandial total insulin exposure (INS-$AUC_{0-240}$ min) was comparable for TI and for SC (8187±4269 vs 8302±4025 min*µU/dL; ns) whereas baseline adjusted postprandial glucose excursion (BG-$AUC_{0-240}$ min) for TI was only about 50% of that of SC (5095±5923 min*mg/dL vs 9851±5593 min*mg/dL; p<0.008). Thus the ratio of glucose excursion to insulin exposure in the above units, an indication of the effectiveness of the absorbed insulin dose was only about 0.62 for TI versus about 1.2 for SC. In other words, unit for unit of absorbed insulin TI was nearly twice as efficient in removing glucose from the blood. With TI median insulin Tmax was shorter (15 vs 120 min; p<0.001) and median Cmax was higher (100 vs 54 µU/mL; p=0.001) than with SC. Accordingly, postprandial maximum adjusted blood glucose excursions were 28% lower with TI compared to SC (49 vs 82 mg/dL; p<0.003). The incidence of hypoglycemia (BG<63 mg/dL or hypoglycemic symptoms) was comparable between TI and SC (6 vs. 5 episodes) as was the number of treatment emerged (mild to moderate) adverse events (5 vs. 4 episodes). Hyperglycemia (BG>280 mg/dL) occurred more often with TI (12 vs. 4 episodes)—with two patients alone accounting for 8 episodes.

Technosphere®/Insulin markedly improved post-prandial glucose control compared to prandial SC while total serum insulin concentrations were comparable between both treatments. This was attributed to a rapid onset of action of TI in which insulin Tmax resembles first-phase insulin release kinetics. In contrast SC insulin levels were much lower than TI during the early post-prandial period and did not exhibit the clear peak observed with TI. These results support the conclusion that preprandial TI was superior to SC insulin in providing prandial insulin needs and reducing meal related blood glucose excursions.

Example 10

The Variability and Time-Action Profile of Inhaled Technosphere®/Insulin Compares Favorably to that of Subcutaneous Human Regular Insulin Timing and reproducibility and of insulin's metabolic effect is critical to achieve near-normal glucose control and to enable patients to make appropriate dose adjustments. The time-action profiles and the intra-subject variability in insulin absorption and insulin effect between repeated doses of 48 U inhaled Technosphere®/Insulin (TI) and 24 IU subcutaneous injected human regular insulin (SC) was compared.

Technosphere®/Insulin and SC were given on three separate occasions each on separate study days in a randomized sequence in 12 insulin-treated subjects with type 2 diabetes (10 males, 2 females, age 56 (range 40-65) years, diabetes duration 14.4 (3-29) years, HbA1c 6.9±0.9% (mean±SD), all normal lung function (FVC, FEV1 and VC=80% of predicted normal)). Using a euglycemic glucose clamp (clamp level 120 mg/dL), pharmacokinetic (PK) and pharmacodynamic (PD) time-action profiles were measured over 540 min following each form of insulin administration. Variability of absorption and effect, expressed as CV % of $AUC_{0-t}$, was determined at 120, 180 and 540 min after dosing.

Technosphere®/Insulin showed a more rapid onset of action and higher peak insulin concentrations (INS) than SC (table, INS-tmax 17±6 vs. 135±68 min, TI vs. SC, p<0.0001). Technosphere®/Insulin reached maximal glucose infusion rate (GIR) values already at 79±47 min, while the maximum effect of the SC dose occurred at 293±83 min (p<0.00001). The AUCs for both INS and GIR curves were higher for TI compared to SC in the first two and three hours after administration (Table 9). The variability in both insulin concentrations and insulin action was lower for TI compared to SC in the first three hours after administration (Table 9). At 270 min, GIR for TI had returned to baseline, and the variability in measured plasma insulin at 540 min was comparable to the variation of SC (CV %: $GIR-AUC_{0-540 min}$ 26% vs. 18% (TI vs. SC); $INS-AUC_{0-540 min}$ 16% vs. 15%).

Technosphere®/Insulin showed a more rapid onset and a shorter duration of action than subcutaneous human regular insulin which can make it suitable for replacement of prandial insulin secretion in patients with type 2 diabetes. In particular, TI can provide a lower risk of late postprandial hypoglycemia as, in contrast to SC, most of its glucose lowering effect occurred before the three hour point. Furthermore, the intra-patient variability of repeated inhalations of TI was superior to SC insulin during the first three hours after dosing which can facilitate dose titration.

median of about 10 to 14 minutes after inhalation, which is ideal for replicating the first-phase insulin release. The administration of insulin with this highly reproducible kinetic profile to ambulatory patients with diabetes has not been possible with other currently available insulin systems. Studies, such as the examples above, have demonstrated a 48% reduction in post-prandial glucose excursion with TI compared to a bio-available equivalent dose of subcutaneous insulin (SC) given before meals. In another multi-center study of type 2 patients taking prandial TI in an ambulatory setting for 12 weeks, the frequency of prospectively monitored hypoglycemia was less than 10% of the frequency historically reported for SC in ambulatory use.

In a randomized, prospective double blind, placebo controlled study of the forced titration of prandial Technosphere®/Insulin in patients with type 2 diabetes mellitus subjects received inhaled Technosphere®/Insulin (TI), dosed prandially, in addition to basal administration of SC insulin glargine (Lantus®; a form of long acting insulin), 227 patients were studied over 18 weeks. During the initial 4-weeks, patients were followed on their existing therapy and then removed from all oral anti-hyperglycemic therapy and placed on fixed doses of SC insulin glargine taken once daily, in a dose sufficient to replicate their documented pre-manipulation fasting plasma glucose levels and stabilized at this dose. The patients were then randomized to blinded doses of added inhaled placebo or blinded doses of inhaled TI containing 14, 28, 42 or 56 U of regular human insulin taken at the time of each main meal of the day in a forced titration scenario over 4 weeks. Specifically, the subjects, divided into five cohorts, initially received placebo (Technosphere® microparticles without any insulin) along

TABLE 10

Pharmacokinetic Parameters after Pulmonary Administration of TI

| | Inhaled Technosphere ® Insulin | | SC Human Regular Insulin | |
|---|---|---|---|---|
| | mean ± SD | CV (%) [95% CI] | mean ± SD | CV (%) [95% CI] |
| Pharmacodynamic (PD) Parameters, based on glucose infusion rates (GIR) | | | | |
| $GIR-AUC_{0-2 h}$ (mg/kg) | 265 ± 83 (44% of total) | 23.4 [13.9-33.0] | 211 ± 84 (16% of total) | 39.2 [23.2-55.2] |
| $GIR-AUC_{0-3 h}$ (mg/kg) | 355 ± 119 (59% of total) | 21.7 [12.9-30.6] | 363 ± 153 (27% of total) | 33.4 [19.8-47.1] |
| $GIR_{max}$ (mg/kg/min) | 4.5 ± 1.0⁺ | 22.0 [13.0-30.9] | 5.5 ± 1.4 | 17.3 [10.3-24.4] |
| Pharmacokinetic (PK) Parameters, based on plasma insulin (INS) concentrations | | | | |
| $INS-AUC_{0-2 h}$ (μU/ml) | 6965 ± 2233* (56% of total) | 19.1 [11.3-26.9] | 5509 ± 1094 (24% of total) | 27.1 [16.1-38.2] |
| $INS-AUC_{0-3 h}$ (μU/ml) | 8030 ± 2561 (64% of total) | 18.2 [10.8-24.6] | 8672 ± 1442 (38% of total) | 25.0 [14.8-35.2] |
| $INS-C_{max}$ (μU/ml) | 124 ± 44⁺ | 20.4 [12.1-28.8] | 63 ± 10 | 29.2 [17.3-41.2] |

CI: Confidence Interval
*p < 0.05 vs. SC,
⁺p < 0.0005 vs. SC (ANOVA, Mixed Effects Models)

Example 11

Multi-Center Study of Type 2 Patients Taking Prandial TI in an Ambulatory Setting Studies of the pharmacokinetics and pharmacodynamics of administering regular human insulin by pulmonary inhalation using Technosphere®/Insulin (TI) have indicated that maximal plasma insulin concentration can be achieved in a with the sc long acting insulin. After a week one cohort continued to receive placebo and four cohorts were switched to a TI dose of 14 U of insulin. After another week three cohorts were switched to a TI dose of 28 U, and so on until a final cohort reached a TI dose of 56 U. All cohorts then continued on the same dose for the remaining eight weeks of the trial.

HbA1c levels and meal challenges (300 min) were evaluated at the initial visit, at the start of randomized treatment and at completion. Comparisons were made between treatment groups and the placebo group. Safety was assessed by the frequency of defined hypoglycemic episodes and by the measurement of serial pulmonary function tests including $FEV_1$ and $DL_{CO}$. The addition of TI to insulin glargine produced a dose-dependent reduction in HbA1c levels. In patients treated for eight weeks at 56 units, the mean reduction was 0.79% greater than that observed in the insulin glargine/placebo group (p=0.0002). TI also produced a dose-dependent reduction in post-prandial glucose excursions with a maximal excursion averaging only 34 mg/dL at 56 U (p<0.0001). There were no severe hypoglycemic episodes, and the frequency of mild/moderate hypoglycemic episodes was not increased above that in subjects on insulin glargine alone. No changes were observed from baseline or between dosage groups in weight or pulmonary function. Thus inhaled Technosphere®/Insulin was able to improve the glycemic control of patients with type 2 diabetes without increasing the risk of hypoglycemia.

Example 12

A 3 Month Comparison in Type 1 Diabetes of Inhaled Technosphere®/Insulin to SC Administered Rapid-Acting Insulin Analogue as Prandial Insulin in a Basal/Prandial Regimen This study represents the first evaluation of long-term control in patients with type 1 diabetes, comparing Technosphere®/Insulin (TI) with a rapid-acting insulin analogue (RAA, Novolog®) as a comparator. Previous studies of has shown significantly better postprandial control than regular human insulin over 240 min in patients with type 2 diabetes.

Patients with type 1 diabetes (111 subjects, 18 to 80 years of age; HbA1c 7.0% and 11.5%) were enrolled in a randomized, open label study to receive TI or RAA as mealtime insulin in addition to basal insulin (Lantus®) for 12 weeks. Titration of both prandial and basal insulin was permitted at the physician's discretion. At baseline, week 8 and week 12, standardized meal tests were conducted to assess glucose excursions over 300 min (420 min at week 12), and HbA1c levels and lung function ($FEV_1$ and DLco) was evaluated in both groups. Lower maximum and total glucose excursions were observed in the first two hours following a standard meal in the group receiving TI insulin compared to those who were dosed with sc insulin. Over the following 3-4 hours, glycemia was maintained close to baseline levels in the TI group but fell below baseline in the patients receiving rapid acting insulin. No difference in HbA1c levels were observed between the two treatment groups. No adverse effects on pulmonary function were noted during the course of the study. Therefore, in a basal/prandial regimen in patients with type 1 diabetes, inhaled TI is an appropriate alternative to SC administered RAA and may offer the advantages of reducing both glucose excursions and the risk of late postprandial hypoglycemia.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of restoring normal insulin kinetics in a patient in need thereof comprising administering to a patient having an insulin-related disorder an inhaled insulin composition comprising a diketopiperazine such that said inhaled insulin composition produces in the patient a rapid increase in serum insulin concentration of between about 75 mU/L and about 375 mU/L within 20 minutes of administration, wherein said patient's glucose elimination rate returns to baseline by about 6 hours after administration.

2. The method of claim 1, wherein said rapid increase in serum insulin concentration is between about 100 mU/L and about 375 mU/L.

3. The method of claim 2, wherein said rapid increase in serum insulin concentration is between about 125 mU/L and about 375 mU/L.

4. The method of claim 1, wherein said rapid increase in serum insulin concentration is achieved within about 15 minutes after administration.

5. The method of claim 1, wherein said rapid increase in serum insulin concentration descends through half maximal within about 80 minutes after administration.

6. The method of claim 1, wherein said rapid increase in serum insulin concentration descends through half maximal within about 50 minutes after administration.

7. The method of claim 1, wherein said rapid increase in serum insulin concentration descends through half maximal within about 35 minutes after administration.

8. The method of claim 1, wherein said patient's glucose elimination rate reaches its maximum between about 30 and about 90 minutes after administration.

9. The method of claim 8, wherein said patient's glucose elimination rate reaches its maximum between about 45 and about 60 minutes after administration.

10. The method of claim 1, wherein said diketopiperazine is fumaryl diketopiperazine.

11. The method of claim 1, wherein said inhaled insulin composition is administered from approximately 10 minutes prior to a meal to approximately 30 minutes after a meal.

12. The method of claim 11 wherein about 74% of the glucose lowering activity of said inhaled insulin composition has been expended within about 180 minutes after administration.

13. The method of claim 12 wherein said patient's glucose elimination rate returns to baseline within about 270 minutes after administration.

14. A method of restoring normal insulin kinetics in a patient in need thereof wherein said comprising administering to a patient having an insulin-related disorder from approximately 10 minutes prior to a meal to approximately 30 minutes after a meal an inhaled insulin composition comprising fumaryl diketopiperazine;

wherein said composition produces in the patient a a rapid increase in serum insulin levels of at least between about 75 mU/L and about 375 mU/L achieved within about 20 minutes after administration; and wherein about 74% of the glucose lowering activity of said inhaled insulin composition has been expended within about 180 minutes after administration, and said patient's glucose elimination rate returns to baseline within about 270 minutes after administration.

* * * * *